(12) United States Patent
Kuo

(10) Patent No.: US 8,874,452 B2
(45) Date of Patent: *Oct. 28, 2014

(54) METHOD AND SYSTEM FOR PROVIDING DYNAMIC ORTHODONTIC ASSESSMENT AND TREATMENT PROFILES

(75) Inventor: Eric Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 1080 days.

This patent is subject to a terminal disclaimer.

(21) Appl. No.: 11/549,636

(22) Filed: Oct. 13, 2006

(65) Prior Publication Data

US 2007/0128573 A1 Jun. 7, 2007

Related U.S. Application Data

(63) Continuation-in-part of application No. 10/788,635, filed on Feb. 27, 2004, now Pat. No. 7,987,099, and a continuation-in-part of application No. 11/379,198, filed on Apr. 18, 2006, now Pat. No. 7,904,308.

(51) Int. Cl.
*G06Q 50/00* (2012.01)
*G06F 19/00* (2011.01)
*A61C 7/08* (2006.01)
*A61C 7/00* (2006.01)

(52) U.S. Cl.
CPC .......... *G06F 19/345* (2013.01); *A61C 7/08* (2013.01); *G06F 19/3443* (2013.01); *G06F 19/322* (2013.01); *G06F 2216/03* (2013.01); *A61C 7/002* (2013.01)
USPC .......................................................... 705/2

(58) Field of Classification Search
USPC ...................................................... 705/2, 3, 4
See application file for complete search history.

(56) References Cited

U.S. PATENT DOCUMENTS

| | | | |
|---|---|---|---|
| 7,244,230 B2* | 7/2007 | Duggirala et al. | 600/300 |
| 2004/0078222 A1* | 4/2004 | Khan et al. | 705/2 |
| 2004/0133083 A1* | 7/2004 | Comaniciu et al. | 600/301 |
| 2004/0147840 A1* | 7/2004 | Duggirala et al. | 600/437 |
| 2004/0193036 A1* | 9/2004 | Zhou et al. | 600/407 |
| 2005/0271996 A1* | 12/2005 | Sporbert et al. | 433/24 |
| 2006/0056670 A1* | 3/2006 | Hamadeh | 382/128 |

OTHER PUBLICATIONS

International Search Report and Written Opinion of the International Searching Authority for PCT Application No. PCT/US2007/081290 filed Oct. 12, 2007 to Align Technology, Inc.
International Preliminary Report on Patentability and Written Opinion of the International Searching Authority for PCT Application No. PCT/US2007/081290 filed Oct. 12, 2007, mailed Apr. 23, 2009.

* cited by examiner

*Primary Examiner* — Neal Sereboff
(74) *Attorney, Agent, or Firm* — Brooks, Cameron & Huebsch, PLLC

(57) ABSTRACT

Method and system including receiving one or more parameters associated with an orthodontic condition, receiving a treatment goal information associated with the orthodontic condition, and providing a predefined template associated with the received treatment goal information, wherein the predefined template includes at least one orthodontic condition related information, are provided.

21 Claims, 37 Drawing Sheets

Slope = Performance Index
$R^2$ = Predictability

| Type of Movement |
| --- |
| Expansion/Constriction (+/-X Translation) |
| Mesialization/Distalization (+/-Y Translation) |
| Intrusion (-Z Translation) |
| Extrusion (+Z Translation) |
| Tip/Angulation (X Rotation) |
| Torque/Inclination (Y Rotation) |
| Pure Rotation (Z Rotation) |

| Category 1201 | Component 1202 | #1 1203 | #2 1203 | #3 1203 | #4 1203 | #5 1203 | #6 1203 | #7 1203 | Number of Options 1204 |
|---|---|---|---|---|---|---|---|---|---|
| Sagittal | Right Canine | Right Canine Full Class 2+ | Right Canine Full Class 2 | Right Canine Partial Class 2 | Right Canine Class 1 | Right Canine Partial Class 3 | Right Canine Full Class 3 | Right Canine Full Class 3+ | 7 |
| Vertical | Anterior Overbite | Severe Anterior Deep Bite | Moderate Anterior Deep Bite | Mild Anterior Deep Bite | Normal Anterior Overbite | Mild Anterior Open Bite | Moderate Anterior Open Bite | Severe Anterior Open Bite | 7 |
| Horizontal | Upper Midline Relative to Lower Midline | Upper Midline to Right 2+ mm | Upper Midline to Right 1-2 mm | Upper Midline to Right 0-1 mm | Upper Midline Centered | Upper Midline to Left 0-1 mm | Upper Midline to Left 1-2 mm | Upper Midline to Left 2+ mm | 7 |
| Arch Length | Lower Arch Length | Lower Severe Crowding | Lower Moderate Crowding | Lower Mild Crowding | No Lower Discrepancy | Lower Mild Spacing | Lower Moderate Spacing | Lower Severe Spacing | 7 |

1200
FIGURE 12

| | Goal |
|---|---|
| Treatment Goal | 1 Pre-Restorative Set-up |
| | 2 Esthetic Alignment |
| | 3 Anterior Function Improvement |
| | 4 Optimal Set-up |

FIGURE 13

| | GOAL | ADDRESS |
|---|---|---|
| Treatment Goal | 1 | Pre-restorative set-up | XXX4 |
| | 2 | Esthetic Alignment | XX44 |
| | 3 | Anterior Function Improvement | 4X44 |
| | 4 | Optimal Set-up | 4444 |

| | | | | | | |
|---|---|---|---|---|---|---|
| Date | 12/15/2005 | | | | | |
| Doctor Name | Dr. John Jones | | | | | |
| Patient Name 1601 | Ron Smith | | | | | |
| Gender 1602 | Male | | | | | |
| Chief Concern(s) 1603 | Upper Spaces | Upper Crowding | High Canines | | | |
| | Lower Spaces | Lower Crowding | Crossbite | | | |
| | Buck Teeth | Open Bite | Bad Back Bite | | | |

| Summary | Component | | |
|---|---|---|---|
| Sagittal | Right Canine | Right Canine Partial Class 2 | EDIT |
| Vertical | Anterior Overbite | Moderate Anterior Deep Bite | EDIT |
| Horizontal | Upper Midline Relative to Lower Midline | Upper Midline to Left 0-1 mm | EDIT |
| Arch Length | Lower Arch Length | Lower Moderate Crowding | EDIT |
| | | | |
| | | | |

| Patient 2401 | Database Address 2402 | Sagittal 2404 | Vertical 2405 | Horizontal 2406 | Upper Arch Length 2407 | Lower Arch Length 2408 | Rotation 2409 | Vertical Correct 2410 | Midline Correct 2411 |
|---|---|---|---|---|---|---|---|---|---|
| M. Jones | 97557557 | Class II | Deep Bite | No Cross bite | Normal | Moderate Crowding | No Rotation | No Intrusion/ Extraction | < 2mm Midline Correction |
| Treat? | | | Y / N | Y / N | | Y / N | | | Y/N |
| L. Smith | 55772752 | Class I | Normal | Cross Bite | Moderate Crowding | Moderate Spacing | < 20° Rotation | No Intrusion/ Extraction | > 2 mm Midline Correction |
| Treat? | | | | Y / N | Y / N | Y / N | Y/N | | Y/N |

| | Dimension | Component | 1 | 2 | 3 | 4 | 5 | 6 | 7 | SELECTED VALUE |
|---|---|---|---|---|---|---|---|---|---|---|
| A | Sagittal | Right Canine | Right Canine Full Class 2+ | Right Canine Full Class 2 | Right Canine Partial Class 2 | Right Canine Class 1 | Right Canine Partial Class 3 | Right Canine Full Class 3 | Right Canine Full Class 3+ | 3 |
| B | Vertical | Anterior Overbite | Severe Anterior Deep Bite | Moderate Anterior Deep Bite | Mild Anterior Deep Bite | Normal Anterior Overbite | Mild Anterior Open Bite | Moderate Anterior Open Bite | Severe Anterior Open Bite | 2 |
| C | Horizontal | Upper Midline Relative to Lower Midline | Upper Midline to Right 2+ mm | Upper Midline to Right 1-2 mm | Upper Midline to Right 0-1 mm | Upper Midline Centered | Upper Midline to Left 0-1 mm | Upper Midline to Left 1-2 mm | Upper Midline to Left 2+ mm | 5 |
| D | Arch Length | Lower Arch Length | Lower Severe Spacing | Lower Moderate Spacing | Lower Mild Spacing | No Lower Discrepancy | Lower Mild Crowding | Lower Moderate Crowding | Lower Severe Crowding | 6 |

FIGURE 25

| INITIAL ADDRESS | GOAL ADDRESS (Condensed - FIG.13) | GOAL ADDRESS (Expanded - FIG. 14) | COMBINED ADDRESS (Condensed) | COMBINED ADDRESS (Expanded) |
|---|---|---|---|---|
| 3256 | 1 | 3254 | 3256:1 | 3256:3254 |
| 3256 | 2 | 3244 | 3256:2 | 3256:3244 |
| 3256 | 3 | 4244 | 3256:3 | 3256:4244 |
| 3256 | 4 | 4444 | 3256:4 | 3256:4444 |
| | | | | |

FIGURE 26

| | DATABASE ADDRESS | | | |
|---|---|---|---|---|
| | 3256:1 | 3256:2 | 3256:3 | 3256:4 |
| Text Description | Align for lower anterior veneers | Aligner lower anteriors and center midlines | Achieve class I canine, align lowers and center midlines | Achieve class I canine, ideal overbite, ideal alignment and center midlines |
| Treatment Length | <6 months | 6-12 months | 12-16 months | 24+ months |
| Skill Set 1 - restorative dentistry | Yes | Maybe | Maybe | Maybe |
| Skill Set 2 - Orthodontic Auxiliaries | No | No | Maybe | Maybe |
| Skill Set 3 - Sectional fixed appliances | No | No | Maybe | Yes |
| Sample Case | Case #1425 | Case #2634 | Case #3324 | Case #5243 |
| Case Difficulty | Easy | Easy | Moderate | Difficult |

FIGURE 27

METHOD AND SYSTEM FOR PROVIDING DYNAMIC ORTHODONTIC ASSESSMENT AND TREATMENT PROFILES

RELATED APPLICATIONS

This application is a Continuation in Part of patent application Ser. No. 10/788,635 entitled "Dental Data Mining" filed on Feb. 27, 2004 and a Continuation in Part of U.S. patent application Ser. No. 11/379,198 entitled "Method and System for Providing Indexing and Cataloguing of Orthodontic Related Treatment Profiles and Options" filed Apr. 18, 2006, the entire specifications of which are incorporated herein by reference.

FIELD OF THE INVENTION

The present invention is related generally to the field of orthodontics. More specifically, the present invention is related to methods and system for providing dynamic orthodontic assessment and treatment profiles.

BACKGROUND

A primary objective of orthodontics is to realign patients' teeth to positions where the teeth function optimally and have an aesthetic appearance. The goal of a doctor is to take the patient from their current condition ("initial" or "starting dentition") to a final condition ("treatment goal"). The result achieved is known as the "treatment outcome." There may be many ways to achieve the goal and these are known as "treatment options." The methodologies used by the doctor to get the patient to the goal are known as "treatment plan."

Often times, doctors establish the goal as "ideal" and discontinue treatment when they are as close as they can possibly get to the ideal. However, more recently with the growing use of 3-D computer graphics software services and programs in dentistry, the doctor can actually establish a custom treatment goal specific to each individual patient, and this goal may be a limited treatment goal and not ideal in every component of the bite. This is important because if the doctor is able to achieve 100% of the intended limited goal, the treatment may still be deemed a success, whereas it may be possible that if the doctor only achieves 75% of a completely "ideal" treatment goal, the treatment might not be deemed a success even though the amount of measured improvement on an absolute scale in the latter situation might be higher than in the limited treatment situation.

Typically, appliances such as fixed braces and wires are applied to a patient's teeth to gradually reposition them from an initial arrangement to a final arrangement. The diagnosis and treatment planning process of orthodontic cases can be imprecise as the final dentition of a patient is based on the knowledge and expertise of the treating doctor in assembling various parameters in an assessment of each patient's condition and in a determination of a final position for each tooth. Different clinicians will vary in their definitions of individual orthodontic parameters and their definition of how a case should ideally be treated will also often vary.

To overcome some of these subjective issues, various indices have been used to more objectively define a patient's initial dentition and final outcome. For example, the PAR (Peer Assessment Rating) index identifies how far a dentition is from a good occlusion. A score is assigned to various occlusal traits which make up a malocclusion. The individual scores are summed to obtain an overall total, representing the degree a case deviates from ideal functional alignment and occlusion. The PAR grader is then calibrated to a known standard set of orthodontic conditions so this individual is able to rate new cases similarly.

In PAR, a score of zero would indicate ideal alignment and positioning of all orthodontic dental components as defined by generally accepted occlusal and aesthetic relationships the orthodontic community has adopted, and higher scores would indicate increased levels of irregularity. The overall score can be recorded on both pre- and post-treatment dental casts. The difference between these scores represents the degree of improvement as a result of orthodontic intervention. In addition to the PAR index, other indices may be used such as Index of Complexity Outcome and Need (ICON), Index of Orthodontic Treatment Need (IOTN) and American Board of Orthodontics (ABO) indices. These indices also rely on individual dental measurements in order to derive an assessment of deviation from an ideal.

In view of the foregoing, it would be desirable to have methods and systems to provide dynamic orthodontic related assessment, diagnosis and/or treatment profiles.

SUMMARY OF THE INVENTION

In one embodiment, method and system including receiving one or more parameters associated with an orthodontic condition, receiving a treatment goal information associated with the orthodontic condition, and providing a predefined template associated with the received treatment goal information, wherein the predefined template includes at least one orthodontic condition related information are provided.

These and other features and advantages of the present invention will be understood upon consideration of the following detailed description of the invention and the accompanying drawings.

BRIEF DESCRIPTION OF THE DRAWINGS

FIG. 12 illustrates a tabular representation of the indexing system stored in the storage unit of FIG. 1 in accordance with one embodiment of the present invention;

FIG. 13 illustrates a representation of possible treatment goals for any given orthodontic case in one aspect of the present invention;

FIG. 16 illustrates the selection process display for use in the indexing system for the identified primary concern as "buck teeth" in accordance with one embodiment of the present invention;

FIG. 23 illustrates an exemplary patient summary display 2300 displayed on terminal 1101 for use in the indexing system in accordance with one embodiment of the present invention;

FIG. 24 illustrates a patient database 2400 in accordance with one embodiment of the present invention;

FIG. 25 illustrates the selection process for representative components for use in the indexing system in accordance with an embodiment of the present invention;

FIG. 26 illustrates an exemplary series of database addresses generated by combining the initial condition address with the treatment goal address in one embodiment of the present invention;

FIG. 27 illustrates an exemplary database for a patient in another embodiment of the present invention;

DETAILED DESCRIPTION

Digital treatment plans are now possible with 3-dimensional orthodontic treatment planning tools such as ClinCheck®. from Align Technology, Inc. or other software available from eModels and OrthoCAD, among others. These technologies allow the clinician to use the actual patient's dentition as a starting point for customizing the treatment plan. The ClinCheck®. technology uses a patient-specific digital model to plot a treatment plan, and then use a scan of the achieved treatment outcome to assess the degree of success of the outcome as compared to the original digital treatment plan as discussed in U.S. patent application Ser. No. 10/640,439, filed Aug. 21, 2003 and U.S. patent application Ser. No. 10/225,889 filed Aug. 22, 2002. The problem with the digital treatment plan and outcome assessment is the abundance of data and the lack of standards and efficient methodology by which to assess "treatment success" at an individual patient level. To analyze the information, a dental data mining system is used.

Figure 1A:
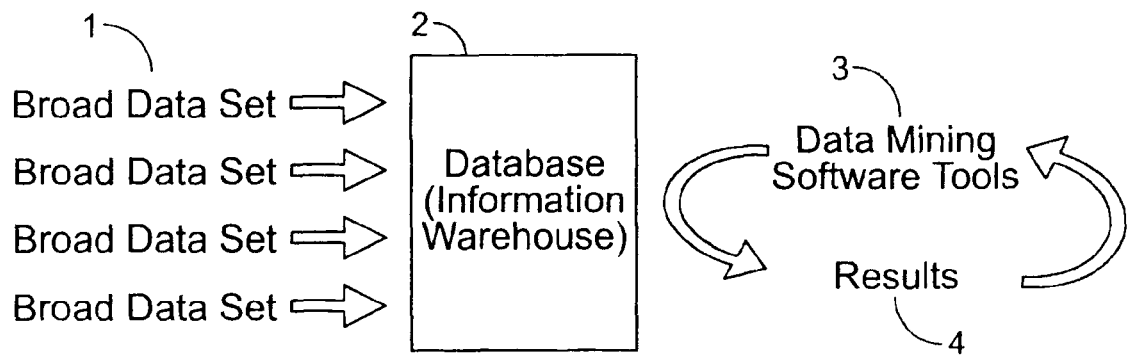
FIG. 1A shows one exemplary dental data mining system.

FIG. 1A shows one exemplary dental data mining system. In this system, dental treatment and outcome data sets 1 are stored in a database or information warehouse 2. The data is extracted by data mining software 3 that generates results 4. The data mining software can interrogate the information captured and/or updated in the database 2 and can generate an output data stream correlating a patient tooth problem with a dental appliance solution. Note that the output of the data mining software can be most advantageously, self-reflexively, fed as a subsequent input to at least the database and the data mining correlation algorithm.

The result of the data mining system of FIG. 1A is used for defining appliance configurations or changes to appliance configurations for incrementally moving teeth. The tooth movements will be those normally associated with orthodontic treatment, including translation in all three orthogonal directions, rotation of the tooth centerline in the two orthogonal directions with rotational axes perpendicular to a vertical centerline ("root angulation" and "torque"), as well as rotation of the tooth centerline in the orthodontic direction with an axis parallel to the vertical centerline ("pure rotation").

In one embodiment, the data mining system captures the 3-D treatment planned movement, the start position and the final achieved dental position. The system compares the outcome to the plan, and the outcome can be achieved using any treatment methodology including removable appliances as well as fixed appliances such as orthodontic brackets and wires, or even other dental treatment such as comparing achieved to plan for orthognathic surgery, periodontics, restorative, among others.

In one embodiment, a teeth superimposition tool is used to match treatment files of each arch scan. The refinement scan is superimposed over the initial one to arrive at a match based upon tooth anatomy and tooth coordinate system. After teeth in the two arches are matched, the superimposition tool asks for a reference in order to relate the upper arch to the lower arch. When the option "statistical filtering" is selected, the superimposition tool measures the amount of movement for each tooth by first eliminating as reference the ones that move (determined by the difference in position between the current stage and the previous one) more than one standard deviation either above or below the mean of movement of all teeth. The remaining teeth are then selected as reference to measure movement of each tooth.

Figure 1B:
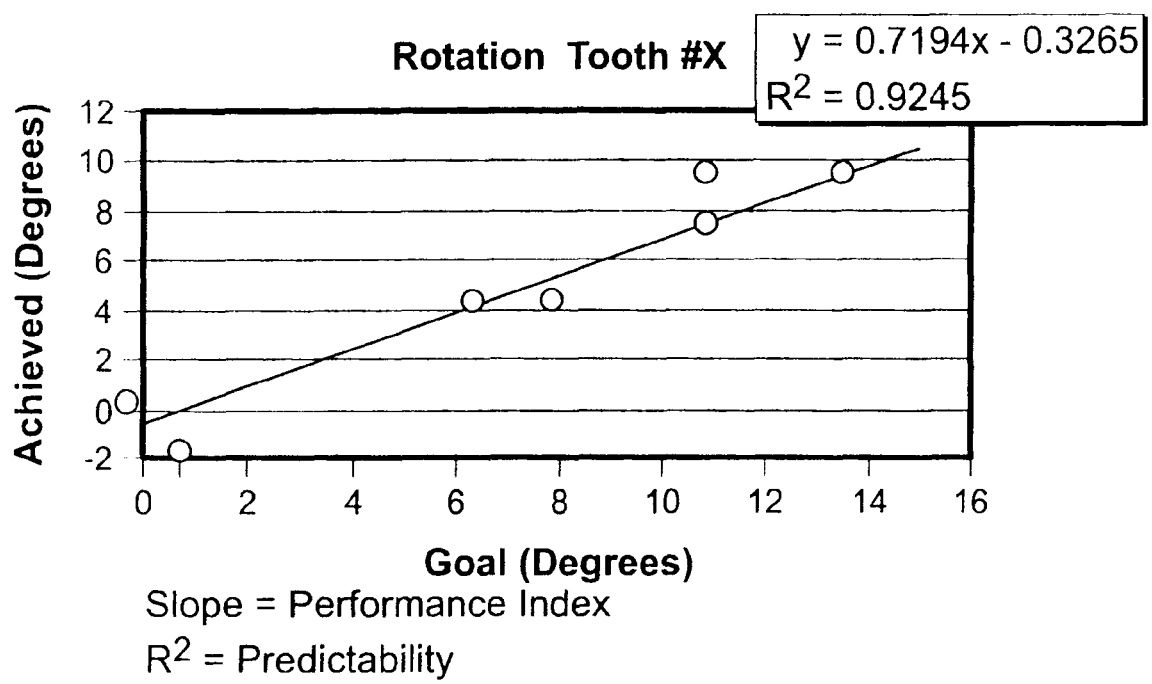
FIG. 1B shows an analysis of the performance of one or more dental appliances.

FIG. 1B shows an analysis of the performance of one or more dental appliances. "Achieved" movement is plotted against "Goal" movement in scatter graphs, and trend lines are generated. Scatter graphs are shown to demonstrate where all "scattered" data points are, and trend lines are generated to show the performance of the dental appliances. In one embodiment, trend lines are selected to be linear (they can be curvilinear); thus trend lines present as the "best fit" straight lines for all "scattered" data. The performance of the Aligners is represented as the slope of a trend line. The Y axis intercept models the incidental movement that occurs when wearing the Aligners. Predictability is measured by $R^2$ that is obtained from a regression computation of "Achieved" and "Goal" data.

Figures 1C, 1D:
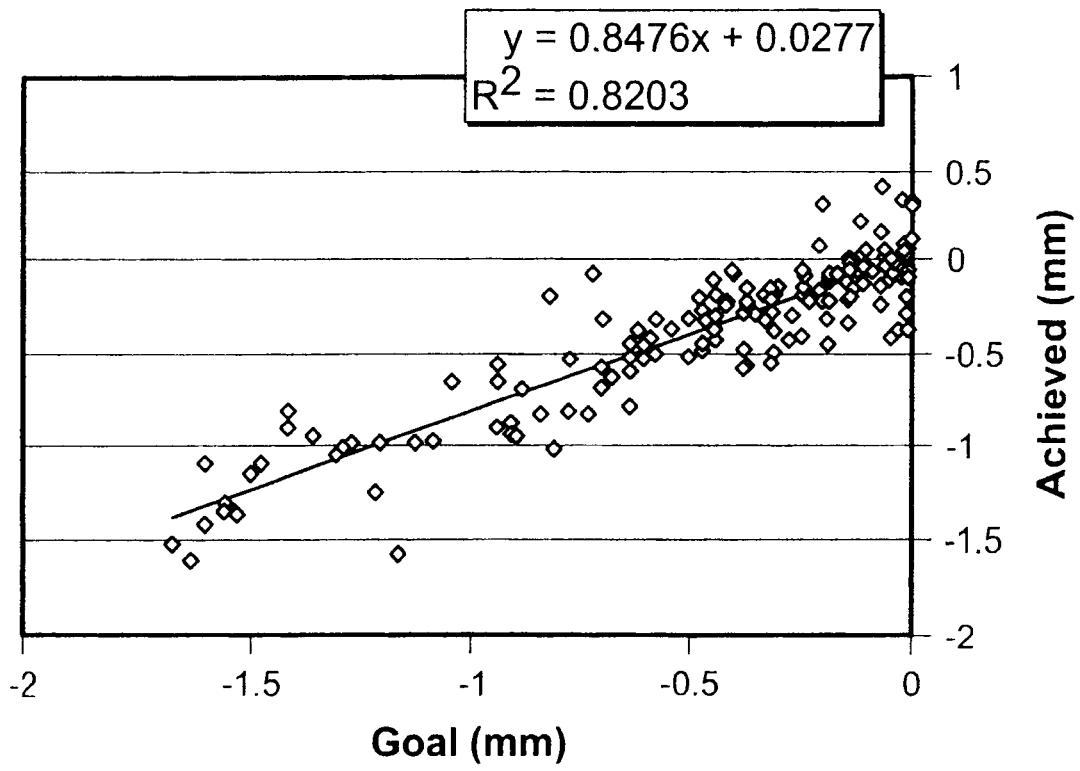
FIG. 1C shows various Movement Type data used in one embodiment of the data mining system.
FIG. 1D shows an analysis of the performance of one or more dental appliances.

FIG. 1C shows various Movement Type data used in one embodiment of the data mining system. Exemplary data sets cover Expansion/Constriction (+/−X Translation), Mesialization/Distalization (+/−Y Translation), Intrusion (−Z Translation), Extrusion (+Z Translation), Tip/Angulation (X Rotation), Torque/Inclination (Y Rotation), and Pure Rotation (Z Rotation).

FIG. 1D shows an analysis of the performance of one or more dental appliances. For the type of motion illustrated by FIG. 1D, the motion achieved is about 85% of targeted motion for that particular set of data.

As illustrated saliently in FIG. 1D, actual tooth movement generally lags targeted tooth movement at many stages. In the case of treatment with sequences of polymer appliances, such lags play an important role in treatment design, because both tooth movement and such negative outcomes as patient discomfort vary positively with the extent of the discrepancies.

In one embodiment, clinical parameters in steps such as 170 (FIG. 2A) and 232 (FIG. 2B) are made more precise by allowing for the statistical deviation of targeted from actual tooth position. For example, a subsequent movement target might be reduced because of a large calculated probability of currently targeted tooth movement not having been achieved adequately, with the result that there is a high probability the subsequent movement stage will need to complete work intended for an earlier stage. Similarly, targeted movement might overshoot desired positions especially in earlier stages so that expected actual movement is better controlled. This embodiment sacrifices the goal of minimizing round trip time in favor of achieving a higher probability of targeted end-stage outcome. This methodology is accomplished within treatment plans specific to clusters of similar patient cases.

Table 1 shows grouping of teeth in one embodiment. The sign convention of tooth movements is indicated in Table 2. Different tooth movements of the selected 60 arches were demonstrated in Table 3 with performance sorted by descending order. The appliance performance can be broken into 4 separate groups: high (79-85%), average (60-68%), below average (52-55%), and inadequate (24-47%). Table 4 shows ranking of movement predictability. Predictability is broken into 3 groups: highly predictable (0.76-0.82), predictable (0.43-0.63) and unpredictable (0.10-0.30). For the particular set of data, for example, the findings are as follows:

1. Incisor intrusion, and anterior intrusion performance are high. The range for incisor intrusion is about 1.7 mm, and for anterior intrusion is about 1.7 mm. These movements are highly predictable.

2. Canine intrusion, incisor torque, incisor rotation and anterior torque performance are average. The range for canine intrusion is about 1.3 mm, for incisor torque is about 34 degrees, for incisor rotation is about 69 degrees, and for anterior torque is about 34 degrees. These movements are either predictable or highly predictable.

3. Bicuspid tipping, bicuspid mesialization, molar rotation, and posterior expansion performance are below average. The range for bicuspid mesialization is about 1 millimeter, for bicuspid tipping is about 19 degrees, for molar rotation is about 27 degrees and for posterior expansion is about 2.8 millimeters. Bicuspid tipping and mesialization are unpredictable, whereas the rest are predictable movements.

4. Anterior and incisor extrusion, round teeth and bicuspid rotation, canine tipping, molar distalization, and posterior torque performance are inadequate. The range of anterior extrusion is about 1.7 millimeters, for incisor extrusion is about 1.5 mm, for round teeth rotation is about 67 degrees, for bicuspid rotation is about 63 degrees, for canine tipping is about 26 degrees, for molar distalization is about 2 millimeters, and for posterior torque is about 43 degrees. All are unpredictable movements except bicuspid rotation which is predictable.

TABLE 1

Studied groups of teeth

| Teeth | |
|---|---|
| Incisors | #7, 8, 9, 10, 23, 24, 25, 26 |
| Canines | #6, 11, 22, 27 |
| Bicuspids | #4, 5, 12, 13, 20, 21, 28, 29 |
| Molars | #2, 3, 14, 15, 18, 19, 30, 31 |
| Anteriors | #6, 7, 8, 9, 10, 11, 22, 23, 24, 25, 26, 27 |
| Posteriors | #2, 3, 4, 5, 12, 13, 14, 15, 18, 19, 20, 21, 28, 29, 30, 31 |
| Round | #4, 5, 6, 11, 12, 13, 20, 21, 22, 27, 28, 29 |

TABLE 2

Sign convention of tooth movements
Type of Movement

| | | |
|---|---|---|
| X translation (Expansion/ Constriction) | (−) is lingual | (+) is buccal |
| X rotation (Tipping) | | |
| Upper & Lower right quadrants | (−) is distal | (+) is mesial |
| Upper & Lower left quadrants | (−) is mesial | (+) is distal |
| Y translation (Mesialization/Distalization) | | |
| Upper left & Lower right quadrants | (−) is distal | (+) is mesial |
| Upper right & Lower left quadrants | (−) is mesial | (+) is distal |
| Y rotation (Torquing) | (−) is lingual crown | (+) is buccal crown |
| Z translation (Intrusion/Extrusion) | (−) is intrusion | (+) is extrusion |
| Z rotation (Pure Rotation) | (−) is clockwise | (+) is counterclockwise |

TABLE 3

Ranking of Performance Index of movement

| Group | Movement | Model | Performance Index | Side Effect | Predictability |
|---|---|---|---|---|---|
| Incisor | Intrusion | Linear | 85% | 0.03 | 0.82 |
| Anterior | Intrusion | Linear | 79% | 0.03 | 0.76 |
| Canine | Intrusion | Linear | 68% | −0.10 | 0.43 |
| Incisor | Torque | Linear | 67% | 0.21 | 0.63 |
| Anterior | Torque | Linear | 62% | 0.15 | 0.56 |
| Incisor | Rotation | Linear | 61% | −0.09 | 0.76 |
| Bicuspid | Tipping | Linear | 55% | 0.35 | 0.27 |
| Molar | Rotation | Linear | 52% | 0.11 | 0.58 |
| Posterior | Expansion | Linear | 52% | 0.11 | 0.48 |
| Bicuspid | Mesialization | Linear | 52% | 0.00 | 0.30 |
| Bicuspid | Rotation | Linear | 47% | 0.28 | 0.63 |
| Molar | Distalization | Linear | 43% | 0.02 | 0.20 |
| Canine | Tipping | Linear | 42% | 0.10 | 0.28 |
| Posterior | Torque | Linear | 42% | 1.50 | 0.28 |
| Round | Rotation | Linear | 39% | −0.14 | 0.27 |
| Anterior | Extrusion | Linear | 29% | −0.02 | 0.13 |
| Incisor | Extrusion | Linear | 24% | 0.02 | 0.10 |

TABLE 4

Ranking of movement predictability

| Group | Movement | Model | Performance Index | Side Effect | Predictability |
|---|---|---|---|---|---|
| Incisor | Intrusion | Linear | 85% | 0.03 | 0.82 |
| Anterior | Intrusion | Linear | 79% | 0.03 | 0.76 |
| Incisor | Rotation | Linear | 61% | −0.09 | 0.76 |
| Incisor | Torque | Linear | 67% | 0.21 | 0.63 |
| Bicuspid | Rotation | Linear | 47% | 0.28 | 0.63 |
| Molar | Rotation | Linear | 52% | 0.11 | 0.58 |
| Anterior | Torque | Linear | 62% | 0.15 | 0.56 |
| Posterior | Expansion | Linear | 52% | 0.11 | 0.48 |
| Canine | Intrusion | Linear | 68% | −0.10 | 0.43 |
| Bicuspid | Mesialization | Linear | 52% | 0.00 | 0.30 |
| Canine | Tipping | Linear | 42% | 0.10 | 0.28 |
| Posterior | Torque | Linear | 42% | 1.50 | 0.28 |
| Bicuspid | Tipping | Linear | 55% | 0.35 | 0.27 |
| Round | Rotation | Linear | 39% | −0.14 | 0.27 |
| Molar | Distalization | Linear | 43% | 0.02 | 0.20 |
| Anterior | Extrusion | Linear | 29% | −0.02 | 0.13 |
| Incisor | Extrusion | Linear | 24% | 0.02 | 0.10 |

In one embodiment, data driven analyzers may be applied. These data driven analyzers may incorporate a number of models such as parametric statistical models, non-parametric statistical models, clustering models, nearest neighbor models, regression methods, and engineered (artificial) neural networks. Prior to operation, data driven analyzers or models are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In one embodiment, the data mining software 3 (FIG. 1A) can be a "spider" or "crawler" to grab data on the database 2 (FIG. 1A) for indexing. In one embodiment, clustering operations are performed to detect patterns in the data. In another embodiment, a neural network is used to recognize each pattern as the neural network is quite robust at recognizing dental treatment patterns. Once the treatment features have been characterized, the neural network then compares the input dental information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

Dynamic programming considers all possible paths of M "frames" through N points, subject to specified costs for making transitions from any point i to any given frame k to any point j at the next frame k+1. Because the best path from the current point to the next point is independent of what happens beyond that point, the minimum total cost [i(k), j(k+1)] of a path through i(k) ending at j(k+1) is the cost of the transition itself plus the cost of the minimum path to i(k). Preferably, the values of the predecessor paths can be kept in an M×N array, and the accumulated cost kept in a 2×N array to contain the accumulated costs of the possible immediately preceding column and the current column. However, this method requires significant computing resources.

Dynamic programming requires a tremendous amount of computation. For the recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of dental treatment information against a given treatment model if the partial probability score for that comparison drops below a given threshold. This greatly reduces computation.

Considered to be a generalization of dynamic programming, a hidden Markov model is used in the preferred embodiment to evaluate the probability of occurrence of a sequence of observations O(1), O(2), O(t), . . . , O(T), where each observation O(t) may be either a discrete symbol under the VQ approach or a continuous vector. The sequence of observations may be modeled as a probabilistic function of an underlying Markov chain having state transitions that are not directly observable.

In the preferred embodiment, the Markov model is used to model probabilities for sequences of treatment observations. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j), where the b(j) term of the output symbol matrix is the function that when evaluated on a specified value O(t) returns the probability of outputting observation O(t), given that the model is in state j. The first state is always constrained to be the initial state for the first time frame of the Markov chain, only a prescribed set of left to right state transitions are possible. A predetermined final state is defined from which transitions to other states cannot occur.

In one embodiment, transitions are restricted to reentry of a state or entry to one of the next two states. Such transitions are defined in the model as transition probabilities. For example, a treatment pattern currently having a frame of feature signals in state 2 has a probability of reentering state 2 of a(2,2), a probability a(2,3) of entering state 3 and a probability of a(2,4)=1−a(2,2)−a(2,3) of entering state 4. The probability a(2,1) of entering state 1 or the probability a(2,5) of entering state 5 is zero and the sum of the probabilities a(2,1) through a(2,5) is one. Although the preferred embodiment restricts the flow graphs to the present state or to the next two states, one skilled in the art can build an HMM model with more flexible transition restrictions, although the sum of all the probabilities of transitioning from any state must still add up to one.

In each state j of the model, the current feature frame may be identified with one of a set of predefined output symbols or may be labeled probabilistically. In this case, the output symbol probability b(j) (O(t)) corresponds to the probability assigned by the model that the feature frame symbol is O(t). The model arrangement is a matrix A=[a(i,j)] of transition probabilities and a technique of computing B=[b(j) (O(t))].

In one embodiment, the Markov model is formed for a reference pattern from a plurality of sequences of training patterns and the output symbol probabilities are multivariate Gaussian function probability densities. The dental treatment information traverses through the feature extractor. During learning, the resulting feature vector series is processed by a parameter estimator, whose output is provided to the hidden Markov model. The hidden Markov model is used to derive a set of reference pattern templates, each template representative of an identified pattern in a vocabulary set of reference treatment patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

The HMM template has a number of states, each having a discrete value. However, as treatment pattern features may have a dynamic pattern in contrast to a single value, the addition of a neural network at the front end of the HMM in an embodiment provides the capability of representing states with dynamic values. The input layer of the neural network comprises input neurons. The outputs of the input layer are distributed to all neurons in the middle layer. Similarly, the outputs of the middle layer are distributed to all output neurons, which output neurons correspond one-to one with internal states of the HMM. However, each output has transition probabilities to itself or to other outputs, thus forming a modified HMM. Each state of the thus formed HMM is capable of responding to a particular dynamic signal, resulting in a more robust HMM. Alternatively, the neural network can be used alone without resorting to the transition probabilities of the HMM architecture.

The output streams or results 4 of FIG. 1A are used as feedback in improving dental appliance design and/or usage by doctors. For example, the data mining results can be used to evaluate performance based on staging approaches, to compare appliance performance indices based on treatment approaches, and to evaluate performance comparing different attachment shapes and positions on teeth.

The ability to study tooth-specific efficacy and product performance for large clusters of treatment outcomes enables statistically significant comparisons to be made between two or more populations of cases. In the event that the two clusters studied contain differences in treatment approach, appliance design, or manufacturing protocol, the differences seen in the performance of the product as exhibited by the data output, can be attributed to the approach, design, or manufacturing protocol. The end result is a feedback mechanism that enables either the clinician or the manufacturer the ability to optimize the product design and usage based on performance data from a significantly large sample size using objective measurable data.

The theory of orthodontic treatment is not universally agreed upon, and actual treatment and outcomes are subject to additional uncertainties of measurement of patient variables, of relationships to unmeasured patient variables, as well as of varying patient compliance. As a result, different clinicians might prefer different treatment plans for a single patient. Thus, a single treatment plan may not be accepted by every clinician since there is no universally accepted "correct" treatment plan.

The next few embodiments allow greater clinician satisfaction and greater patient satisfaction by tailoring treatment parameters to preferences of clinicians. The system detects differences in treatment preferences by statistical observation of the treatment histories of clinicians. For example, clinicians vary in how likely they would be to perform bicuspid extraction in cases with comparable crowding. Even when there is not a sufficient record of past treatments for a given clinician, clustering may be performed on other predictor variables such as geographical location, variables related to training, or size and nature of practice, to observe statistically significant differences in treatment parameters.

Data mining can discover statistically significant patterns of different treatment outcomes achieved by different clinicians for comparable patients. For example, patient cases clustered together might have systematically fewer complications with one clinician as compared to another. Such a difference detected by the data mining tool might be used as a flag for feedback to the more poorly performing clinician as well as a flag for solicitation of treatment differences used by the better performing clinician.

In one embodiment, clustering techniques are used with previously completed cases to categorize treatment complications and outcomes. Probability models of risk are then built within each cluster. New cases are then allocated to the same clusters based on similarity of pre-treatment variables. The risks within each cluster of patients with completed treatments are then used with new cases to predict treatment outcomes and risks of complications. High-risk patients are then flagged for special attention, possibly including additional steps in treatment plan or additional clinical intervention.

In another embodiment, practitioners are clustered into groups by observed clinician treatment preferences, and treatment parameters are adjusted within each group to coincide more closely with observed treatment preferences. Practitioners without observed histories are then assigned to groups based on similarity of known variables to those within clusters with known treatment histories.

Figure 1E:
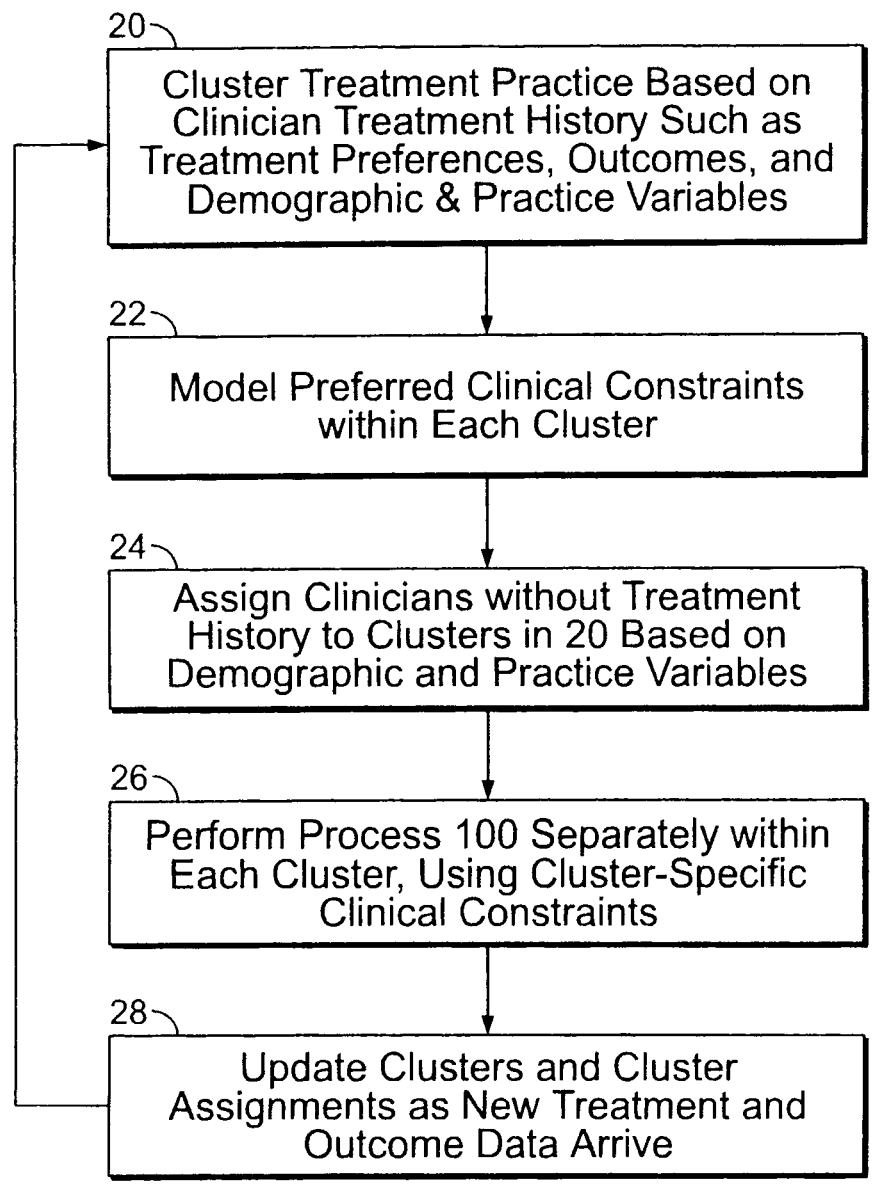
FIGS. 1E-1F show various embodiments of a clusterizer to generate treatment plans.

FIG. 1E shows an exemplary process for clusterizing practices. First, the process clusterizes treatment practice based on clinician treatment history such as treatment preferences, outcomes, and demographic and practice variables (20). Next, the system models preferred clinical constraints within each cluster (22). Next, the system assigns clinicians without treatment history to clusters in 20 based on demographic and practice variables (24). In one embodiment, the system performs process 100 (see FIG. 2A) separately within each cluster, using cluster-specific clinical constraints (26). Additionally, the system updates clusters and cluster assignments as new treatment and outcome data arrives (28).

Figure 1F:
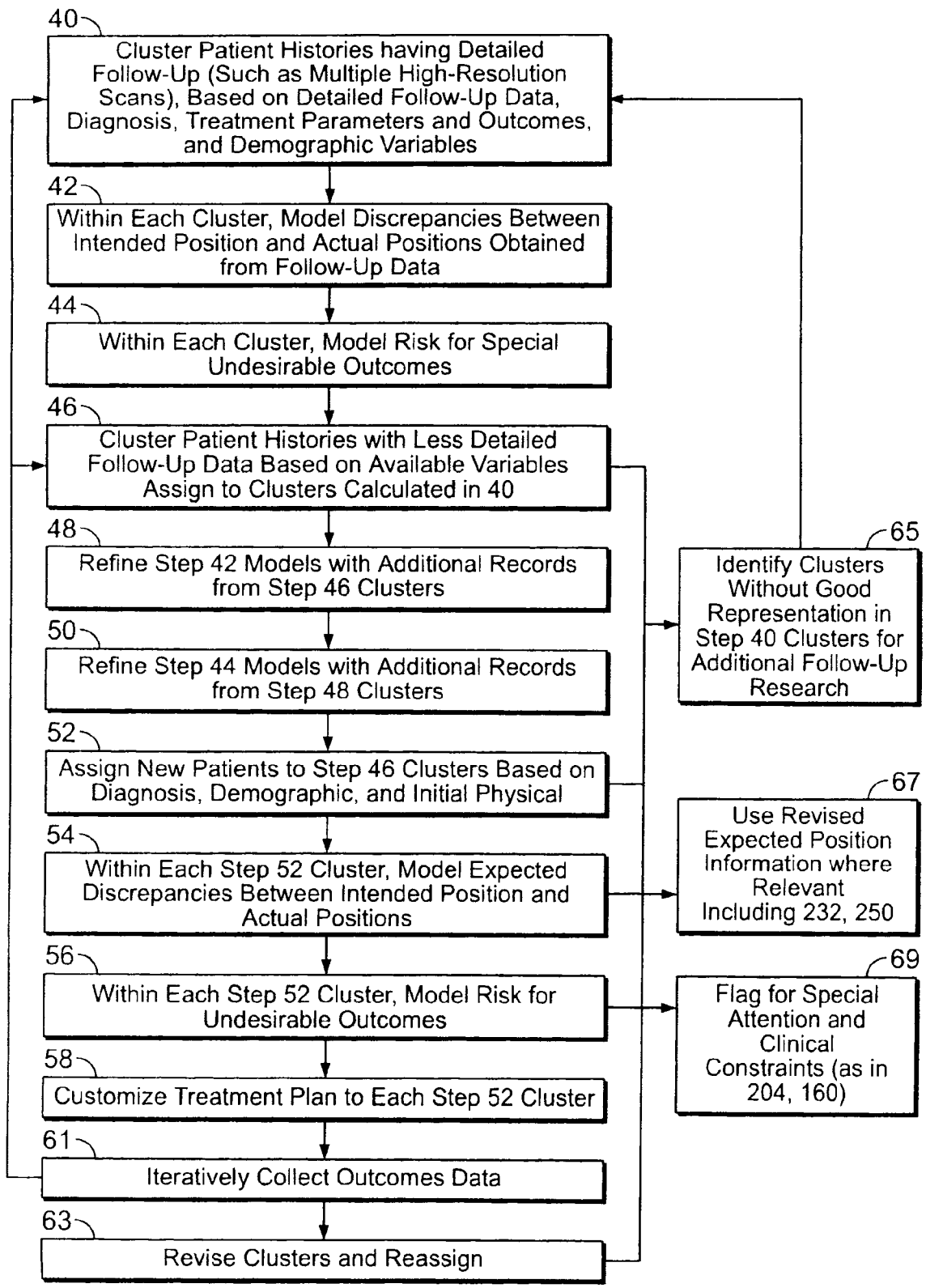

FIG. 1F shows another embodiment of a data mining system to generate proposed treatments. First, the system identifies/clusterizes patient histories having detailed follow-up (such as multiple high-resolution scans), based on detailed follow-up data, diagnosis, treatment parameters and outcomes, and demographic variables (40). Within each cluster, the system models discrepancies between intended position and actual positions obtained from follow-up data (42). Further, within each cluster, the system models risk for special undesirable outcomes (44). At a second tier of clustering, patient histories with less detailed follow-up data are clusterized based on available variables. The second-tier clustering is partial enough that each of the larger number of second tier clusters can either be assigned to clusters calculated in 40 or else considered a new cluster (46). The system refines step 42 models with additional records from step 46 clusters (48). It can also refine step 44 models with additional records from step 48 clusters (50). At a third tier of clustering, the system then assigns new patients to step 46 clusters based on diagnosis, demographic, and initial physical (52). Within each step 52 cluster, the system models expected discrepancies between intended position and actual positions (54). From step 54, the system uses revised expected position information where relevant (including 232 and 250, FIG. 2B) (67). Additionally, within each step 52 cluster, the system models risk for undesirable outcomes (56). From step 56, the system also flags cases that require special attention and clinical constraints (as in 204 and 160, FIGS. 2B and 2A) (69). The process then customizes treatment plan to each step 52 cluster (58). Next, the system iteratively collects data (61) and loops back to identify/clusterize patient histories (40). Additionally, clusters can be revised and reassigned (63). The system also continually identifies clusters without good representation for additional follow-up analysis (65).

In clinical treatment settings, it is not cost-effective to obtain or process the full high-resolution data possible at every stage of tooth movement. For example:

Patients may use several appliances between visits to clinicians.

A given patient may submit only one set of tooth impressions.

Radiation concerns may limit the number of CT or X-Ray scans used.

Clinicians generally do not have the time to report detailed spatial information on each tooth at each visit.

Due to these and other limitations, treatment planning is necessarily made based on partial information.

In one embodiment, missing information is approximated substantially by matching predictive characteristics between patients and a representative sample for which detailed follow-up information is collected. In this case, patients are flagged based on poorly anticipated treatment outcomes for requests for follow-up information, such as collection and analysis of additional sets of tooth impressions. Resulting information is then used to refine patient clusters and treatment of patients later assigned to the clusters.

In general, patient data is scanned and the data is analyzed using the data mining system described above. A treatment plan is proposed by the system for the dental practitioner to approve. The dental practitioner can accept or request modifications to the treatment plan. Once the treatment plan is approved, manufacturing of appliance(s) can begin.

Figure 2A:
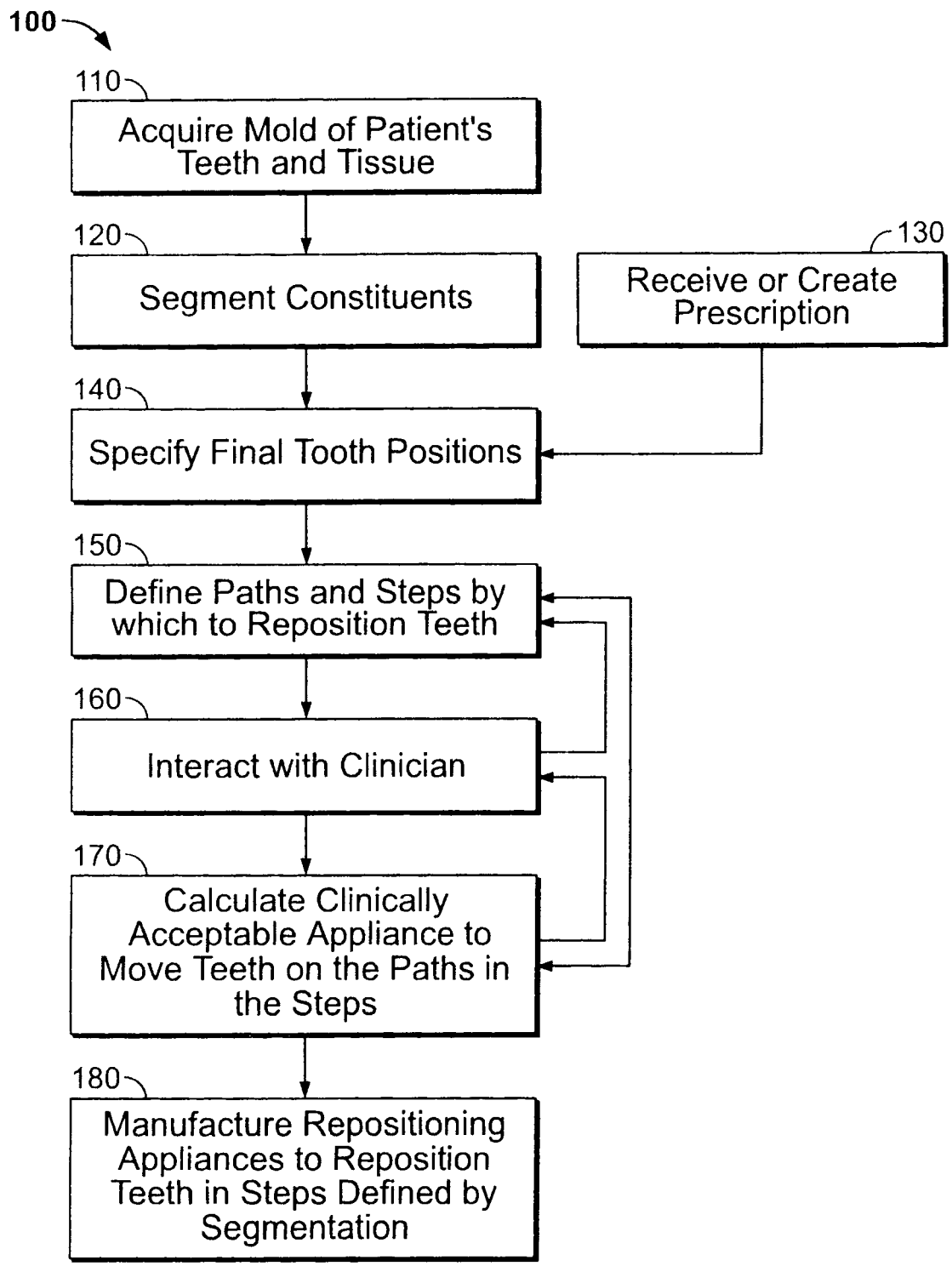
FIG. 2A is a flowchart of a process of specifying a course of treatment including a subprocess for calculating aligner shapes in accordance with the invention.

FIG. 2A illustrates the general flow of an exemplary process 100 for defining and generating repositioning appliances for orthodontic treatment of a patient. The process 100 includes the methods, and is suitable for the apparatus, of the present invention, as will be described. The computational steps of the process are advantageously implemented as computer program modules for execution on one or more conventional digital computers.

As an initial step, a mold or a scan of patient's teeth or mouth tissue is acquired (110). This step generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to segment the tissue constituents from each other (step 120). In particular, in this step, data structures that digitally represent individual tooth crowns are produced. Advantageously, digital models of entire teeth are produced, including measured or extrapolated hidden surfaces and root structures.

The desired final position of the teeth—that is, the desired and intended end result of orthodontic treatment—can be received from a clinician in the form of a prescription, can be calculated from basic orthodontic principles, or can be extrapolated computationally from a clinical prescription (step 130). With a specification of the desired final positions of the teeth and a digital representation of the teeth themselves, the final position and surface geometry of each tooth can be specified (step 140) to form a complete model of the teeth at the desired end of treatment. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a final position for each tooth, the process next defines a tooth path for the motion of each tooth. In one embodiment, the tooth paths are optimized in the aggregate so that the teeth are moved in the quickest fashion with the least amount of round-tripping to bring the teeth from their initial positions to their desired final positions. (Round-tripping is any motion of a tooth in any direction other than directly toward the desired final position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation (step 170, described later), which may determine that at one or more points along one or more tooth paths, the forces that can be generated by the appliance on the then-existing configuration of teeth and tissue is incapable of effecting the repositioning that is represented by one or more tooth path segments. With this information, the sub-process defining segmented paths (step 150) can recalculate the paths or the affected subpaths.

At various stages of the process, and in particular after the segmented paths have been defined, the process can, and generally will, interact with a clinician responsible for the treatment of the patient (step 160). Clinician interaction can be implemented using a client process programmed to receive tooth positions and models, as well as path information from a server computer or process in which other steps of process 100 are implemented. The client process is advantageously programmed to allow the clinician to display an animation of the positions and paths and to allow the clinician to reset the final positions of one or more of the teeth and to specify constraints to be applied to the segmented paths. If the clinician makes any such changes, the subprocess of defining segmented paths (step 150) is performed again.

The segmented tooth paths and associated tooth position data are used to calculate clinically acceptable appliance configurations (or successive changes in appliance configuration) that will move the teeth on the defined treatment path in the steps specified by the path segments (step 170). Each appliance configuration represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with the path definition step, this appliance calculation step can include interactions and even iterative interactions with the clinician (step 160). The operation of a process step 200 implementing this step will be described more fully below.

Having calculated appliance definitions, the process 100 can proceed to the manufacturing step (step 180) in which appliances defined by the process are manufactured, or electronic or printed information is produced that can be used by a manual or automated process to define appliance configurations or changes to appliance configurations.

Figure 2B:
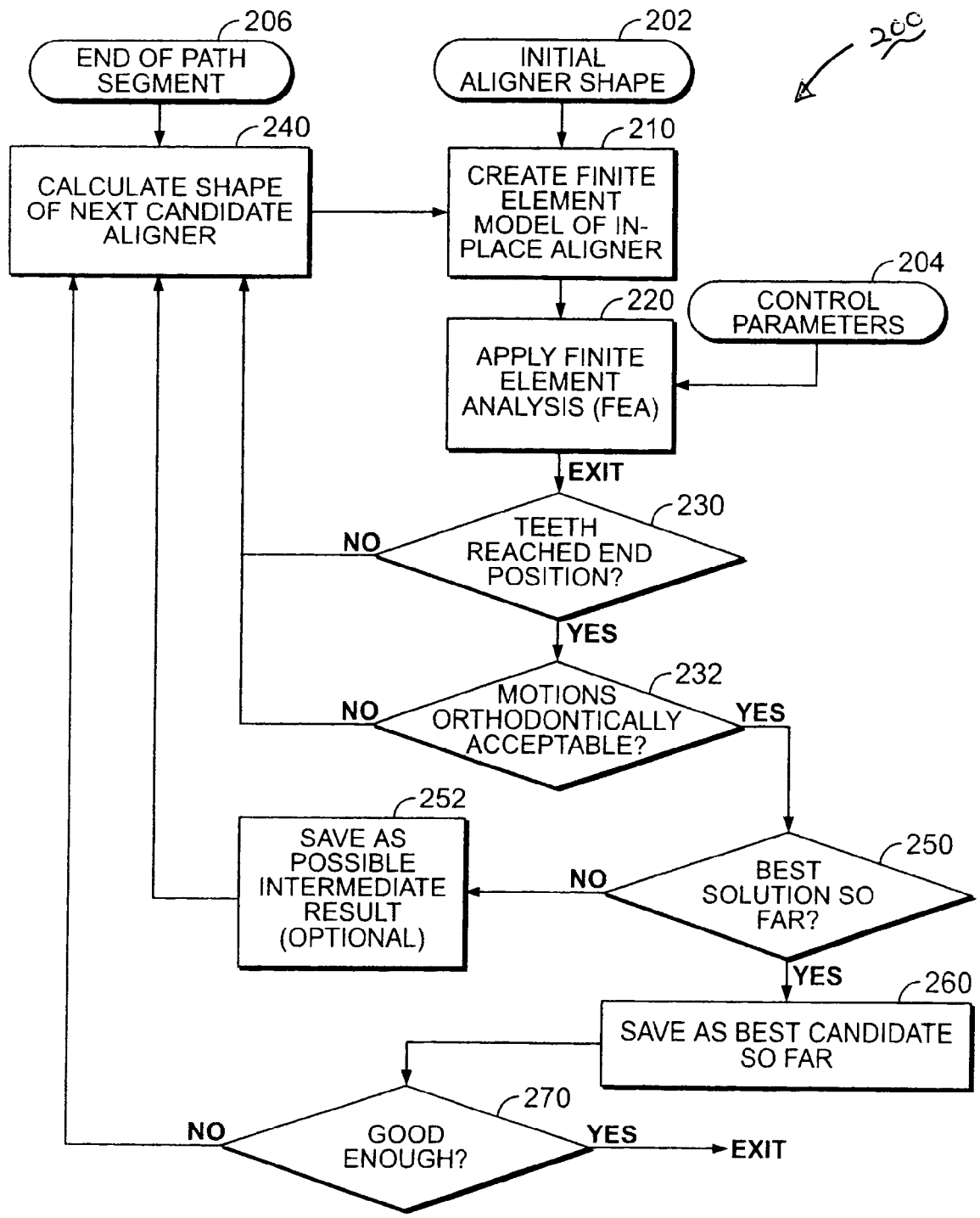
FIG. 2B is a flowchart of a process for calculating aligner shapes.

FIG. 2B illustrates a process 200 implementing the appliance-calculation step (FIG. 2A, step 170) for polymeric shell aligners of the kind described in above-mentioned U.S. Pat. No. 5,975,893. Inputs to the process include an initial aligner shape 202, various control parameters 204, and a desired end configuration for the teeth at the end of the current treatment path segment 206. Other inputs include digital models of the teeth in position in the jaw, models of the jaw tissue, and specifications of an initial aligner shape and of the aligner material. Using the input data, the process creates a finite element model of the aligner, teeth and tissue, with the aligner in place on the teeth (step 210). Next, the process applies a finite element analysis to the composite finite element model of aligner, teeth and tissue (step 220). The analysis runs until an exit condition is reached, at which time the process evaluates whether the teeth have reached the desired end position for the current path segment, or a position sufficiently close to the desired end position (step 230). If an acceptable end position is not reached by the teeth, the process calculates a new candidate aligner shape (step 240). If an acceptable end position is reached, the motions of the teeth calculated by the finite elements analysis are evaluated to determine whether they are orthodontically acceptable (step 232). If they are not, the process also proceeds to calculate a new candidate aligner shape (step 240). If the motions are orthodontically acceptable and the teeth have reached an acceptable position, the current aligner shape is compared to the previously calculated aligner shapes. If the current shape is the best solution so far (decision step 250), it is saved as the best candidate so far (step 260). If not, it is saved in an optional step as a possible intermediate result (step 252). If the current aligner shape is the best candidate so far, the process determines whether it is good enough to be accepted (decision step 270). If it is, the process exits. Otherwise, the process continues and calculates another candidate shape (step 240) for analysis.

The finite element models can be created using computer program application software available from a variety of vendors. For creating solid geometry models, computer aided engineering (CAE) or computer aided design (CAD) programs can be used, such as the AutoCAD®. software products available from Autodesk, Inc., of San Rafael, Calif. For creating finite element models and analyzing them, program products from a number of vendors can be used, including the PolyFEM product available from CADSI of Coralville, Iowa, the Pro/Mechanica simulation software available from Parametric Technology Corporation of Waltham, Mass., the I-DEAS design software products available from Structural Dynamics Research Corporation (SDRC) of Cincinnati, Ohio, and the MSC/NASTRAN product available from Mac-Neal-Schwendler Corporation of Los Angeles, Calif.

Figure 3:
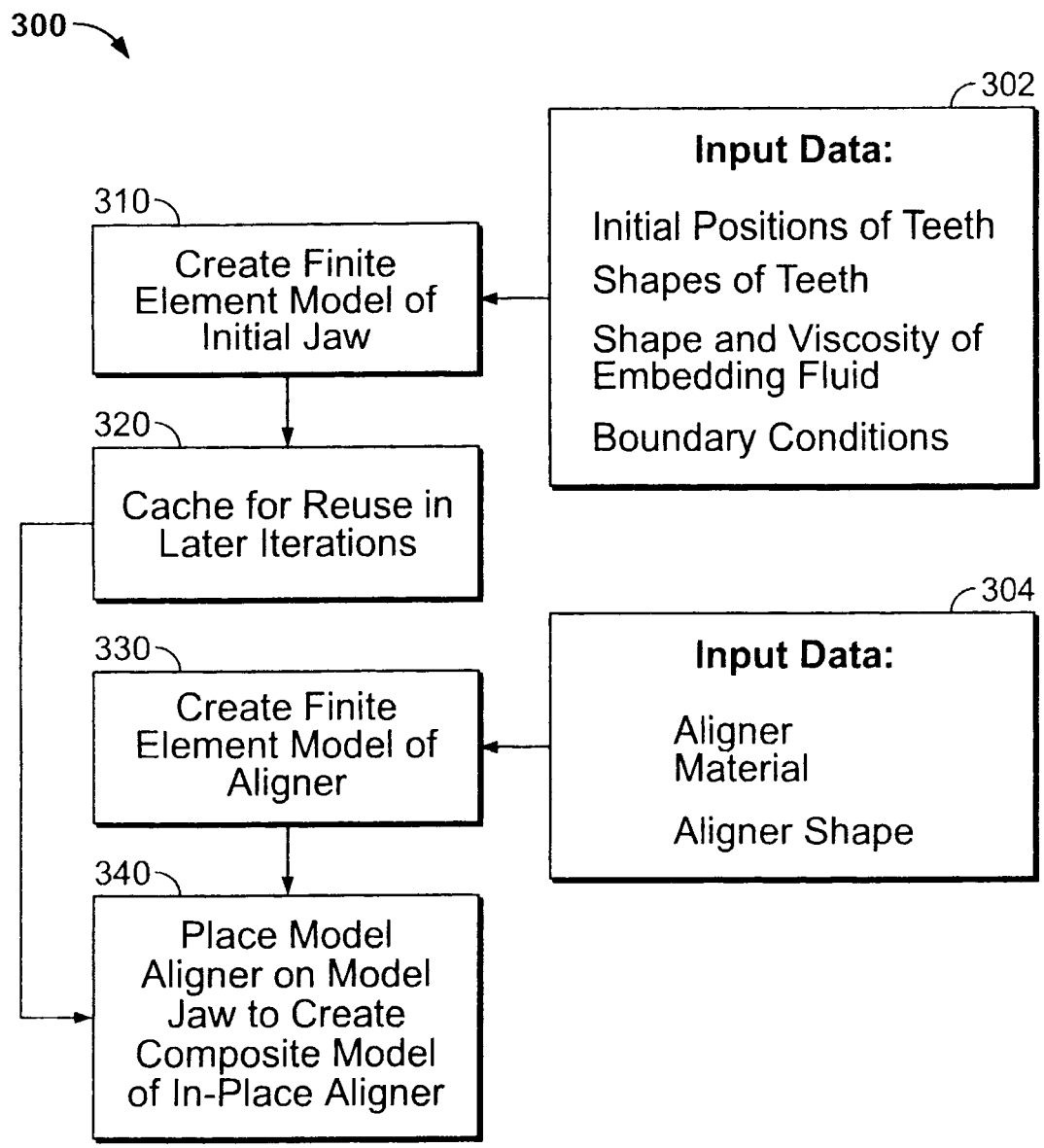
FIG. 3 is a flowchart of a subprocess for creating finite element models.

FIG. 3 shows a process 300 of creating a finite element model that can be used to perform step 210 of the process 200 (FIG. 2). Input to the model creation process 300 includes input data 302 describing the teeth and tissues and input data 304 describing the aligner. The input data describing the teeth 302 include the digital models of the teeth; digital models of rigid tissue structures, if available; shape and viscosity specifications for a highly viscous fluid modeling the substrate tissue in which the teeth are embedded and to which the teeth are connected, in the absence of specific models of those tissues; and boundary conditions specifying the immovable boundaries of the model elements. In one implementation, the model elements include only models of the teeth, a model of a highly viscous embedding substrate fluid, and boundary conditions that define, in effect, a rigid container in which the modeled fluid is held. Note that fluid characteristics may differ by patient clusters, for example as a function of age.

A finite element model of the initial configuration of the teeth and tissue is created (step 310) and optionally cached for reuse in later iterations of the process (step 320). As was done with the teeth and tissue, a finite element model is created of the polymeric shell aligner (step 330). The input data for this model includes data specifying the material of which the aligner is made and the shape of the aligner (data input 304).

The model aligner is then computationally manipulated to place it over the modeled teeth in the model jaw to create a composite model of an in-place aligner (step 340). Optionally, the forces required to deform the aligner to fit over the teeth, including any hardware attached to the teeth, are computed and used as a figure of merit in measuring the acceptability of the particular aligner configuration. Optionally, the tooth positions used are as estimated from a probabilistic model based on prior treatment steps and other patient information. In a simpler alternative, however, the aligner deformation is modeled by applying enough force to its insides to make it large enough to fit over the teeth, placing the model aligner over the model teeth in the composite model, setting the conditions of the model teeth and tissue to be infinitely rigid, and allowing the model aligner to relax into position over the fixed teeth. The surfaces of the aligner and the teeth are modeled to interact without friction at this stage, so that the aligner model achieves the correct initial configuration over the model teeth before finite element analysis is begun to find a solution to the composite model and compute the movement of the teeth under the influence of the distorted aligner.

Figure 4:
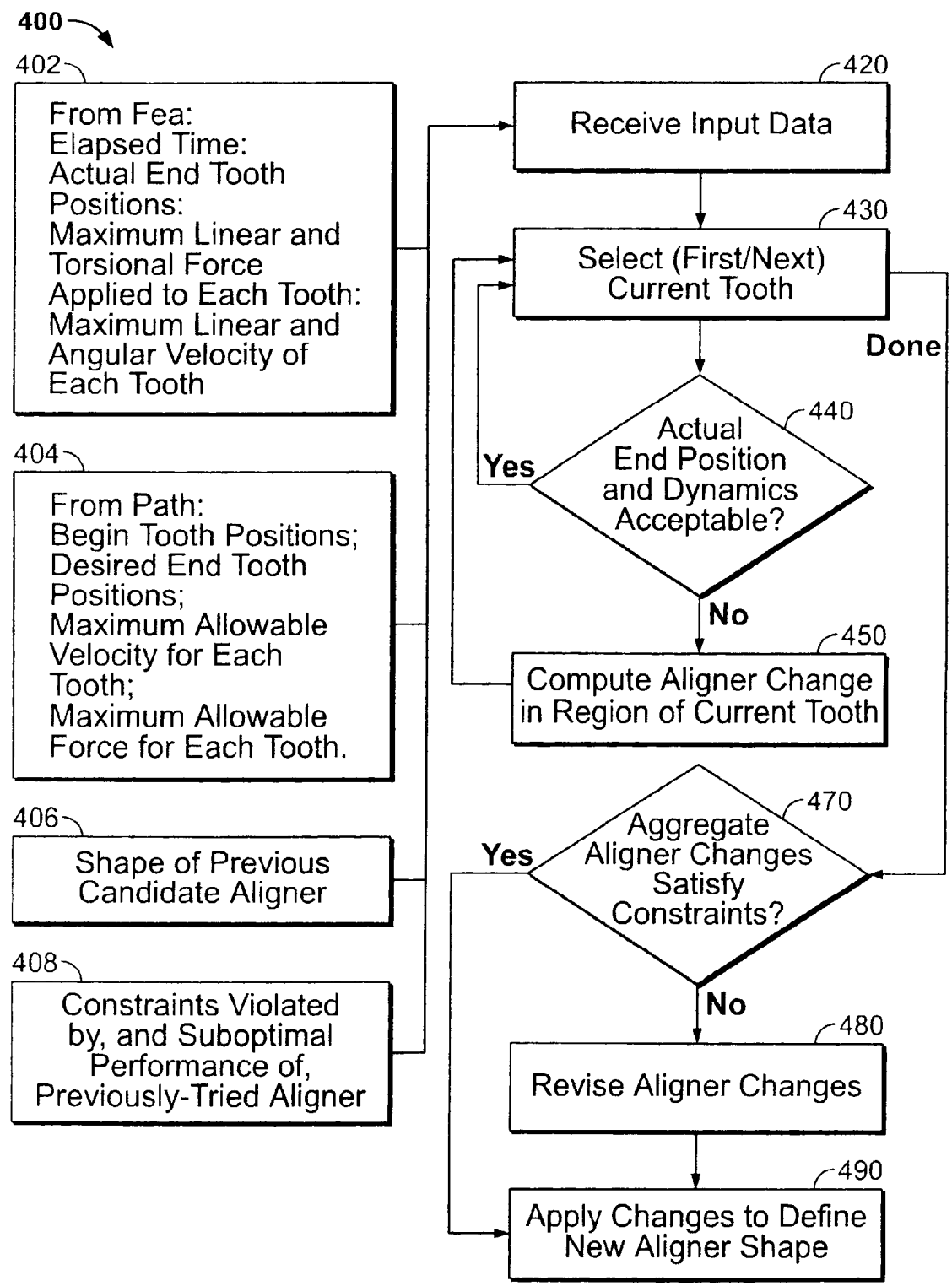
FIG. 4 is a flowchart of a subprocess for computing aligner changes.

FIG. 4 shows a process 400 for calculating the shape of a next aligner that can be used in the aligner calculations, step 240 of process 200 (FIG. 2B). A variety of inputs are used to calculate the next candidate aligner shape. These include inputs 402 of data generated by the finite element analysis solution of the composite model and data 404 defined by the current tooth path. The data 402 derived from the finite element analysis includes the amount of real elapsed time over which the simulated repositioning of the teeth took place; the actual end tooth positions calculated by the analysis; the maximum linear and torsional force applied to each tooth; the maximum linear and angular velocity of each tooth. From the input path information, the input data 404 includes the initial tooth positions for the current path segment, the desired tooth positions at the end of the current path segment, the maximum allowable displacement velocity for each tooth, and the maximum allowable force of each kind for each tooth.

If a previously evaluated aligner was found to violate one or more constraints, additional input data 406 can optionally be used by the process 400. This data 406 can include information identifying the constraints violated by, and any identified suboptimal performance of, the previously evaluated aligner. Additionally, input data 408 relating to constraints violated by, and suboptimal performance of previous dental devices can be used by the process 400.

Having received the initial input data (step 420), the process iterates over the movable teeth in the model. (Some of the teeth may be identified as, and constrained to be, immobile.) If the end position and dynamics of motion of the currently selected tooth by the previously selected aligner is acceptable ("yes" branch of decision step 440), the process continues by selecting for consideration a next tooth (step 430) until all teeth have been considered ("done" branch from step 430 to step 470). Otherwise ("no" branch from step 440), a change in the aligner is calculated in the region of the currently selected tooth (step 450). The process then moves back to select the next current tooth (step 430) as has been described.

When all of the teeth have been considered, the aggregate changes made to the aligner are evaluated against previously defined constraints (step 470), examples of which have already been mentioned. Constraints can be defined with reference to a variety of further considerations, such as manufacturability. For example, constraints can be defined to set a maximum or minimum thickness of the aligner material, or to set a maximum or minimum coverage of the aligner over the crowns of the teeth. If the aligner constraints are satisfied, the changes are applied to define a new aligner shape (step 490). Otherwise, the changes to the aligner are revised to satisfy the constraints (step 480), and the revised changes are applied to define the new aligner shape (step 490).

Figure 5A:
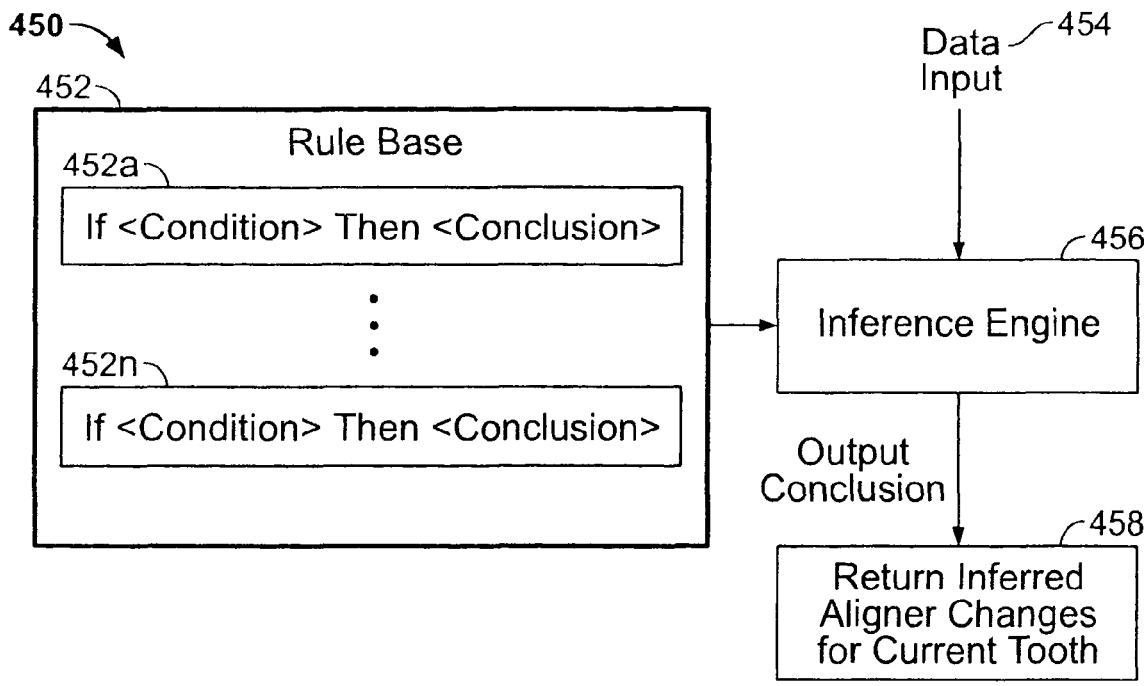
FIG. 5A is a flowchart of a subprocess for calculating changes in aligner shape.

FIG. 5A illustrates one implementation of the step of computing an aligner change in a region of a current tooth (step 450). In this implementation, a rule-based inference engine 456 is used to process the input data previously described (input 454) and a set of rules 452a-452n in a rule base of rules 452. The inference engine 456 and the rules 452 define a production system which, when applied to the factual input data, produces a set of output conclusions that specify the changes to be made to the aligner in the region of the current tooth (output 458).

Rules 452a . . . 452n have the conventional two-part form: an if-part defining a condition and a then-part defining a conclusion or action that is asserted if the condition is satisfied. Conditions can be simple or they can be complex conjunctions or disjunctions of multiple assertions. An exemplary set of rules, which defines changes to be made to the aligner, includes the following: if the motion of the tooth is too fast, add driving material to the aligner opposite the desired direction of motion; if the motion of the tooth is too slow, add driving material to overcorrect the position of the tooth; if the tooth is too far short of the desired end position, add material to overcorrect; if the tooth has been moved too far past the desired end position, add material to stiffen the aligner where the tooth moves to meet it; if a maximum amount of driving material has been added, add material to overcorrect the repositioning of the tooth and do not add driving material; if the motion of the tooth is in a direction other than the desired direction, remove and add material so as to redirect the tooth.

Figure 5B:
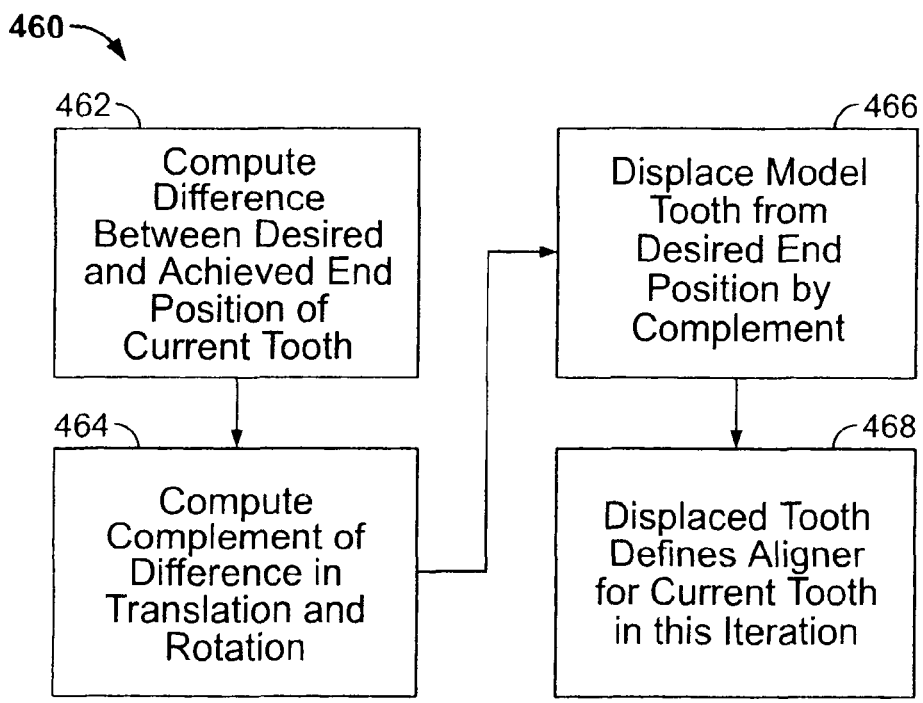
FIG. 5B is a flowchart of a subprocess for calculating changes in aligner shape.
Figure 5C:
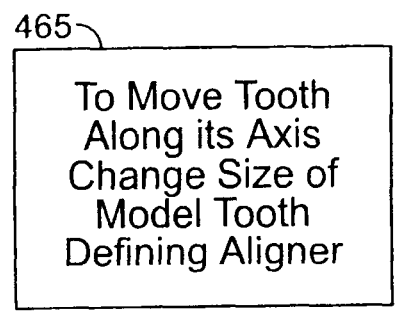
FIG. 5C is a flowchart of a subprocess for calculating changes in aligner shape.

In an alternative embodiment, illustrated in FIGS. 5B and 5C, an absolute configuration of the aligner is computed, rather than an incremental difference. As shown in FIG. 5B, a process 460 computes an absolute configuration for an aligner in a region of a current tooth. Using input data that has already been described, the process computes the difference between the desired end position and the achieved end position of the current tooth (462). Using the intersection of the tooth center line with the level of the gum tissue as the point of reference, the process computes the complement of the difference in all six degrees of freedom of motion, namely three degrees of translation and three degrees of rotation (step 464). Next, the model tooth is displaced from its desired end position by the amounts of the complement differences (step 466), which is illustrated in FIG. 5B.

Figure 5D:
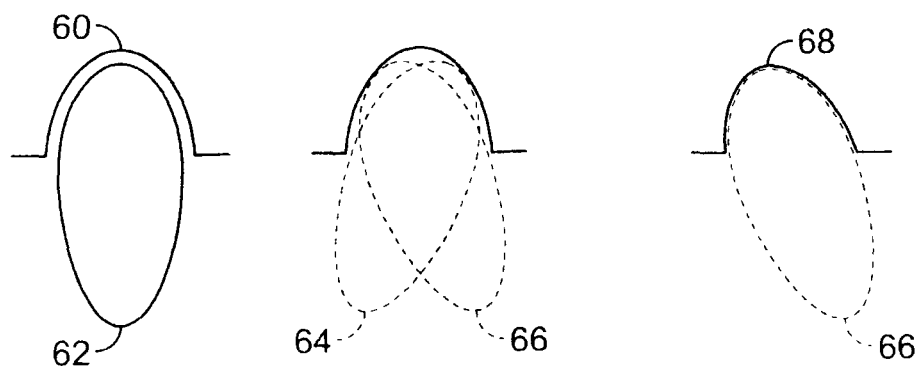
FIG. 5D is a schematic illustrating the operation of the subprocess of FIG. 5B.

FIG. 5D shows a planar view of an illustrative model aligner 60 over an illustrative model tooth 62. The tooth is in its desired end position and the aligner shape is defined by the tooth in this end position. The actual motion of the tooth calculated by the finite element analysis is illustrated as placing the tooth in position 64 rather than in the desired position 62. A complement of the computed end position is illustrated as position 66. The next step of process 460 (FIG. 5B) defines the aligner in the region of the current tooth in this iteration of the process by the position of the displaced model tooth (step 468) calculated in the preceding step (466). This computed aligner configuration in the region of the current tooth is illustrated in FIG. 5D as shape 68 which is defined by the repositioned model tooth in position 66.

A further step in process 460, which can also be implemented as a rule 452 (FIG. 5A), is shown in FIG. 5C. To move the current tooth in the direction of its central axis, the size of the model tooth defining that region of the aligner, or the amount of room allowed in the aligner for the tooth, is made smaller in the area away from which the process has decided to move the tooth (step 465).

Figure 6:
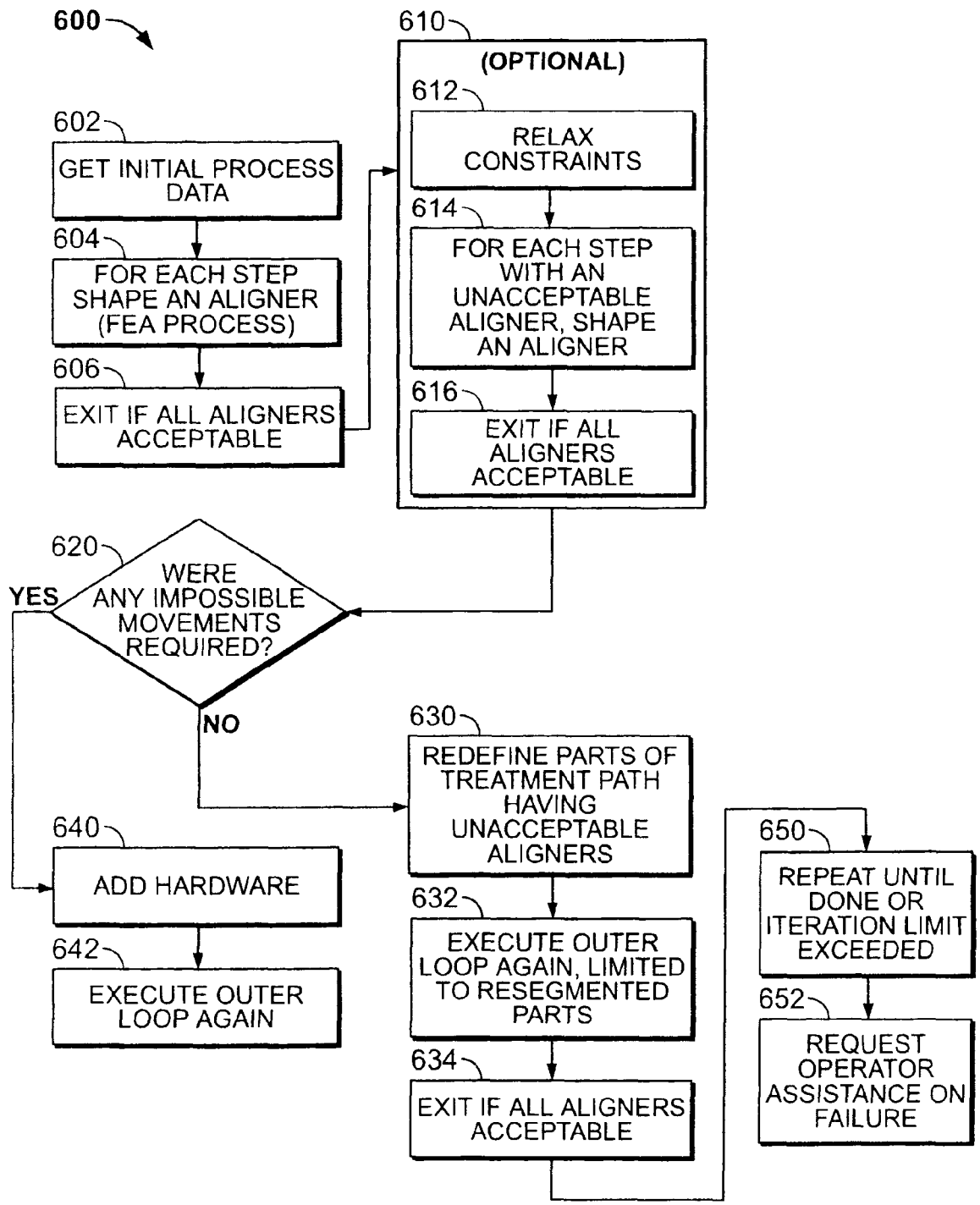
FIG. 6 is a flowchart of a process for computing shapes for sets of aligners.

As shown in FIG. 6, the process 200 (FIG. 2B) of computing the shape for an aligner for a step in a treatment path is one step in a process 600 of computing the shapes of a series of aligners. This process 600 begins with an initialization step 602 in which initial data, control and constraint values are obtained.

When an aligner configuration has been found for each step or segment of the treatment path (step 604), the process 600 determines whether all of the aligners are acceptable (step 606). If they are, the process is complete. Otherwise, the process optionally undertakes a set of steps 610 in an attempt to calculate a set of acceptable aligners. First, one or more of the constraints on the aligners is relaxed (step 612). Then, for each path segment with an unacceptable aligner, the process 200 (FIG. 2B) of shaping an aligner is performed with the new constraints (step 614). If all the aligners are now acceptable, the process 600 exits (step 616).

Aligners may be unacceptable for a variety of reasons, some of which are handled by the process. For example, if any impossible movements were required (decision step 620), that is, if the shape calculation process 200 (FIG. 2B) was required to effect a motion for which no rule or adjustment was available, the process 600 proceeds to execute a module that calculates the configuration of a hardware attachment to the subject tooth to which forces can be applied to effect the required motion (step 640). Because adding hardware can have an effect that is more than local, when hardware is added to the model, the outer loop of the process 600 is executed again (step 642).

If no impossible movements were required ("no" branch from step 620), the process transfers control to a path definition process (such as step 150, FIG. 2A) to redefine those parts of the treatment path having unacceptable aligners (step 630). This step can include both changing the increments of tooth motion, i.e., changing the segmentation, on the treatment path, changing the path followed by one or more teeth in the treatment path, or both. After the treatment path has been redefined, the outer loop of the process is executed again (step 632). The recalculation is advantageously limited to recalculating only those aligners on the redefined portions of the treatment path. If all the aligners are now acceptable, the process exits (step 634). If unacceptable aligners still remain, the process can be repeated until an acceptable set of aligners is found or an iteration limit is exceeded (step 650). At this point, as well as at other points in the processes that are described in this specification, such as at the computation of additional hardware (step 640), the process can interact with a human operator, such as a clinician or technician, to request assistance (step 652). Assistance that an operator provides can include defining or selecting suitable attachments to be attached to a tooth or a bone, defining an added elastic element to provide a needed force for one or more segments of the treatment path, suggesting an alteration to the treatment path, either in the motion path of a tooth or in the segmentation of the treatment path, and approving a deviation from or relaxation of an operative constraint.

As was mentioned above, the process 600 is defined and parameterized by various items of input data (step 602). In one implementation, this initializing and defining data includes the following items: an iteration limit for the outer loop of the overall process; specification of figures of merit that are calculated to determine whether an aligner is good enough (see FIG. 2B, step 270); a specification of the aligner material; a specification of the constraints that the shape or configuration of an aligner must satisfy to be acceptable; a specification of the forces and positioning motions and velocities that are orthodontically acceptable; an initial treatment path, which includes the motion path for each tooth and a segmentation of the treatment path into segments, each segment to be accomplished by one aligner; a specification of the shapes and positions of any anchors installed on the teeth or otherwise; and a specification of a model for the jaw bone and other tissues in or on which the teeth are situated (in the implementation being described, this model consists of a model of a viscous substrate fluid in which the teeth are embedded and which has boundary conditions that essentially define a container for the fluid).

Figure 7:
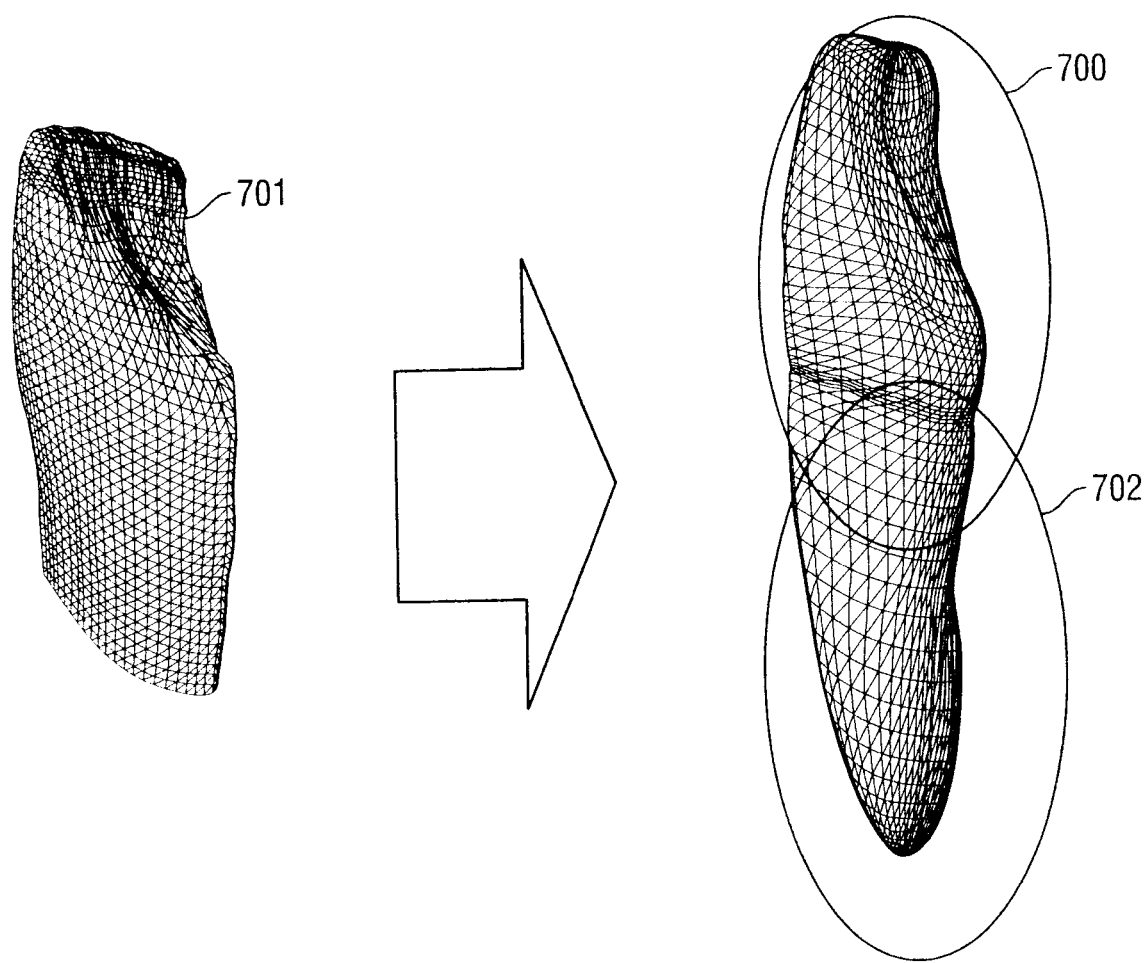
FIG. 7 is an exemplary diagram of a statistical root model.

FIG. 7 is an exemplary diagram of a statistical root model. As shown therein, using the scanning processes described above, a scanned upper portion 701 of a tooth is identified. The scanned upper portion, including the crown, is then supplemented with a modeled 3D root. The 3D model of the root can be statistically modeled. The 3D model of the root 702 and the 3D model of the upper portion 700 together form a complete 3D model of a tooth.

Figure 8:
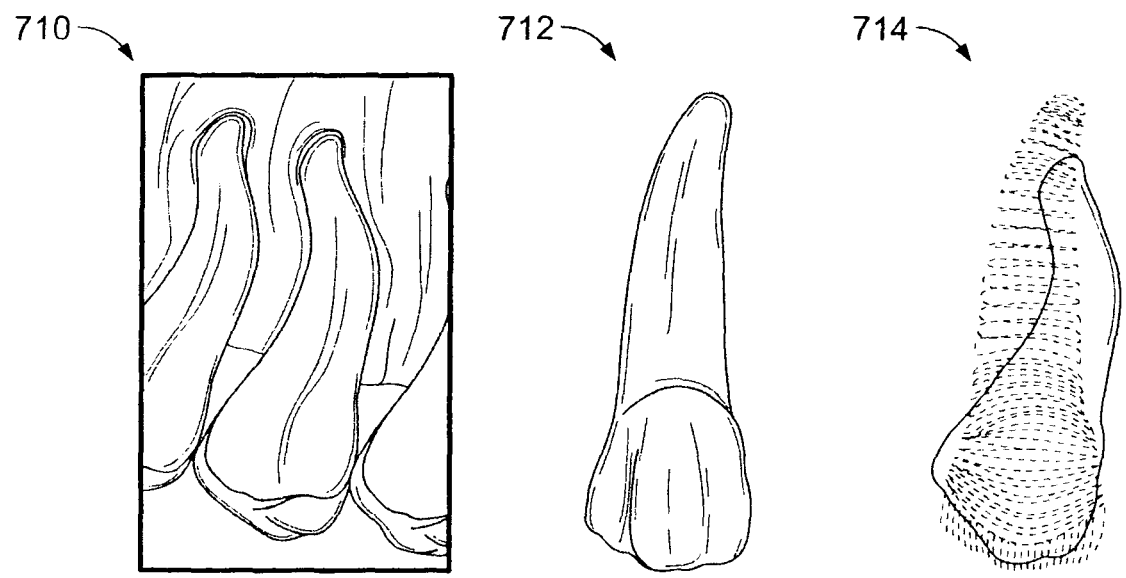
FIG. 8 shows exemplary diagrams of root modeling.

FIG. 8 shows exemplary diagrams of root modeling, as enhanced using additional dental information. In FIG. 8, the additional dental information is X-ray information. An X-ray image 710 of teeth is scanned to provide a 2D view of the complete tooth shapes. An outline of a target tooth is identified in the X-Ray image. The model 712 as developed in FIG. 7 is modified in accordance with the additional information. In one embodiment, the tooth model of FIG. 7 is morphed to form a new model 714 that conforms with the X-ray data.

Figure 9:
FIG. 9 show exemplary diagrams of CT scan of teeth.

FIG. 9 shows an exemplary diagram of a CT scan of teeth. In this embodiment, the roots are derived directly from a high-resolution CBCT scan of the patient. Scanned roots can then be applied to crowns derived from an impression, or used with the existing crowns extracted from Cone Beam Computed Tomography (CBCT) data. A CBCT single scan gives 3D data and multiple forms of X-ray-like data. PVS impressions are avoided.

In one embodiment, a cone beam x-ray source and a 2D area detector scans the patient's dental anatomy, preferably over a 360 degree angular range and along its entire length, by any one of various methods wherein the position of the area detector is fixed relative to the source, and relative rotational and translational movement between the source and object provides the scanning (irradiation of the object by radiation energy). As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

Figure 10:
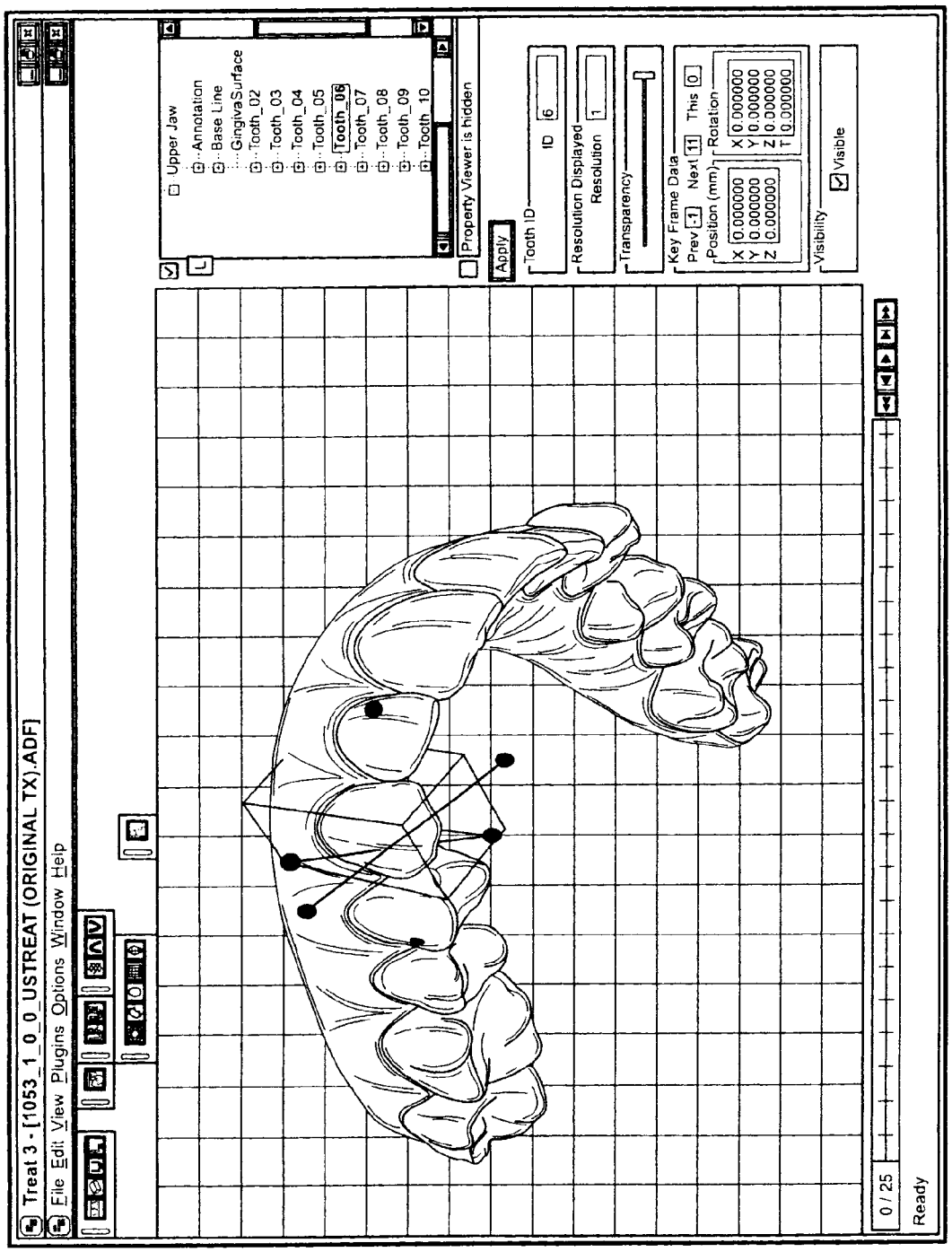
FIG. 10 shows an exemplary user interface showing teeth.

FIG. 10 shows an exemplary user interface showing the erupted teeth, which can be shown with root information in another embodiment. Each tooth is individually adjustable using a suitable handle. In the embodiment of FIG. 10, the handle allows an operator to move the tooth in three-dimensions with six degrees of freedom.

The teeth movement is guided in part using a root-based sequencing system. In one embodiment, the movement is constrained by a surface area constraint, while in another embodiment, the movement is constrained by a volume constraint.

In one embodiment, the system determines a surface area for each tooth model. The system then sums all surface areas for all tooth models to be moved. Next, the system sums all surface areas of all tooth models on the arch. For each stage of teeth movement, the system checks that a predetermined area ratio or constraint is met while the tooth models are moved. In one implementation, the constraint can be to ensure that the surface areas of moving teeth are less than the total surface areas of teeth on an arch supporting the teeth being moved. If the ratio is greater than a particular number such as 50%, the system indicates an error signal to an operator to indicate that the teeth should be moved on a slower basis.

In another embodiment, the system determines the volume for each tooth model. The system then sums the volumes for all tooth models being moved. Next, the system determines the total volume of all tooth models on the arch. For each stage of teeth movement, the system checks that a predetermined volume ratio or constraint is met while the tooth models are moved. In one implementation, the constraint can be to ensure that the volume for moving teeth is less than the volume of all teeth on an arch supporting the teeth being moved. If the ratio is greater than a particular number such as 50%, the system indicates an error signal to an operator to indicate that the teeth should be moved on a slower basis.

Optionally, other features are added to the tooth model data sets to produce desired features in the aligners. For example, it may be desirable to add digital wax patches to define cavities or recesses to maintain a space between the aligner and particular regions of the teeth or jaw. It may also be desirable to add digital wax patches to define corrugated or other structural forms to create regions having particular stiffness or other structural properties. In manufacturing processes that rely on generation of positive models to produce the repositioning appliance, adding a wax patch to the digital model will generate a positive mold that has the same added wax patch geometry. This can be done globally in defining the base shape of the aligners or in the calculation of particular aligner shapes. One feature that can be added is a rim around the gumline, which can be produced by adding a digital model wire at the gumline of the digital model teeth from which the aligner is manufactured. When an aligner is manufactured by pressure fitting polymeric material over a positive physical model of the digital teeth, the wire along the gumlines causes the aligner to have a rim around it providing additional stiffness along the gumline.

In another optional manufacturing technique, two sheets of material are pressure fit over the positive tooth model, where one of the sheets is cut along the apex arch of the aligner and the other is overlaid on top. This provides a double thickness of aligner material along the vertical walls of the teeth.

The changes that can be made to the design of an aligner are constrained by the manufacturing technique that will be used to produce it. For example, if the aligner will be made by pressure fitting a polymeric sheet over a positive model, the thickness of the aligner is determined by the thickness of the sheet. As a consequence, the system will generally adjust the performance of the aligner by changing the orientation of the model teeth, the sizes of parts of the model teeth, the position and selection of attachments, and the addition or removal of material (e.g., adding wires or creating dimples) to change the structure of the aligner. The system can optionally adjust the aligner by specifying that one or more of the aligners are to be made of a sheet of a thickness other than the standard one, to provide more or less force to the teeth. On the other hand, if the aligner will be made by a stereo lithography process, the thickness of the aligner can be varied locally, and structural features such as rims, dimples, and corrugations can be added without modifying the digital model of the teeth.

The system can also be used to model the effects of more traditional appliances such as retainers and braces and therefore be used to generate optimal designs and treatment programs for particular patients.

Figure 11:
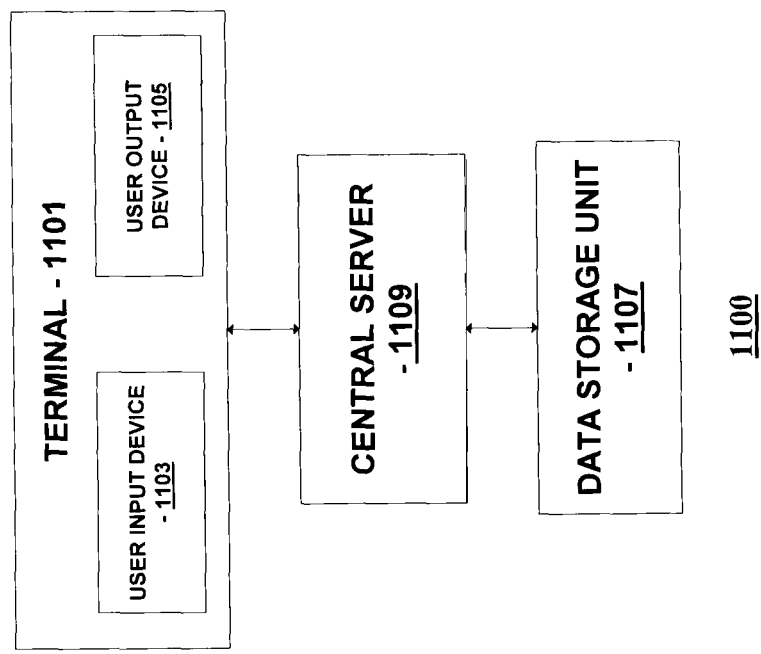
FIG. 11 is a block diagram of the overall system for practicing the various embodiments of the present invention.

FIG. 11 is a block diagram of the overall indexing system 1100 for practicing the various embodiments of the present invention. The indexing system 1100 in one embodiment includes a terminal 1101, which may be configured as a personal computer, workstation, or mainframe, and which includes a user interface input device 1103 and a user interface output device 1105, a storage unit 1107, and a central server 1109.

Referring to FIG. 11, the user interface input device 1103 may include a keyboard and may further include a pointing devices and/or a scanner, including x-ray or intra-oral scanner. The pointing device may be an indirect pointing device such as a mouse, trackball, touchpad, or graphics tablet, or a direct pointing device such as a touchscreen incorporated into the user interface output device 1105. Other types of user interface input devices, such as voice recognition systems, may be used within the scope of the present invention.

Referring again to FIG. 11, the user interface output device 1105 may include a printer and a display subsystem, which includes a display controller and a display device coupled to the controller. The display device may be a cathode ray tube (CRT), a flat-panel device such as a liquid crystal display, or a projection device. The display subsystem may also provide nonvisual display such as audio output.

The indexing system 1100 shown in FIG. 11 also includes the data storage unit 1107 which is configured to, under the access and control of either a central server 1109 or a client application, to maintain the basic programming and data constructs that provide the functionality of the present invention. Software is stored in storage unit 1107 which may include a memory unit and file storage unit. The memory unit may include a main random access memory (RAM) for storage of instructions and data during program execution and a read-only memory (ROM) in which fixed instructions are stored.

The file storage unit of the data storage unit 1107 may provide persistent (nonvolatile) storage for program and data files, and typically includes at least one hard disk drive and at least one CD-ROM drive (with associated removable media). There may also be other devices such as a floppy disk drive and optical drives (all with their associated removable media). Additionally, the file storage unit may include drives of the type with removable media cartridges, such as hard disk cartridges and flexible disk cartridges. One or more of the drives may be located at a remote location, such as in central server 1109 on a local area network or at a site on the Internet's World Wide Web or the entire system may be a stand-alone software application resident on the user's system.

In one aspect of the present invention, the central server 1109 may be configured to communicate with the terminal 1101 and data storage unit 1107 to access software stored in the data storage unit 1107 based on and in response to the input received from terminal 1101, and to perform additional processing based on procedures and/or routines in accordance with the instructions or input information received from the terminal 1101.

Referring back to FIG. 11, the indexing system 1100 in accordance with one embodiment of the present invention organizes orthodontic needs by the most common configurations of orthodontic discrepancies in the different dimensions: sagittal, vertical, horizontal/transverse, and arch length. The categories may be expanded to specifically capture other components such as facial profile, individual dental configurations, dynamic functional relationships, and surrounding soft tissue conditions; however, discrepancies in these four categories capture a significant portion of orthodontic related dental problems or concerns. Within each category, there may be a predetermined number of individual components to characterize the potential conditions for that dimension. For each condition, a predetermined combination of different possible conditions may be created. This collection of predefined combinations for each component, where each component belongs to one of the four main categories described, in one embodiment defines a matrix such that any patient at any time point may be defined as a specific address within the matrix. Both the matrix and address matrix may be stored in storage unit 1107.

FIG. 12 illustrates an exemplary tabular representation of the indexing system matrix stored in the storage unit 1107 of FIG. 11 in accordance with one embodiment of the present invention. The exemplary table 1200 of FIG. 12 illustrates a simplified version of the possible conditions for one component within each of the four categories.

Referring to FIG. 12, the table 1200 includes a category field 1201, a reference component field 1202, and the pre-defined options field 1203. Table 1200 also includes a number of options field 1204. The category field 1201 in one embodiment includes the categories for which reference dentition condition information is stored. In the exemplary embodiment, the categories may include: sagittal, vertical, horizontal, and arch length. In this exemplary embodiment, the reference component field 1202 includes one common component within each dimension by which malocclusion is judged. The common pre-defined options field 1203 includes the various levels of malocclusion for that dimension of the category. For example, the common malocclusions for the right canine component of the sagittal category are: Full class 2+(greater than full cusp Class 2), Full (Cusp) Class 2, Partial Class 2 (also called end-on Class 2), and so on. Within each dimensional component selection is also a selection for "normal."

Referring to FIG. 12, the number of options field 1204 in one embodiment includes the number of possible reference conditions in each category, and also a total number of possible combinations of reference conditions. For example, the sagittal category has seven (7) possible reference conditions for the canine relationship component and the vertical category has seven (7) reference conditions for the anterior overbite component. The example shown yields 7×7×7×7=2401 possible combinations of reference conditions for the four components, as shown in table 1200 of FIG. 12. In one embodiment, each of these 2,401 patient case combinations is stored in a database in storage unit 1107 (FIG. 11), for example, by the central server 1109. Since there can be numerous components used to describe each of the four main orthodontic dimensions and not just one component per dimension as illustrated, in practice, the total number of combinations that can be used to describe a patient may be substantially higher, but at the same time, will be a finite number such that it may be indexed, catalogued, and queried as described in FIG. 11.

In reference to the index table 1200 illustrated in FIG. 12, an identifier may be composed of a four-position, or "four-bit" matrix: ABCD. In this four-bit matrix, in one embodiment of the present invention, the "A" position in the matrix corresponds to the sagittal dimension, the "B" position in the matrix corresponds to the vertical dimension, the "C" position in the matrix corresponds to the horizontal dimension, and the "D" position in the matrix corresponds to the arch length dimension.

The actual number or letter in the position of each "bit" of the matrix may be associated with the corresponding condition within the category. For example, referring again to the exemplary table 1200 of FIG. 12, an identifier of 3256 represents: a right canine partial Class 2, with moderate anterior deep bite, upper midline to the left 0-1 mm, and lower moderate crowding. This "3256" identifier corresponds to an address in an indexing database stored in storage unit 1107 which has stored in the database, related clinical information for the particular pairing of "3256" to a user-defined treatment goal (for example, discussed in further detail below with reference to FIG. 14).

Dental Characterization Database

Referring back to FIG. 11, the indexing system 1100 in one embodiment of the present invention may also be used to represent one or more teeth within a patient's dentition. Typically an adult patient's dentition includes 32 teeth. Dentists usually characterize five surfaces of each tooth: mesial, occlusal/incisal, distal, buccal/facial, and lingual. Each of these surfaces may be natural or covered by a restoration such as silver amalgam, composite, porcelain, gold, or metal crown. The tooth may also be missing or have been treated with a root canal or an implant. These combinations may be represented with an indexing system for the initial dentition, target dentition (treatment goal), and final dentition which is the outcome of the treatment.

For each tooth in a patient's dentition, there may be a number of possible conditions based on the characteristics of the tooth, such as the surface of the tooth and whether the tooth as been treated or is missing. The combinations of different possible conditions of the teeth define a matrix. An exemplary embodiment of the present invention includes a 32-position address within the matrix, where each position in the address corresponds to a tooth in a patient's dentition and includes a sub-address in which alphanumeric characters or other representations represent the current condition of the tooth.

A "5-bit" sub-address for each tooth includes positions 12345 where each of the positions "1" to "5" represents one of the five surfaces of the tooth. In particular, position 1 of the sub-address corresponds to the mesial surface of the tooth, position 2 of the sub-address corresponds to the occlusal or incisal surface of the tooth, position 3 of the sub-address corresponds to the distal surface of the tooth, position 4 of the sub-address corresponds to buccal or facial surface of the tooth, and position 5 of the sub-address corresponds to the lingual surface of the tooth.

Moreover, each of the following characters "A" to "N" corresponds to a condition of the particular surface of the tooth in the sub-address.

A = amalgam
B = composite
C = porcelain veneer
D = gold
E = porcelain crown
F = gold crown
G = gold crown with root canal
H = porcelain crown with root canal
I = amalgam with root canal
J = composite with root canal
K = gold crown with implant -continued L = porcelain crown with implant
M = missing
N = natural For example, consider the following patient identifier 1:NNABN. The identifier 1:NNABN would represent: tooth number 1 of a 32-bit address which has a natural mesial surface (subaddress position 1), an occlusal amalgam (subaddress position 2), a natural distal surface (subaddress position 3), a buccal/facial composite (subaddress position 4), and a natural lingual surface (subaddress position 5).

In an exemplary embodiment of patient's initial dentition, target dentition (treatment goal), and final dentition, such example may be configured as:

TotalAddress=SubAddress1:SubAddress2:SubAddress3

SubAddress1=Teeth 1-32 initial
SubAddress2=Teeth 1-32 target
SubAddress3=Teeth 1-32 current, timepoint today whereby each of the of the 1-32 may further include an addition sub-matrix of 1-5 surfaces as previously described.

In this manner, dentists may easily query their practice database to determine how much dental work has been done and remains to be done. They can also track trends of use in their practice and what are the most common procedures in the practice. The patient matrix may also be used in forensics for patient identification purposes, as well as for national security and other security purposes.

FIG. 13 illustrates an exemplary tabulation of the possible treatment goals of the indexing system treatment goal matrix stored in the storage unit 1107 of FIG. 11 in accordance with one embodiment of the present invention. Four examples of treatment goals are the following:

Treatment Goal 1: Pre-restorative set-up—the objective of this goal is to better position specific teeth for the purpose of improved placement of dental restorations such as crowns, bridges, and implants. Some of the patient's dental components may be left as is (untreated) if they do not contribute to the purpose of improvement of the restorative goal.

Treatment Goal 2: Esthetic alignment—the objective of this goal is to align the patient's anterior teeth for the purpose of improved esthetics. Generally speaking, the patient's bite may be left as is (untreated) if it does not contribute to the purpose of improving the esthetic component of the patient's smile.

Treatment Goal 3: Anterior function improvement—the objective of this goal is to improve the anterior function of the teeth while also improving the anterior esthetic component. Generally speaking, the patient's posterior occlusion may be left as is if it does not contribute to the improvement of the canine function and/or anterior esthetics.

Treatment Goal 4: Optimal set-up—the objective of this goal is to make the entire bite close to "textbook" ideal, including both the canine and molar function.

Figures 14, 15:
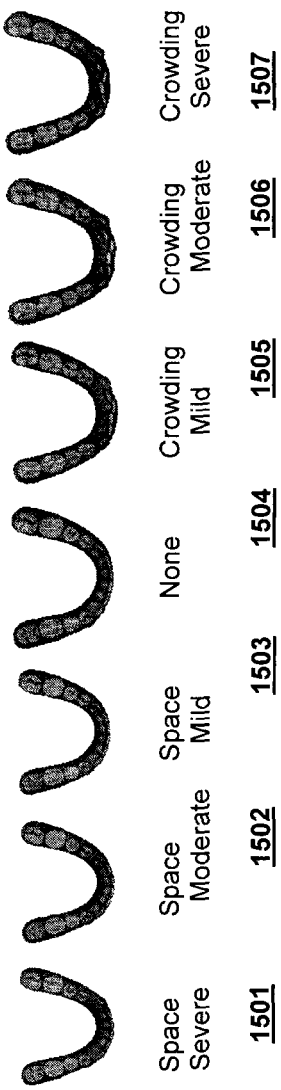
FIG. 14 illustrates a matrix representation for the possible treatment goals shown in FIG. 13 formatted in accordance with the tabular representation shown in FIG. 12 in accordance with one embodiment of the present invention.
FIG. 15 illustrates the lower arch length category for use in the indexing system in accordance with one embodiment of the present invention.

FIG. 14 illustrates an expanded version of FIG. 13 using the characteristics as defined by the tabulation shown in FIG. 12. More specifically, each of the four treatment goals identified in FIG. 13 may be further refined and formatted according to the tabulation and indexing shown in FIG. 12 to describe the target objective of treatment in greater detail according to each individual component.

For example, for the treatment goal 1 for pre-restorative set-up, an example of this goal according to the 4-bit matrix format in FIG. 12 may be XXX4 where the "X" is the patient's existing relationship for that component left untreated, and only the fourth digit is planned for treatment. Furthermore, for the treatment goal 2 for esthetic alignment, an example of this goal according to the 4-bit matrix format in FIG. 2 may be XX44 where "X" is the patient's existing relationship for that component left untreated, and only the third and fourth digits (representing the transverse and arch length components, respectively) are planned for treatment.

In addition, for treatment goal 3 for anterior function improvement, an example of this goal according to the 4-bit matrix format in FIG. 12 may be 4×44 whereby "X" is the patient's existing relationship for that component left untreated. In this example, only the second digit component (corresponding to the vertical dimension) is not planned for treatment. Finally, for treatment goal 4 for optimal set-up, an example of this goal according to the 4-bit matrix defined in FIG. 12, may be 4444.

There are various ways to generate an identifier which represents a patient's unique problem or case type. Traditionally, the method has been to describe and define a characteristic and have the trained individual subjectively identify the condition or "label" which best represents the patient's condition. To reduce the variability in this method requires calibration and/or objective measures to define each of the labels.

Another method involves using a visual image-based interface. To characterize a patient's dentition, a user compares the patient's dentition to images of reference dentition conditions which depict the severity of malocclusion, or lack thereof. The user then identifies where the patient's dentition condition falls within a range of reference conditions depicting malocclusion and selects the image that either best represents the patient, or selects a relative position of the patient's condition from a continuous gradient of patient image depictions of the specific problem. The visual image interface can be presented to the user without any descriptions or labels to avoid any pre-conceived biases associated with the label.

Visual images have been previously described in the ICON indexing system for example, to describe an esthetic component of the patient. In the ICON system, the assessor selects 1 of 10 images which best represents the patient's anterior esthetic component. Through calibration, multiple users are then able to determine a patient's esthetic component with reasonable consistency. The use of a visual interface to capture every component of the patient's orthodontic dental condition however, has not previously been described as an interface for creation of a digital patient database.

FIG. 15 illustrates the lower arch length component 1500 for use in the indexing system in accordance with one embodiment of the present invention. This illustration of the lower arch length component 1500 is an exemplary visual scale allowing the user to select an image which is similar to the patient's dentition condition. Referring to FIG. 5, there are shown seven images of the lower arch, each representing a possible reference condition for the lower arch length category. In this exemplary embodiment, images 1501-1507 represents the 7 images corresponding to the individual fields for the "Lower Arch Length" component of "Arch Length" dimension of FIG. 12. The user simply selects which of the seven images is best represented in the patient. Or they may be able to select where in between two adjacent images the patient can be best described. They do not need to know what the technical label or term is; they simply need to select an image or area between two images based on direct comparison of the existing condition to the pictures presented.

In the exemplary embodiment shown in FIG. 15, each of the seven images 1501-1507 has a corresponding predefined alphanumeric character. Thus, when an image is selected, the associated predefined alphanumeric character is added to the identifier address of the patient. By labeling each category with an alphanumeric character, the patient's dentition may be characterized through alphanumeric addressing. The output to the user may explain the specific details of their selection in greater detail, including the technical description and treatment options associated with such a condition. In an alternate embodiment, an alphanumeric character may be generated when the user selects the area in between adjacent images, representing that the patient's condition falls in between the condition of the adjacent images selected. The user interface may also be a combination of both direct selection of the image as well as in-between selection of images.

Referring now to FIG. 16, an exemplary doctor and patient information display 1600 for the indexing system 1100 is illustrated in accordance with one embodiment of the present invention. This display 600 includes information input by a user into fields 1601-1603 to identify a patient. In particular, a patient's name is input into field 1601, a patient's gender is input into field 1602, and a patient's primary concern(s) is input into field 1603. The preferred embodiment of field 1603 is a check-box selection of pre-defined possible conditions which can then be catalogued according to the selections of the user. It will be appreciated that other patient information may be added. Once the patient information has been entered, a user can select a predefined input command or button to move onto the next display, which is illustrated in FIG. 17.

Figure 17:
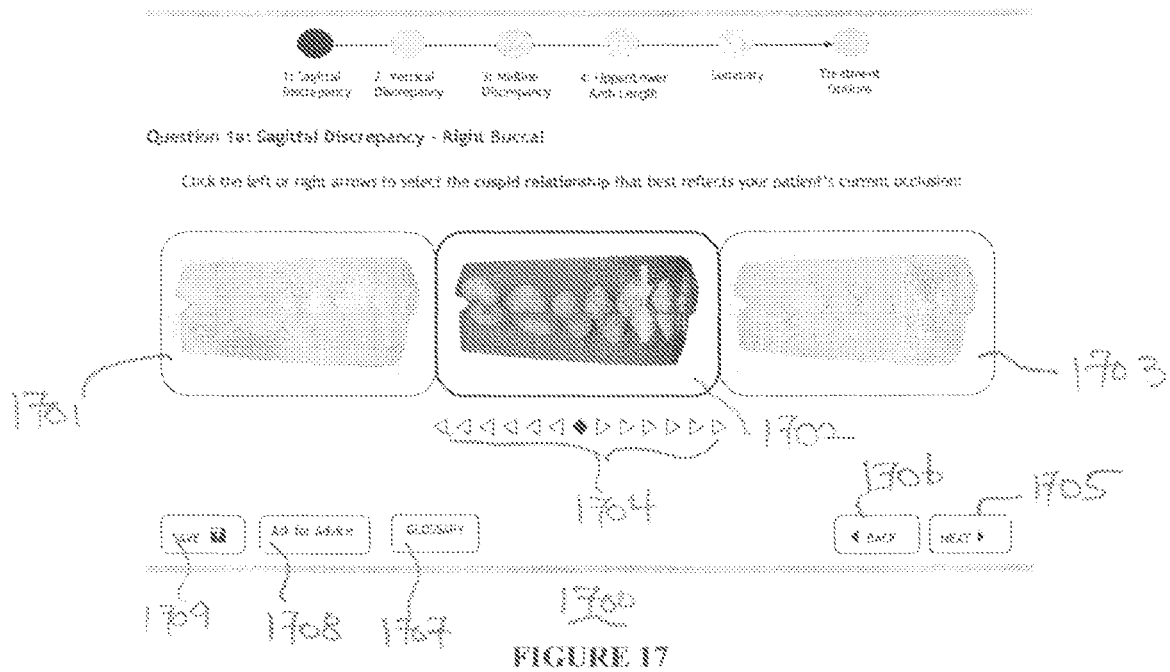
FIG. 17 illustrates an exemplary selection process display 1700 for capturing one component of the sagittal dimension discrepancy for the patient's right side in one embodiment of the present invention.

Referring to FIG. 17, an exemplary selection process display 1700 is shown for the sagittal dimension (matrix address position "A" in FIG. 12)—right buccal, right canine/cuspid component. A series of images of reference dentition conditions 1701-1703 are displayed in conjunction with buttons 1704 allowing the images to be scrolled to the left or right. A user clicks the left or right arrow buttons 1704 to select the image of the reference dentition condition that best reflects the patient's current condition specifically at the location(s) indicated by the focusing arrows indicated in 1702. In this exemplary embodiment, a user clicks the left or right arrow buttons to select the cuspid (canine) relationship that is similar to a patient's current occlusion.

Once the selection is made, the next button 1705 is pressed to move onto the next screen. The exemplary selection process display 1700 also includes buttons 1706-1709 to allow a user to go back, access a glossary, ask for advice, and save the information, respectively.

Figure 18:
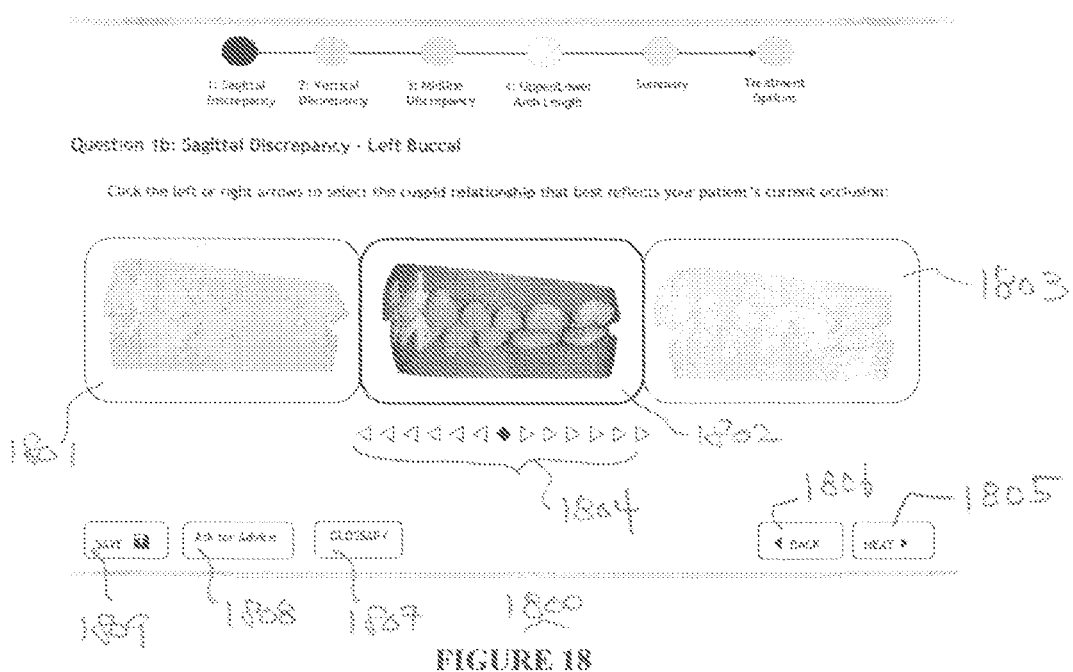
FIG. 18 illustrates an exemplary selection process display 1700 for capturing one component of the sagittal dimension discrepancy for the patient's left side in one embodiment of the present invention.

Referring to FIG. 18, an exemplary selection process display 1800 is shown for the sagittal category—left buccal, left cuspid component. A series of images of reference dentition conditions 1801-1803 are displayed in association with buttons 804 allowing the images to be scrolled to the left or right. A user clicks the left or right arrow buttons 804 to select the image of the reference dentition condition that best reflects the patient's current condition. In this exemplary embodiment, a user clicks the left or right arrow buttons to select the cuspid relationship that is similar to a patient's current occlusion.

Figure 19:
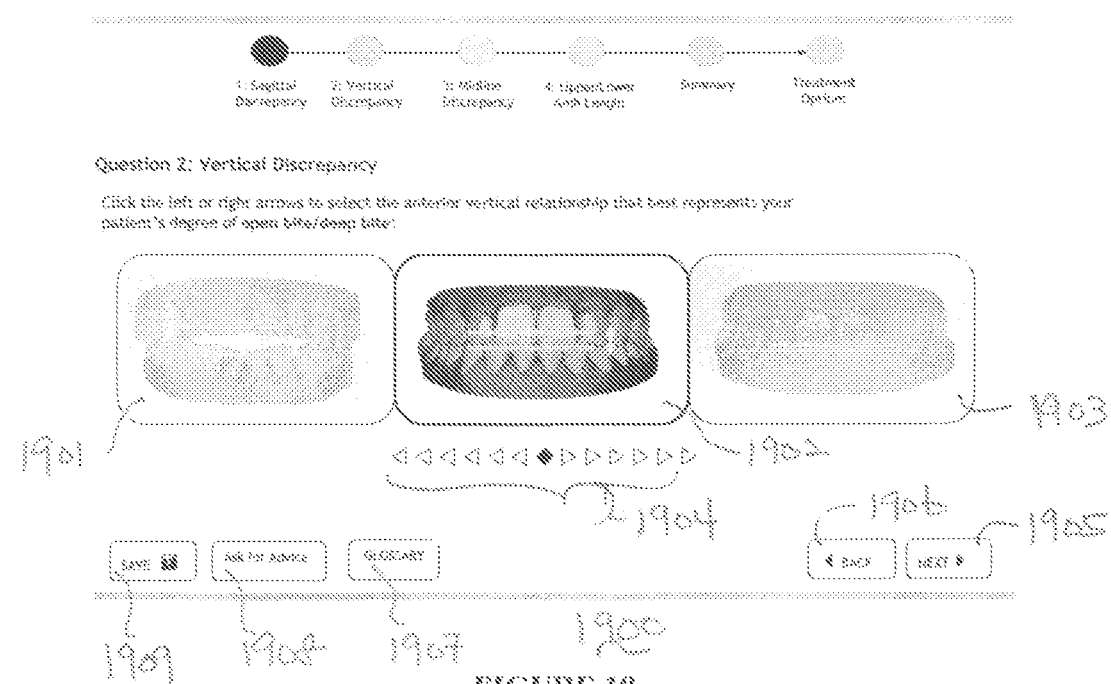
FIG. 19 illustrates an exemplary selection process display 1900 for capturing one component of the vertical dimension in one embodiment of the present invention.

Once the selection is made, the next button 1805 is pressed to move onto the next display which is illustrated in FIG. 19. The exemplary selection process display 1800 also includes buttons 1806-1809 to allow a user to go back, access a glossary, ask for advice, and save the information, respectively.

Referring to FIG. 19, an exemplary selection process display 1900 is shown for the vertical dimension (matrix address position "B" in FIG. 12)—anterior overbite component. A series of images of reference conditions 1901-1903 are displayed in conjunction with buttons 1904 allowing the images to be scrolled to the left or right. A user clicks the left or right arrow buttons 1904 to select the image of the reference dentition condition that best reflects the patient's current condition. In this exemplary embodiment, a user clicks the left or right arrow buttons 1904 to select the anterior vertical overbite relationship component that is similar to a patient's degree of open or deep bite.

Figure 20:
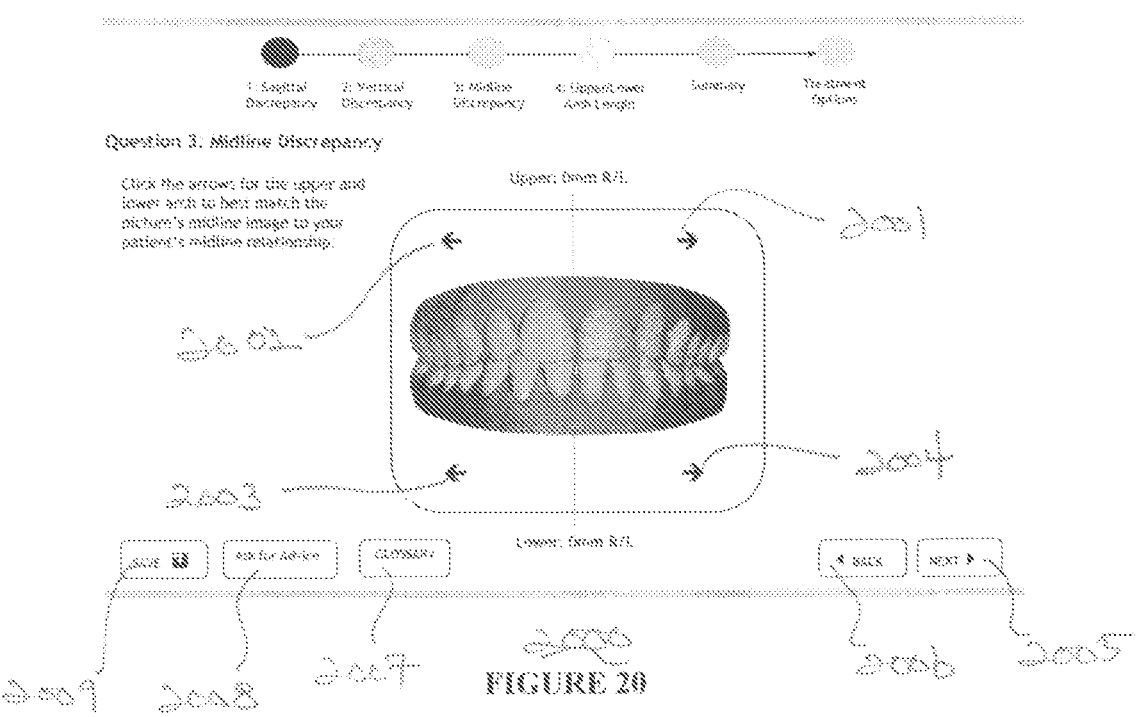
FIG. 20 illustrates an exemplary selection process display 2000 for capturing one component of the horizontal/transverse dimension in one embodiment of the present invention.

Once the selection is made, the next button 1905 is pressed to move onto the next display, which is illustrated in FIG. 20. The exemplary selection process display 1900 also includes buttons 1906-1909 to allow a user to go back, access a glossary, ask for advice, and save the information, respectively.

Figure 21:
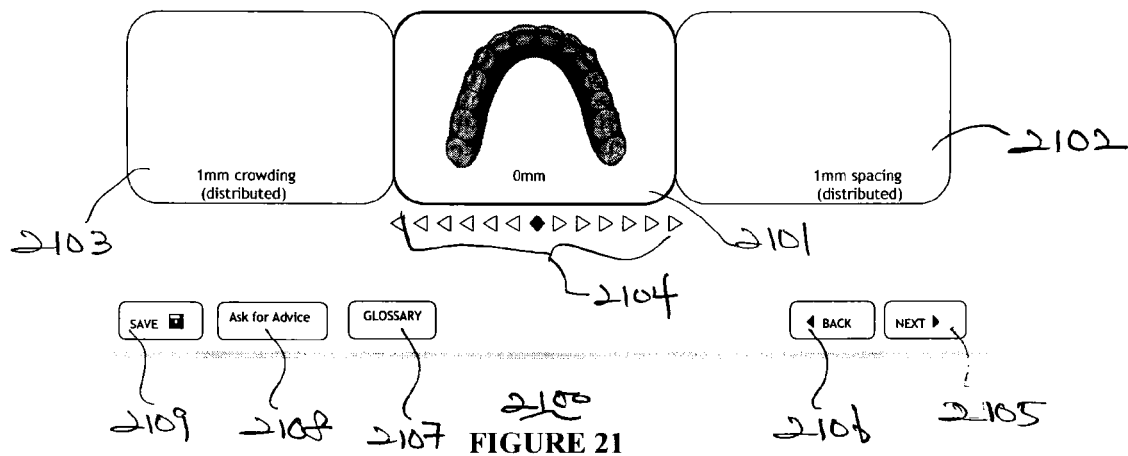
FIG. 21, an exemplary selection process display 2100 for capturing one component of the arch length discrepancy category in accordance with one embodiment of the present invention.

Referring to FIG. 20, an exemplary selection process display 2000 is shown for the horizontal/transverse dimension (matrix address position "C" in FIG. 12)—upper and lower midline components. An image 1010 representing a reference dentition condition is altered by clicking the upper arrows 2001-2002 corresponding to the upper arch of the image 2010, and by clicking the lower arrows 2003-2004 corresponding to the lower arch of the image 1010 to best match the midline of the image 2010 to a patient's midline component relationship. Once the selection is made, the next button 2005 is pressed to move onto the next display, which is illustrated in FIG. 21. The exemplary selection process display 2000 of FIG. 20 also includes buttons 2006-2009 to allow a user to go back, access a glossary, ask for advice, and save the information, respectively.

Referring to FIG. 21, an exemplary selection process display 2100 is shown for the upper arch length category. An image of a reference dentition condition 2101 and descriptions of reference dentition conditions 2102, 2103 are displayed in association with buttons 2104 allowing the reference dentition condition image and descriptions to be scrolled to the left or right. A user clicks the left or right arrow buttons 2104 to select the image or description of the reference dentition condition that best reflects the patient's current condition. In this exemplary embodiment, a user clicks the left or right arrow buttons 2104 to select the image or description of the reference dentition condition that is similar to a patient's upper arch length from the occlusal view. In this particular embodiment, if there is both crowding and spacing present, a user is instructed to use the net amount of crowding or spacing, but it may be possible to have each aspect captured independently.

Figure 22:
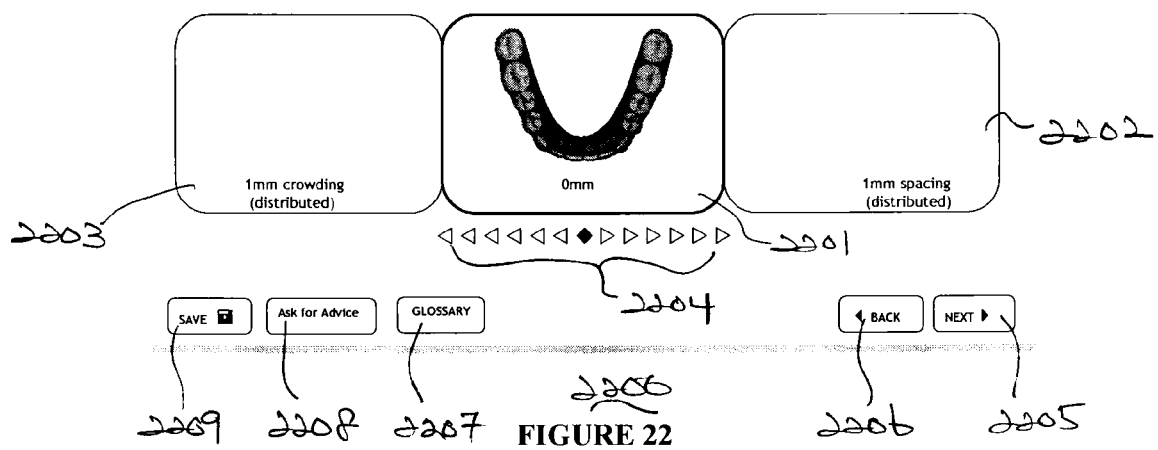
FIG. 22 illustrates an exemplary selection process display 2200 for capturing another component of the arch length discrepancy category in accordance with one embodiment of the present invention.

Again, once the selection is made, the next button 2105 is pressed to move onto the next display which is illustrated in FIG. 22. The exemplary selection process display 2100 also includes buttons 2106-2109 to allow a user to go back, access a glossary, ask for advice, and save the information, respectively.

Referring to FIG. 22, an exemplary selection process display 2200 is shown for the arch length dimension (matrix position "D" in FIG. 12)—lower arch length component. An image of a reference dentition condition 2201 and descriptions of reference dentition conditions 2202, 2203 are displayed in association with buttons 2204 allowing the reference dentition condition image and descriptions to be scrolled to the left or right. A user clicks the left or right arrow buttons 2204 to select the image or description of the reference dentition condition that best reflects the patient's current condition for the lower arch length component of arch length. In this exemplary embodiment, a user clicks the left or right arrow buttons 2204 to select the image or description of the reference dentition condition that is similar to a patient's lower arch length from the occlusal view. In this example, if both crowding and spacing are present, the user is instructed to use the net amount of crowding or spacing. It may be possible however to capture crowding and spacing independently in order to derive the net discrepancy.

Once the selection is made, the next button 2205 is pressed to move onto the next display, which is illustrated in FIG. 23. The exemplary selection process display 2200 of FIG. 22 also includes buttons 2206-2209 to allow a user to go back, access a glossary, ask for advice, and save the information, respectively.

FIG. 23 illustrates an exemplary patient summary tabulation 1300 for output display on terminal 1101 for use in the indexing system in accordance with one embodiment of the present invention. The exemplary patient summary display 2300 is generated from the information input from previous displays 1600-2200, as illustrated in corresponding FIGS. 16-22, respectively. Referring to FIG. 23, the selections made during the processes and displays described above and illustrated in conjunction with FIGS. 16-22 are summarized as shown in the summary display 2300 in one embodiment of the present invention.

For example, for each reference dentition category including sagittal, vertical, horizontal and arch length, the corresponding malocclusion reference component (for example, right canine, anterior overbite, upper midline relative to lower midline, and lower arch length, respectively), and each of which is associated with a selected one of the pre-defined options (for example, right canine partial Class 2, moderate anterior deep bite, upper midline to left 0-1 mm, and lower moderate crowding, respectively). Also can be seen from FIG. 23 is the selected value of the selected pre-defined options 1203 (FIG. 12) as tabulated and illustrated in FIG. 12. The user is also able to edit the dentition condition information in each of the categories by selecting the corresponding "EDIT" button to go back to the page desired and reselecting the image corresponding to that category.

In this manner, in one embodiment of the present invention, the information input by the user during the selection process is indexed and catalogued in a patient database (for example, the database 2400 shown in FIG. 24 below) of the indexing system 1100. In one embodiment of the present invention, the selection process discussed in conjunction with FIGS. 16-22 for the indexing and cataloguing is transparent to the user. The patient information input by the user in the selection process is used to generate both the summary display as illustrated in FIG. 23 and an identifier representing the dentition conditions of the patient. FIGS. 16-22 illustrate the selection process display 1600 for use in the indexing system 1100 for various categories in accordance with one embodiment of the present invention. This is the selection process for inputting a patient's dentition information. It will be appreciated that although FIGS. 17-22 illustrate reference dentition conditions represented by pictorial images, the present invention is not intended to be limited to such representations. The reference dentition conditions may also be represented by symbols, icons, descriptions, graphs, 3-D objects, radiographs, forms, and other types of images. The reference conditions may also be user-defined through an interactive graphical image such that the user best recreates the condition observed in the patient as a means of input for the system.

FIG. 24 illustrates a patient database 2400 for use in the indexing system 1100 in accordance with one embodiment of the present invention. The patient database 2400 includes a patient field 2401, an indexing database address field 2402, and one or more category fields 2403. In the exemplary database of FIG. 24, the category fields 2403 include a sagittal category field 2404, a vertical category field 2405, a horizontal category field 2406, an upper arch length category field 2407, a lower length category field 2408, a rotation field 2409, a vertical correction field 2410, and a midline correction field 2411.

Referring to FIG. 24, the patient field 2401 includes the patient name. The indexing database address field 2402 includes the patient identifier. This patient identifier corresponds to an address in the indexing database 1300, for example, as shown in FIG. 13. The address in the indexing database 1300 is associated with treatment information for that particular diagnostic combination. The category fields 2403, which in this exemplary embodiment are the sagittal category field 2404, the vertical category field 2405, the horizontal category field 2406, the upper arch length category field 2407, the lower length category field 2408, the rotation field 2409, the vertical correct field 2410, and the midline correct field 2411, include the patient's one or more dentition conditions in the respective categories. For example, referring to FIG. 24, patient L. Smith's dentition condition in the sagittal category field 2404 is "Class I". Patient M. Jones' dentition condition in the upper arch length category field 2407 is "normal". The category fields 2403 also indicate whether the particular reference condition is eligible for treatment (for example, shown by the Y/N indicator).

In this manner, the patient identifier may be configured to represent the patient conditions. For example, referring to the indexing database address field 2402, it is shown that L. Smith's identifier is "55772752". Since the identifier includes eight positions, the identifier is an eight-position matrix. The number in each position of the identifier represents a particular condition within a particular category. In this exemplary embodiment, the first position of the identifier matrix represents the patient condition in the sagittal category. For example, the sagittal category field 2404 indicates that L. Smith has a "Class I" malocclusion. Thus, the number 5 in the first position of the identifier represents a "Class I" malocclusion in the sagittal category.

Referring back to FIG. 24, the second position of the identifier matrix represents the patient condition in the vertical category. For example, the vertical category field 2405 indicates that L. Smith has normal occlusion. Thus, the number 5 in the second position of the identifier represents a normal occlusion in the vertical category. The third position of the identifier matrix represents the patient condition in the horizontal category. For example, the horizontal category field 2406 indicates that L. Smith has a crossbite. Thus, the number 7 in the third position of the identifier represents crossbite in the horizontal category.

Moreover, the fourth position of the identifier matrix represents the patient condition in the upper arch length category. For example, the upper arch length category field 2407 indicates that L. Smith has moderate crowding. Thus, the number 7 in the fourth position of the identifier represents moderate crowding in the upper arch length category. In addition, the fifth position of the identifier matrix represents the patient condition in the lower arch length category. For example, the lower arch length category field 2408 indicates that L. Smith has moderate spacing. Thus, the number 2 in the fifth position of the identifier represents moderate spacing in the lower arch length category.

In addition, the sixth position of the identifier matrix represents the patient condition in the rotation category. For example, the rotation category field 2409 indicates that L. Smith has <20° rotation. Thus, the number 7 in the sixth position of the identifier represents <20° rotation in the rotation category. Further, the seventh position of the identifier matrix represents the patient condition in the vertical correction category. For example, the vertical correct category field 2410 indicates that L. Smith has no extrusion. Thus, the number 5 in the seventh position of the identifier represents no intrusion/extraction in the vertical correction category.

Finally, referring yet again to FIG. 24, the eighth position of the identifier matrix represents the patient condition in the midline correct category. For example, the midline correct category field 2411 indicates that L. Smith has >2 mm midline correction. Thus, the number 2 in the eighth position of the identifier represents >2 mm midline correct in the midline correction category.

In this manner, in one embodiment of the present invention, the conditions in the categories may be arranged in a predetermined order each associated with a numerical (for example "the number 2 in the eight position of the identifier representing greater than 2 mm midline correction in the midline correction category for patient L. Smith), or a predefined identifier such as, alphanumeric characters, symbols and the like. In a further embodiment, the conditions in the categories may be arranged in ascending order by difficulty and the categories are sorted in order of difficulty so that it is possible to define a matrix where 11111111 represents the mildest case and 33333333 is the most severe case in an eight position matrix identifier, for example as described above. Additionally, each index in the matrix is weighted to derive a composite score of the overall case.

FIG. 25 illustrates an alternate embodiment of the present invention for capturing an address in the selection process for use in the indexing system. FIG. 25 illustrates the table 1200 of FIG. 12 used directly as a graphical interface. In such embodiment, each reference condition as shown and illustrated in tabular format as rectangles may be represented as user input buttons with text which may be clicked to highlight and select the appropriate reference condition. The assumption for this type of interface is that the user understands the definitions of the text in order to select the appropriate button. When the buttons are pressed to select a particular reference condition, the selections are highlighted (shown in bold in FIG. 25). Clicking any button twice will deselect the initial selection so that another selection can be made. In this manner, users who are more familiar with the various types of reference conditions may be able to input the information more quickly than through a visual-image based interface. In this example, the generated address would be "3256." The "Selected Value" column on the right side of FIG. 25 is in one embodiment, transparent to the user/patient, and not displayed to the user since the address has no relevance to the end user, and is important only for the database query.

FIG. 26 illustrates an exemplary series of database addresses generated by combining the initial condition address with the treatment goal address in one embodiment of the present invention. As indicated from the exemplary table 1200 of FIG. 12, there are 2,701 possible patient case combinations or addresses for four components of seven possible selection options each. Thus, an identifier address points to one of the 2,701 possible combinations in the database. Each identifier is associated with a field stored in a database of the storage unit 1107 (FIG. 11). An identifier may be extended so that it represents the patient's condition at different time points. For example, the database may be structured such that time points for initial dentition, target dentition, and actual final dentition are captured as separate addresses. For example, consider the following address:

ABCD: A*B*C*D*:ABCD

In this arrangement, the first four positions "A" to "D" of the matrix represent the patient's initial dentition (as previously described), positions "A*" to "D*" of the matrix represent the patient's target dentition or treatment goal, and positions "A" to "D" of the matrix represent the patient's actual final dentition or treatment outcome. Because the number of positions in the matrix may be variable, and since each position can include symbols, alphanumeric characters or other representations, the depth of individual patient cases that is stored is may be detailed and specific to the patient and/or the associated profile or condition. Using the 4 possible treatment outcomes illustrated in FIG. 14 and the 2,701 possible combinations in FIG. 12, this equates to 2,701× 4=10,804 possible paired combinations between initial and goal.

FIG. 27 illustrates an exemplary database for a patient with an index address of "3256" and the four possible treatment goals of 1 through 4. The resulting four combined addresses have different data for each of the parameters. This information is reported to the user either (1) upon completion of the case characterization, whereby all possible treatment goal options are presented to the user or (2) upon completion of the case characterization and selection of a single treatment goal, whereby only the information from this address-goal pair is presented to the user.

For each of these paired combinations, a combined address can be created, with database assets in a "digital mailbox" associated with each address. Assets for each digital mailbox can include, but is not limited to: treatment plan information related to the case-treatment goal pairing, such as a text description of the treatment condition and goals, treatment precautions, treatment length estimates, doctor skill set requirements, prescription data, sample case data, and case difficulty. This data may be generated using expert opinion, computational algorithms, and/or historical case content.

For example, with respect to FIG. 23, where the case is identified as a "3256" and using the 4 types of treatment goals as shown in FIG. 14, combining the two yields four distinct database addresses: 3256:1, 3256:2, 3256:3, and 3256:4. Each of the addresses can be populated with information specific to the case-treatment goal combination. All four options can be simultaneously displayed to the user as "treatment options" or the user can select a specific treatment goal and have a single specific resulting treatment option data displayed. It is also conceivable that the user may also select any number of specific goals, and each of the data associated with each goal selected is reported to the user depending on the initial condition parameters selected.

Figure 28:
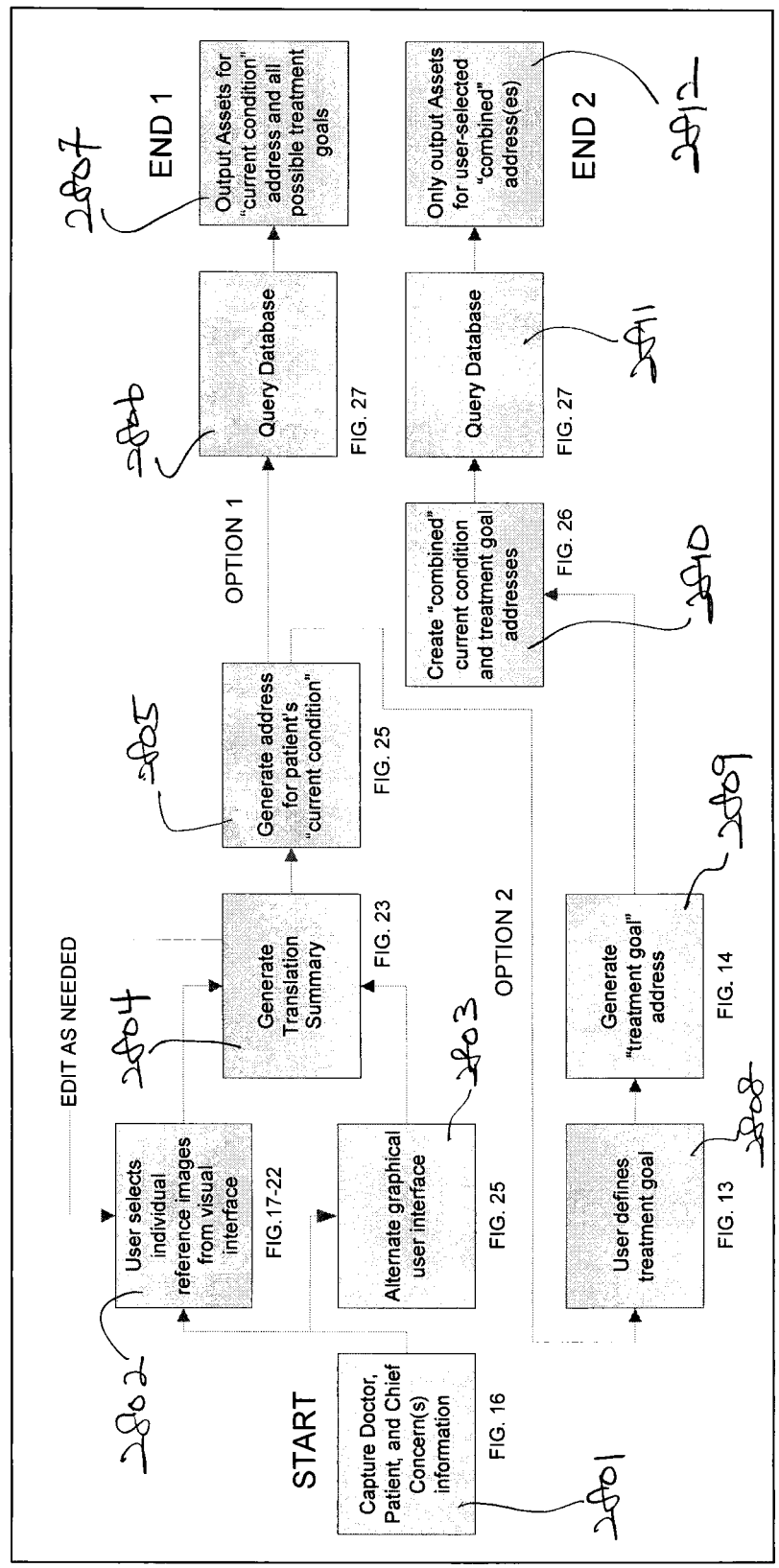
FIG. 28 is a flowchart illustrating the procedure for identifying a dentition profile using the indexing system in accordance with one embodiment of the present invention.

FIG. 28 illustrates a process 2800 for identifying a dentition problem or condition of a patient. The process 2800 is discussed more fully in conjunction with FIGS. 16-27. At step 2801, the user starts by entering identification information such as doctor and patient name, in addition to patient chief concern(s) (FIG. 16). In one embodiment, this comparison may be performed by the central server 1109 (FIG. 11) based on information received, for example, from the terminal 1101, and/or based on stored information retrieved from the data storage unit 1107. This and other related transactions in the process may be performed over a data network such as the internet via a secure connection. The user then selects one of two user interfaces to input the patient's dental condition. The preferred method for the novice user is the visual-user interface (FIG. 17-22) shown as step 2802. The advanced user will likely prefer the alternative user interface (FIG. 25) illustrated as step 2803.

Referring to FIG. 28, at step 2804 an initial dentition condition of a patient in each category is compared to one or more reference conditions in the same category. After comparing the initial dentition condition of the patient in each category to one or more reference conditions for each respective category, at step 2804, the selected reference condition similar to the initial patient condition in the same category is received. Thereafter, at step 2805, the patient identifier is then generated based on the combination of alphanumeric characters corresponding to the selected reference conditions. Edits can be made to the inputs during the summary page review (step 2804) until the user is satisfied with the information submitted.

The output following the completion of the data input is a translation summary (FIG. 23), which formats the user input into technically relevant and correct terminology. At the same time, the user input is also translated into a database address representing the current patient condition (FIG. 25)—step 2805. Once the database address is created, the user can choose to view all possible treatment options for this patient (OPTION 1), or specifically select a treatment goal and view the specific goal associated with the user's selection (OPTION 2). To view all the possible treatment options for the patient (OPTION 1), the database (FIG. 27) is queried at step 2806, and all data associated with the input address is presented to the user at step 2807 (END 1).

Referring back to FIG. 28, if the user desires to select a specific goal, the specific goal is first defined by the user through a selection interface at step 2808 (FIG. 13), and the selection is then translated into a database address at step 2809 (FIG. 14), and the two addresses (patient condition and treatment goal) merged to create a combined address or index at step 2810 (FIG. 26). This combined address is then used to query the database at step 2811 (FIG. 27) in order to produce data specific to a single patient condition-treatment goal combination at step 2812 (END 2).

For OPTION 2, it may also be possible that the user can select multiple goals and only the data specific to those selected goals be produced for the user. Once the user has reached END 1 or END 2, the user has the option to purchase the product for the purpose of any one of the selected treatment goals, by selecting a pre-populated or semi-populated treatment prescription which can be part of the output data presented to the user through this experience.

As discussed above, the user interface can provide one or more patient cases from the indexing database that matches the patient problem. Additionally, a range of patient cases from the indexing database that address specific components of the patient's problem can be provided. In this manner, in one embodiment of the present invention, search tools may be created to run statistics using the patient identifiers. For example, one search request may be to find all 131X cases. In this exemplary search request, X represents any character in the fourth position of the address. Thus, the search request would be to find all patient identifiers having "131" as the first 3 digits of their patient identifier address.

By labeling historically treated cases with this identification methodology, a catalog of orthodontic treatment can be created for future reference when planning treatment and assessing treatment outcomes. The result is a front-end user interface for capturing the description of an orthodontic condition and classifying the orthodontic condition in a systematic scalable way. Referring again to FIG. 28, once the identifier is generated at step 2805, one or more treatment options can be determined using information generated from a database query. The generated one or more treatment options may be stored in the data storage unit 1107 (FIG. 11), and also, be provided to the terminal 1101 for display on the display unit.

Given the diagnosis and treatment planning of orthodontic treatments can include a significant subjective component that may vary depending upon the doctor's preferences and level of training, the indexing system provides a comprehensive, robust, and a substantially objective approach to establishing the patient diagnosis, treatment goal, and treatment plan. The patient identifier of the present invention which represents the patient's case, as well as the target treatment goal and final outcome enables treatment outcome profiles to be objectively catalogued, and for the catalog to be evaluated based on probabilities and distributions. Indices such as prognosis and case difficulty can be assigned to matrix combinations, enabling similar cases to be treated like similarly successful cases. Treatment options may be correlated for completeness and ease of use. Treatment products, such as appliances, may be associated with specific matrix combinations so that their suggested use is more closely tied to a successful outcome.

Within the scope of the present invention, other embodiments for inputting a patient's dentition condition are also contemplated. For example, a configurable three-dimensional model may be used to input the information. In such embodiment, the user may recreate the patient dentition condition for the dimension. Alternatively, a three-dimensional graphics model may be staged to represent the entire range of possible reference conditions for any given dimension. In such embodiment, a user manipulates a slider to match a stage of the range which is closest to the actual patient condition.

It will also be appreciated that this method of objectively characterizing a case according to individual components is not limited to the time points of pre-treatment, treatment goal, and post-treatment, and that any time point during treatment and following treatment may be also catalogued in a similar fashion using the same input and database system.

It will also be appreciated that in this exemplary embodiment although only one reference condition is discussed as being selected for a particular category, the present invention is not intended to be so limiting. The selection of one or more reference conditions within each category is within the scope of the present invention.

Accordingly, a method for characterizing a dentition of a patient in one embodiment of the present invention includes comparing an initial patient condition in each of a plurality of dentition categories with one or more reference conditions in each of the plurality of dentition categories, where each of the one or more reference conditions has a corresponding representation, selecting at least one reference condition in one or more of the plurality of dentition categories, where each selected reference condition is similar to the initial patient condition in a same dentition category, and generating a patient identifier based on the corresponding representations of each selected reference condition.

In one aspect, the plurality of dentition categories may include at least two of: sagittal, vertical, horizontal, upper and arch length dimensions, or a number of a tooth in a dentition of a patient.

Moreover, the method may further include determining whether each initial patient condition is indicated for treatment based on treatment information corresponding to the selected reference condition, providing one or more treatment options for each initial patient condition indicated for treatment, where the one or more treatment options include one or more of a treatment description, a treatment goal, a time to complete the treatment, a difficulty level, and a skill level to complete the treatment, an example of the treatment option.

Further, in another aspect, the method may also include comparing at least a portion of the patient identifier with one or more reference identifiers, wherein each of the one or more reference identifiers includes an initial reference dentition and a final reference dentition, selecting at least one reference identifier from the one or more reference identifiers, wherein the selected reference identifier includes the portion of the patient identifier, and determining a final patient dentition based on the final reference dentition corresponding to the selected reference identifier.

A method for characterizing a dentition of a patient in accordance with another embodiment of the present invention includes receiving an initial dentition of a patient, generating an initial profile representing the initial dentition of the patient, identifying an initial malocclusion from the initial profile, and comparing at least a portion of the initial profile with one or more reference profiles of reference dentitions, where said one or more reference profiles includes a reference malocclusion substantially similar to the initial malocclusion at the beginning, during any treatment stage, or final outcome treatment position.

Also, the method may also include the step of selecting at least one of the one or more reference profiles, where said one or more reference profiles has a related final reference dentition.

Additionally, in a further aspect, the method also includes providing a target dentition of the patient based on the final reference dentition.

The step of generating an initial profile in one embodiment may include visually categorizing the initial dentition of the patient.

Moreover, the method may also include identifying one or more treatment options associated with the one or more reference profiles.

A system for providing an orthodontic profile indexing system in accordance with still another embodiment of the present invention includes a storage unit, and a controller unit operatively coupled to the storage unit, and configured to compare an initial patient condition in each of a plurality of dentition categories with one or more reference conditions in each of the plurality of dentition categories, where each of the one or more reference conditions has a corresponding representation, select at least one reference condition in one or more of the plurality of dentition categories, where each selected reference condition is similar to the initial patient condition in a same dentition category, and to generate a patient identifier based on the corresponding representations of each selected reference condition.

The controller unit may be configured to determine whether each initial patient condition is eligible for treatment based on treatment information corresponding to the selected reference condition, and to provide one or more treatment options for each initial patient condition eligible for treatment.

Also, the controller unit may be further configured to compare at least a portion of the patient identifier with one or more reference identifiers, where each of the one or more reference identifiers includes an initial reference dentition and a final reference dentition, to select at least one reference identifier from the one or more reference identifiers, where the selected reference identifier includes the portion of the patient identifier, and to determine a final patient dentition based on the final reference dentition corresponding to the selected reference identifier.

In addition, a terminal may be operatively coupled to the controller unit, and configured to transmit one or more of the initial patient condition, where the terminal may be further configured to include a display unit.

A system for characterizing a dentition of a patient in accordance with still another embodiment of the present invention includes a central controller unit configured to generate an initial profile representing the initial dentition of the patient, to identify an initial malocclusion from the initial profile, and to compare at least a portion of the initial profile with one or more reference profiles of reference dentitions, wherein said one or more reference profiles includes a reference malocclusion substantially similar to the initial malocclusion.

In another aspect, a user terminal may be operatively coupled to the central controller unit, the user terminal configured to transmit the initial dentition of the patient.

The central controller unit may be further configured to select at least one of the one or more reference profiles, wherein said one or more reference profiles has a related final reference dentition.

In addition, the central controller unit may be further configured to provide a target dentition of the patient based on the final reference dentition.

The central controller unit may be further configured to visually categorize the initial dentition of the patient.

Moreover, the central controller unit may be further configured to identify one or more treatment options associated with the one or more reference profiles.

In yet still a further aspect, a storage unit may be configured to store one or more of an initial profile an initial malocclusion, and a reference malocclusion.

The various processes described above including the processes performed by the central server 1109 (FIG. 11) in the software application execution environment in the indexing system 1100 including the processes and routines described in conjunction with the Figures may be embodied as computer programs developed using an object oriented language that allows the modeling of complex systems with modular objects to create abstractions that are representative of real world, physical objects and their interrelationships. The software required to carry out the inventive process, which may be stored in the memory or data storage unit 1107 of the indexing system or internally (not shown) within the central server 1109, may be developed by a person of ordinary skill in the art and may include one or more computer program products.

While the characterization of adult dentition has been discussed in conjunction with the embodiments described above, the various embodiments of the present invention may be used for the characterization of child dentitions. In addition, in accordance with the embodiments of the present invention, the various aspects of the present invention may be manually implemented by the user, for example, using printout documentation, visual graphics, and/or photographic images of the conditions and/or treatment options, and further, may include, within the scope of the present invention, manual computation or calculation of the results. In this manner, within the scope of the present invention, the various embodiments discussed above in the context of a computerized system for implementing the aspects of the present invention, may be implemented manually.

Figure 29:
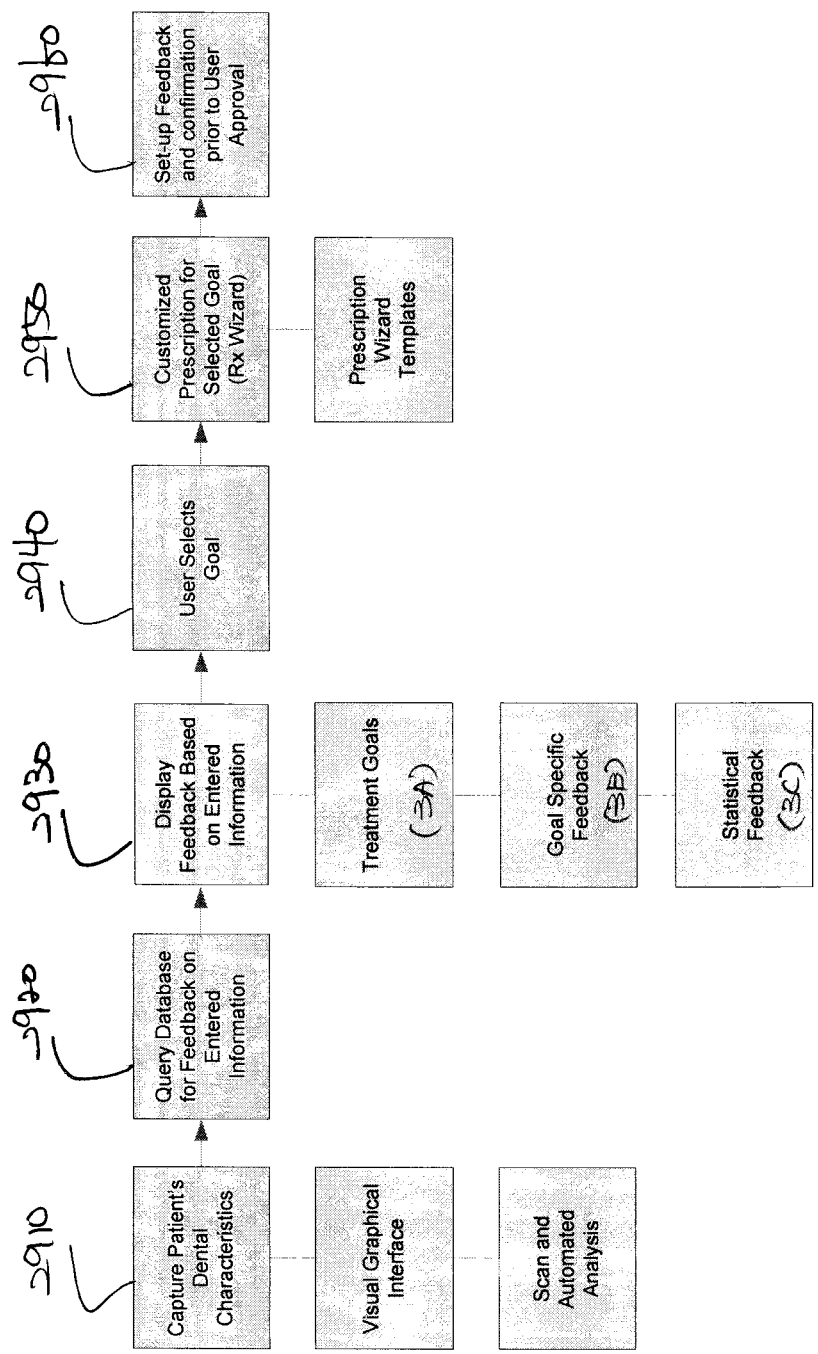
FIG. 29 is a flowchart illustrating the overall procedure for dynamic orthodontic treatment management in accordance with one embodiment of the present invention.

FIG. 29 is a flowchart illustrating the overall procedure for dynamic orthodontic treatment management in accordance with one embodiment of the present invention. Traditional orthodontic treatment assumes that a treatment goal is to ideal, when in fact, different treatment goals may be desired. Instead of making the treatment goal open-ended, the one embodiment of the present invention enables the user to select from one or more pre-defined treatment goals to enable the user to select a predefined treatment goal from one or more predefined treatment goals based on a patient's initial condition, thereby creating a paired combination between the pre-selected treatment goal and the patient's initial dental condition. The pairing between the treatment goal and the initial condition can then be linked to case related information, for example, indexed in one or more databases for that particular combination. This case related information may include, for example, doctor or clinician skill sets, case precautions, and assessment of difficulty for the particular combination.

In a further embodiment, the treatment goal may be open ended in a further embodiment such that the user may be provided with one or more treatment goals associated with the patient's initial orthodontic conditions, and where each of the one or more treatment goals may be associated with parameters related to the particular one or more treatment goals such as, for example, treatment difficulty assessment, treatment duration period, treatment appliance type, and the like.

Referring to FIG. 29, at step 2910, a patient's initial dental characteristics are captured. More specifically, in one embodiment, the patient's initial dental characteristics including, for example, the bite relationship, and severity of individual dental problems such as malocclusions, for example, are captured and stored in a database. In one embodiment, the initial dental characteristics may be manually input by the doctor, the clinician, or the patient, based upon, for example, visual inspection of the patient's dental characteristics. Alternatively, a visual graphical interface such as, for example but not limited to, a computer monitor, a personal digital assistant (PDA) graphical display unit, may be used to capture the initial dental characteristics.

More specifically, in one embodiment, the doctor, clinician or patient may be provided with a gradient of images on the visual graphical interface that show different dental conditions having varying degrees of differences. Then the doctor, clinician or the patient may visually compare the patient's dental characteristics with the gradient of images and select a corresponding one or more images from the gradient of images on the visual graphical interface. In this manner, the most similarly matched images from the visual graphical interface collectively in one embodiment may comprise the patient's dental characteristic diagnosis summary including each of the dental problems identified.

Referring back to FIG. 29, in a further embodiment, a three-dimensional (3-D) scan of the patient's teeth profile may be used in conjunction with the visual graphical interface as discussed above, to automatically capture the initial dental characteristics. This approach in one embodiment may provide higher dental profile assessment consistency and accuracy.

After the patient's initial dental characteristics are provided, the user may provide a predefined treatment goal based on the patient's initial dental characteristics. In one embodiment, as illustrated in FIG. 29, the user selects a predefined treatment goal from one or more predefined treatment goals based on feedback from a database query. In particular, after the patient's initial dental characteristics are provided at step 2910, a query function is executed at step 2920 to perform one or more searches from one or more databases associated with dental characteristics and dental treatment goals created at step 2910 based on the dental parameters. The query function enables a user to search for possible treatment goals based on the patient's initial dental parameters. A query function may also be executed at step 2920 to perform one or more searches from one or more databases associated with dental treatment plans based on one or more selected treatment goals and the patient's initial dental parameters.

Referring again to FIG. 29, at step 2930, feedback from the query function provides one or more case parameters associated with either treatment plan/profiles or treatment goals to the user. Based on the one or more case parameters, the user may determine the most suitable or desirable dental treatment goal or plan for the patient with the specified initial dental characteristics. The case parameters may include, for example, the type of appliances used for the treatment, the difficulty of the treatment, and the duration of the treatment. For example, based on the one or more case parameters, a selection may be determined based on the type of appliances used for the treatment.

More specifically, referring back to step 2930 at (3A), in one embodiment, one or more predefined treatment goals may be provided to the user (doctor, clinician or the patient) based on the patient's initial dental parameters. In such embodiment, the predefined treatment goals may include common treatment goals associated with the patient's initial dental parameters. For example, some predefined treatment goals are "pre-restorative setup", which involves aligning the teeth in anticipation of future dental work on the teeth following one or more orthodontic treatments; "esthetic alignment", which involves aligning the teeth for cosmetic improvement without altering the posterior bite relationship; "anterior function improvement", which involves aligning the teeth for improvement of the function and guiding relationship from the anterior teeth; and "optimal set-up", which involves aligning the teeth to provide as optimal of a bite relationship as possible given the patient's current initial dental characteristics.

In orthodontics there can be many different treatment goals which satisfy a patient's particular initial dental condition. Each of these goals may require different skills, and may have different prognoses depending on the patient's initial dental characteristics. The particular embodiments of the present invention enables a user to select a treatment goal based on case parameters associated with one or more potential treatment goals. This assists the user in better selecting an appropriate treatment plan. In addition, because the information is predefined for the initial dental characteristics/goal combination, the user can be provided with real-time feedback regarding the impact of changes to the prognosis/outcome by varying or modifying the individual parameters for the treatment goal. Similarly, feedback can be provided to a user based on variations or modifications to the initial dental parameters as well. In particular, the user may obtain modified treatment plans as feedback based on modifications to the initial dental parameters and/or modifications to a treatment goal.

Referring again to step 2930 at (3A), one or more treatment goals may be selected based on a difficulty rating. In such embodiment, each of the one or more predefined treatment goals may have an associated difficulty rating. For example, some doctors may have the skills or qualifications to treat only certain types of dental conditions or to treat only up to a certain treatment difficulty rating level. Thus, having a difficulty rating associated with each of the predefined treatment goals corresponding to the initial dental characteristics, may be helpful in assessing the impact of the treatment goal.

In a further embodiment, a maximum difficulty rating may be pre-designated for a particular user (for example, the doctor or clinician) such that the predefined treatment goals displayed as available to that user may include only those treatment goals up to the maximum pre-designated difficulty rating. In one embodiment, the difficulty ratings may be associated with an alphanumeric scale, a graphical scale (including icons, colors, images and the like), an auditory scale, or one or more combined scale for ease of use.

For example, in one embodiment, three difficult ratings or levels may be defined as follows: Difficulty level 1 (easy), difficulty level 2 (moderate), and difficulty level 3 (severe). For example, a user not familiar with the dynamic orthodontic treatment management of the present disclosure initially may be comfortable with treatment goals having difficulty level 1 rating, and want to prescribe a treatment goal that improves the patient's initial dental characteristics within an "easy" treatment plan.

In one embodiment, the user providing the pre-designated difficulty rating may include the patient having the initial dental characteristics for which orthodontic treatment is sought. In this manner, the patient may be provided with the treatment difficulty rating based on the selected one or more treatment goals such that the patient may selectively seek the suitable doctor or clinician with the appropriate level of treatment skills to perform the desired dental treatments.

Referring back to step 2930, at (3B) of FIG. 29, in one embodiment, the feedback from the query function provided to the user can also include rating of treatment goals once an initial assessment is created. In such embodiment, an assessment of treatment difficulty is done based on the combination of the patient's initial dental condition and selected goal. For example, a treatment difficulty indicator of 1, 2, or 3 may be attributed to a given initial dental condition/treatment goal combination, whereby "1" is a difficulty indicator of an "easy" combination, "2" is a difficulty indicator of a "moderate" combination, and "3" is a difficulty indicator of a "severe" combination. Difficulty indicators may also be associated with colors, symbols, and alphanumeric characters.

In one embodiment a difficulty indicator may be based on, for example, one or more look up tables for each of the parameters associated with the treatment of the patient's dental conditions. In one embodiment, the one or more lookup tables stored in the one or more databases, for example, may be segregated by treatment goal, such that different parameters of the patient's initial dental condition will be harder or easier to treat depending upon the selected treatment goal.

In one embodiment, each of the one or more lookup tables may include a pre-defined or pre-assigned difficulty indicator associated with each treatment related parameter, such that, a summation function of the difficulty value (in the case of a numerical difficulty indicator, for example) associated with each treatment related parameter may provide a composite difficulty value. Alternatively, in one embodiment, the composite difficulty value may be determined by comparing the individual difficulty values associated with all of the treatment parameters associated with the patient's initial dental characteristic, and thereafter, selecting the most severe difficulty value or rating associated with the particular treatment goal for the given initial dental characteristics and associated treatment parameters.

For example, the table below illustrates a difficulty assessment or value associated with the different levels of upper crowding and the upper midline deviation.

| | Upper Crowding (mm) | | | | |
|---|---|---|---|---|---|
| | 0 | 1 to 3 | 4 to 5 | 6 to 8 | 9+ |
| Difficulty | 0 | 1 | 2 | 3 | 4 |
| | | Upper | | | |
| Midline | Centered | 1 mm off | 2 mm off | 3 mm off | 4+ mm off |
| Difficulty | 0 | 1 | 2 | 3 | 4 |

From the table above, given a patient with initial dental conditions having 4 to 5 mm of upper crowding, and 1 mm upper midline deviation, the composite difficulty assessment may be determined by adding the individual difficulty assessment for the upper crowding (difficulty=2) and the upper midline deviation (difficulty=1), to derive at a composite difficulty assessment of three (3). Alternatively, as discussed above, the composite difficulty assessment or rating may be derived based upon a comparison of each difficulty assessment associated with each parameter, and thereafter, selecting the difficulty assessment or rating that is the most difficult based upon the comparison. For example, referring to the table above, comparing the difficulty assessment of two (2) associated with the upper crowding condition, with the difficulty assessment of one (1) associated with the patient's upper midline deviation, the composite difficulty assessment or rating may result at a rating of two (2).

Referring again to FIG. 29, the determined composite difficulty assessment or rating associated with the patient's initial dental characteristics and the related treatment parameters may be stored, for example, in one or more databases, and further, correlated with an overall difficulty assessment scale to determine the overall treatment difficulty. In one embodiment, the correlated overall difficulty assessment for the particular treatment may be provided to the user as, for example, a visual score. For example, in one embodiment, the overall treatment difficulty may be provided to the user using one or more of an alphanumeric output, a graphical output, an auditory output, or one or more combinations thereof.

The use of a difficulty assessment enables a finite set of parameters to describe a patient's orthodontic condition. In one embodiment, the difficulty of moving a patient's orthodontic condition from one state to another state with respect to each parameter is established in the form of a data table, in particular a difficulty table. In addition, the difficulty assessment rating or value stored in the tables may depend on a particular appliance intended for resolution of a malocclusion.

Referring again to step 2930 at (3C) of FIG. 29, in one embodiment, the feedback from the query function provided to the user can also include statistical information. In such embodiment, similar historically treated combinations of the selected parameter/goal combination are analyzed statistically to better inform the user. For example, in one embodiment, this information may be obtained using a historical compilation of patients having similar initial dental conditions sorted by historical treatment and outcome information. Statistical analysis is then performed on these historical data and the information categorically stored in one or more databases for query by the user.

More specifically, in one embodiment, the one or more databases associated with the execution of the query function (step 2920) as described above may be configured to include a historical patient treatment profile information and associated treatment related parameters including the respective patient initial dental conditions. In this manner, in one embodiment, one or more statistical analysis may be performed to query the one or more databases which includes historical treatment information and associated parameters related to, for example but not limited to, the patients' initial dental conditions, the treatment goals, the treatment plans, and the treatment outcome.

Some examples of the historical treatment information stored in the one or more databases discussed above include patient gender distribution, percentage and/or distribution of different treatment goals, average and actual treatment times, historical treatment success and associated criteria for determining successful treatments, one or more potential complications associated with the particular treatment parameter, the initial dental conditions, and associated or paired one or more treatment goals.

To determine the statistical analysis objectively and accurately, in one embodiment, cases of close similarity may be selected from the one or more databases storing historical treatment information. In one aspect, the similarity of the cases (and the underlying patient conditions and associated treatment parameters, for example) may be determined by using predefined one or more distance functions between two cases (that is, the current case under consideration and a historical case stored in the one or more databases including the historical treatment information). For example, the further the distance between the cases, the more similar the two cases.

In one embodiment, the distance function may be implemented by, for example, a processing module in the dynamic orthodontic treatment management, which may be configured to generate a predetermined number of closest matches to historical cases stored in the one or more databases including the historical treatment information. More specifically, in one embodiment, each parameter associated with the initial dental condition and associated treatment goals and other variables may be interrelated with each other based on a discrete distance determination, where the determined distance may be associated with the level of similarity between cases or parameters associated with the cases under consideration.

For example, applying the distance function to a current case and a historical case, similarity in an initial condition parameter (for example, incisor overjet) in the two cases under comparison may result in a relative closer distance relationship than other initial condition parameters. For example, if the initial condition parameter (for example, incisor overjet) is the same in both the current and historical cases, the distance between the cases is zero. That is, at least for the particular parameter under consideration, the two cases are identical. Alternatively, the distance function may be determined to be close (for example, on the order of one or two (as opposed to a substantially large number such as 100 which suggests a further distance relationship between the two cases)) if the current case includes class 1, 2-3 mm incisor overjet as compared to the historical case stored in the one or more databases which includes class 2, 3-5 mm incisor overjet.

For example, if a current case includes class 1, (2-3 mm incisor overjet) as compared to the historical case stored in the one or more databases which includes class 2, (3-5 mm incisor overjet), it is possible that values that were used to assign class 1 for current case and historical case are 1.95 and 2.05, respectively, and very close to each other. However they still belong to two different class assignments. Thus, one embodiment of the present invention allows an approximate matching for this particular parameter if class assignment conditions have common boundary. In the case where exact match of the particular parameter does not exist, the contribution of the particular parameter in determining the distance function between the current and historical cases may be slightly further apart, and preference will still be given to cases with exact match (if exists) when searching for similar cases. Moreover, another scenario where the approximate matching may be allowed includes cases where a particular parameter is less critical for the distance function when searching for similar cases.

In addition to the distance function, in one embodiment, each parameter under consideration may be further associated with a weighted function, where in one embodiment, weights may be configured to indicate the level of contribution of a particular parameter in combination with the distance function between the cases. In one embodiment, parameters which are more critical may be weighted more heavily and may be more important when searching for similar cases. Alternatively, parameters which may be less critical may be weighted less heavily and may be less important when searching for similar cases.

More specifically, depending upon the type of initial dental condition, the particular treatment goal or other associated parameters, certain aspects may be considered to be more important than others. For example, upper and lower arch length discrepancy, overbite, and overjet are considered relatively more important parameters than arch shape and presence of rotated bicuspids, and accordingly, in one aspect, the relatively more important parameters may be weighted more heavily than certain one or more relatively less important parameters such as arch shape or the presence of rotated bicuspids. As such, certain one or more of the important parameters may be weighted more heavily than certain one or more other relatively less important parameters. Moreover, in one embodiment, certain one or more parameters may be considered to be critical parameters such that the weighted value (and thus the possibility of potential possible deviation in determination of similar parameters in historical cases) may be substantially unmodifiable.

Moreover, in one embodiment, each of the parameters under consideration for each case under review may be interrelated to each other. Therefore, in one embodiment, a distance function determination and a corresponding weighted assessment may have a direct or indirect impact upon the previously determined distance function or the weighted assessment, such that a dynamically modifiable parameter assessment is obtained.

In one embodiment, the parameters under consideration may be classified or defined as follows: (1) parameters that require exact match between cases; (2) parameters that require exact match between cases depending upon the selected treatment goal; (3) query criteria restrictions including, for example—all cases for searching should be completed cases, ClinCheck® accepted cases; cases with or without additional aligners needed, completed or incompleted cases, and product or order-specific type cases, including for example, mid-course correction or case refinement; and (4) parameters that require approximate matching. It should be noted that while certain exemplary parameters and associated criteria for the query function is described herein, the examples provided herein are intended to be non-exclusive examples, and other relevant parameters and criteria may be included within the scope of the present invention.

In this manner, in one embodiment, similar cases may be selected by comparison of individual parameters, for example, between the current treatment case under consideration and the parameters of each historically treated or generated cases stored in the one or more databases. As discussed above, the parameters that are considered more important or critical are weighted more heavily, and are determined to be more important during the execution of the query function, while parameters which are less critical are weighted less heavily and are determined to be less important during the execution of the query function.

Referring back to FIG. 29, after receiving the feedback information at step 2930 associated with the one or more treatment goals for the underlying initial dental condition and the associated treatment parameter information, at step 2940, the user (for example, the doctor, clinician or the patient) may select one of the pre-defined treatment goals received as the desired or intended treatment direction. For example, in the case where the treatment duration is an important criterion, the user may select the one or more relevant treatment goals having the shortest treatment duration period given the underlying initial dental condition. Within the scope of the present invention, the user may select one or more pre-defined treatment goals as the desired treatment direction, including but not limited to, the treatment duration period as discussed above, the treatment appliance type (for example, Invisalign® aligners, brackets, a combination, and so on), the skill level necessary for treatment, probability of treatment success, estimated treatment length, estimated cost of treatment, and any other treatment goals or combinations thereof.

After selecting the one or more desired pre-defined treatment goals, the user may be provided with a treatment plan. In one embodiment, the treatment plan is provided as a prescription template on the visual guide interface. More specifically, referring to FIG. 29, at step 2950, the dynamic orthodontic treatment management system may be configured to generate and output a sequence of prompts for information to generate a prescription associated with the treatment plan based on the selected one or more pre-defined treatment goals. The content that is presented to the user is customized for the user depending on the treatment goal selected. In one embodiment, the prescription template displayed on the visual guide interface may be pre-customized based upon the user input information associated with the initial dental characteristics, associated treatment parameters and goals and other information that is necessary to complete the treatment prescription. In this manner, in one embodiment, information that is relevant and necessary is solicited from the user, while redundant information is not prompted for user input. For example, if the patient's bite profile is determined to be in the correct position, a prompt query asking whether a correction of the bite is desired is not necessary, and thus not generated for output to the user.

In one embodiment, the prescription templates may be generated, stored and retrieved for subsequent use. In this manner, the doctor or clinician may efficiently generate complete prescriptions to treat orthodontic related cases based on their particular preferences for treatment of specific types of cases, and thus are provided with an opportunity to use the same information consistently for treatment of similar types of cases, and are not required to provide the same information each time a prescription is required. Moreover, in one embodiment, while certain information may be repeated for similar types of cases in the prescription templates, the doctor or clinician may be also provided with an option to modify the pre-stored and retrieved information so as to possibly customize the particular prescription depending upon the treatment case under review.

Referring again to FIG. 29, upon completing the prescription for the treatment of the initial dental conditions in view of the selected treatment goals and other desired treatment associated parameters, the order associated with the prescription may be generated for placement at step 2960 during which, in one embodiment, a virtual setup of the patient's teeth based on the completed prescription is generated. The virtual setup of the patient's teeth may be verified for accuracy to confirm the selected treatment parameters, for example, such as the doctor or clinician's selected difficulty assessment associated with the treatment. In one embodiment, the virtual set up may be verified with the set up teeth movements and/or individual dental relationships, and the treatment related parameters may be queried in the one or more databases or analyzed with a planned treatment assessment algorithm to confirm if the expected difficulty assessment matches the expected difficulty level determined during the initial assessment, as discussed above.

Figure 30:
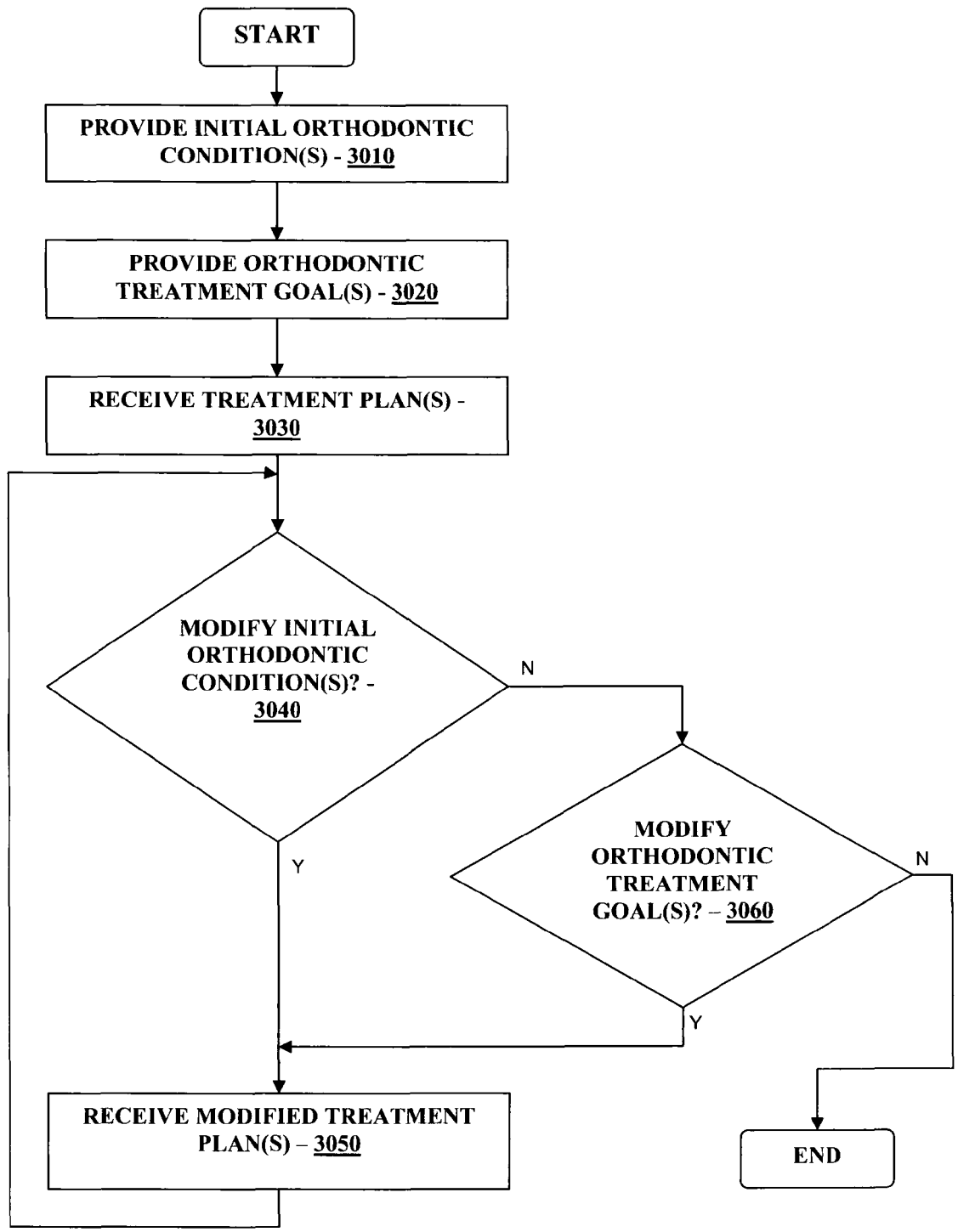
FIG. 30 is a flowchart illustrating dynamic treatment planning procedure in accordance with one embodiment of the present invention.

FIG. 30 is a flowchart illustrating a dynamic treatment planning procedure in accordance with one embodiment of the present invention. Referring to FIG. 30, at step 3010 initial orthodontic conditions are provided. For example, in one embodiment, the user which may include the patient, the doctor, or the clinician, may provide a patient's initial dental characteristics using the visual guide interface discussed above. In one embodiment, the initial orthodontic conditions may include characteristics of the patient's every tooth, groups of teeth, or alternatively, characteristics of a select number of teeth for which treatment is desired. Thereafter, at step 3020 the desired one or more orthodontic treatment goals are provided. In one embodiment, the one or more orthodontic treatment goals are predefined. Based on the information provided, at step 3030, the user receives one or more treatment plans associated with the initial orthodontic conditions and the selected treatment goals. In one embodiment, such treatment plans are received in substantially real time.

Referring to FIG. 30, at step 3040 the user determines whether to modify one or more parameters associated with the initial dental conditions. If it is determined that the initial dental conditions are not modified, then at step 3060 it is determined whether one or more parameters associated with the treatment goals is modified. If it is determined that the initial orthodontic conditions and the treatment goals are not modified, then the dynamic treatment planning procedure ends. However, if it is determined that one or more parameters associated with either the initial orthodontic conditions or the treatment goals is modified, then at step 3050, a modified treatment plan is received.

Figure 31:
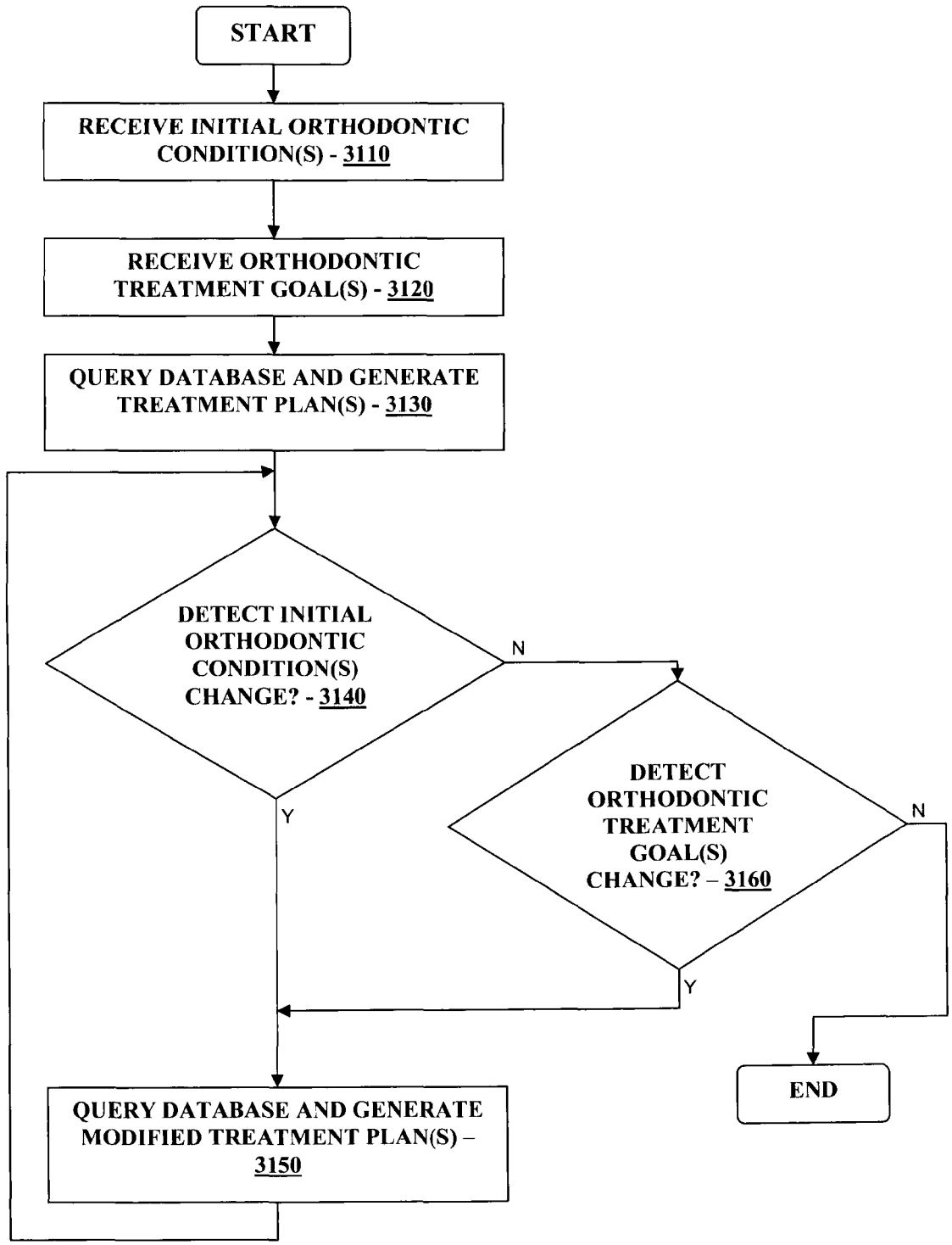
FIG. 31 is a flowchart illustrating dynamic treatment planning procedure in accordance with another embodiment of the present invention.

FIG. 31 is a flowchart illustrating a dynamic treatment planning procedure in accordance with another embodiment of the present invention. Referring to FIG. 31, in one embodiment, the initial orthodontic conditions and associated parameters are received at step 3110, and at step 3120 the desired treatment goals are received. Thereafter, at step 3130, one or more databases are queried based on the received initial orthodontic conditions and associated parameters and the desired treatment goals, and one or more treatment plans are generated. The generated one or more treatment plans are output to the user and thereafter, at step 3140 it is determined whether any change to the initial dental conditions parameters are changed. If it is determined that the initial dental condition parameters are not changed, then at step 3160 it is determined whether the treatment goal parameters are changed. If at step 3160 it is determined that the treatment goal parameters are not changed, then the dynamic treatment planning procedure ends.

On the other hand, if it is determined at step 3140 that one or more initial orthodontic conditions are changed, or if it is determined at step 3160 that one or more parameters associated with the treatment goals has changed, then at step 3150 the one or more databases are queried based on the changed or modified parameters, and a modified treatment plan is generated for output to the user. Thereafter, the procedure returns to step 3140 and the procedure described above is repeated until no additional changes to the initial orthodontic conditions or to the treatment goals are detected.

In this manner, in one embodiment, by providing the initial dental condition and a specified treatment goal pairing, a treatment plan is provided that is associated with the case prognosis based on the specified condition—goal pairing. Moreover, based on the received treatment plan, the user may optionally modify one or more parameters associated with the condition—goal pairing to determine a more desirable or suitable treatment plan that is within the specified treatment parameters such as treatment difficulty, types of appliances, and the like.

Accordingly, in one embodiment, the user may be provided with real time dental related treatment planning support that is substantially objective. Moreover, the user may be provided with more comprehensive treatment related information including the impact of individual treatment goal parameters on the overall assessment of the treatment plan associated with, for example, a particular dental appliance.

Figure 32:
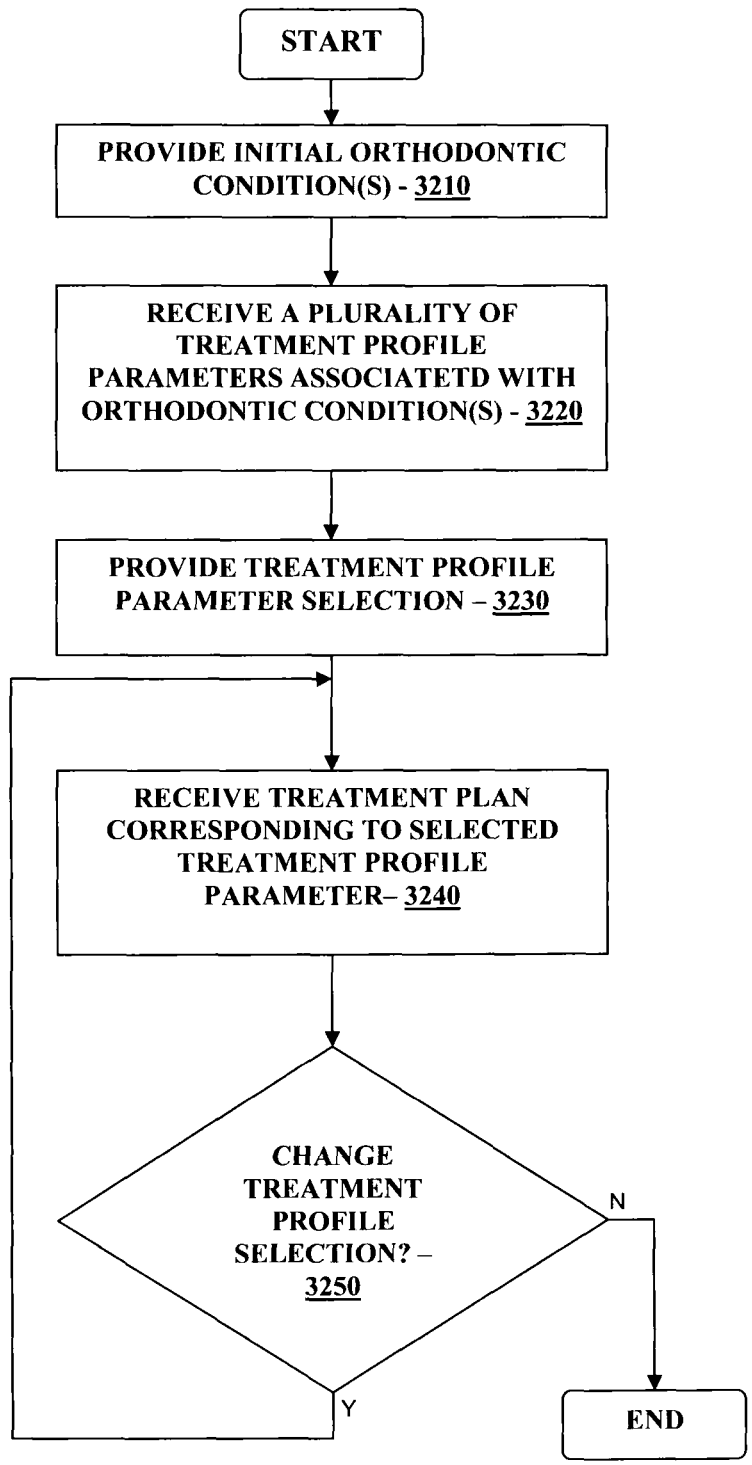
FIG. 32 is a flowchart illustrating dynamic treatment planning procedure in accordance with yet another embodiment of the present invention.

FIG. 32 is a flowchart illustrating dynamic treatment planning procedure in accordance with yet another embodiment of the present invention. Referring to FIG. 32, at step 3210 the initial orthodontic conditions are provided, and at step 3220, one or more treatment goals are received. These one or more treatment goals include treatment profile parameters associated with the provided initial orthodontic conditions. Thereafter at step 3230, a treatment goal selection is provided which includes selected treatment profile parameters, and at step 3240 a treatment plan corresponding to the selected treatment goal is received. For example, in one embodiment, the patient's initial dentition information may be provided using for example, the visual guide interface, and thereafter, a plurality of treatment profile parameters associated with the treatment option of the initial dentition information is received. In one embodiment, the treatment goal may include one or more of the following treatment parameters: treatment difficulty assessment, the appliance type available for treatment, the treatment duration, and the like.

Upon receiving the treatment plan information associated with the selection of the treatment goal for the patient's particular dentition information, at step 3250 the user may modify or change one or more treatment parameters associated with the treatment plan information. If the user modifies the one or more treatment parameters associated with the treatment plan information, the procedure returns to step 3240 where the treatment plan based upon the modified or changed treatment plan parameter is received. Thereafter, the user may further modify the treatment parameters to determine corresponding change in the associated treatment plan. The procedure continues until no further changes to the treatment profile parameters are made.

Figure 33:
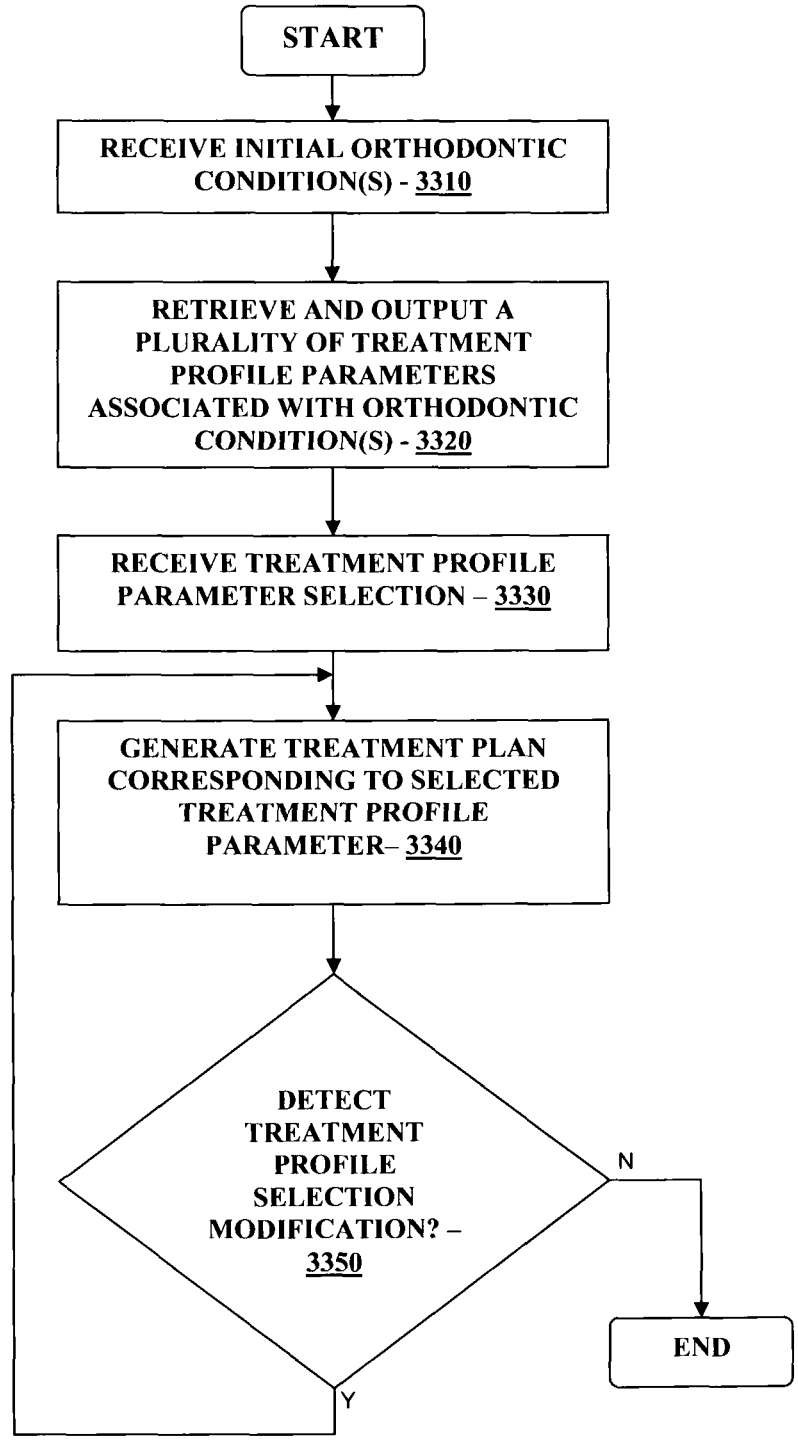
FIG. 33 is a flowchart illustrating dynamic treatment planning procedure in accordance with still another embodiment of the present invention.

FIG. 33 is a flowchart illustrating a dynamic treatment planning procedure in accordance with still another embodiment of the present invention. Referring to FIG. 33, at step 3310, the patient's initial orthodontic condition is received, and at step 3320, a plurality of treatment goals, which include treatment profile parameters associated with the orthodontic condition, are retrieved and output to the user. In one embodiment, the plurality of treatment profile parameters associated with the orthodontic condition may be retrieved based upon the execution of one or more query functions in the one or more databases as described above associated with the initial dental condition of the patient.

Referring again to FIG. 33, at step 3330, a treatment goal selection, which includes treatment profile parameters, is received, and thereafter, a corresponding treatment plan associated with the selected treatment goal and the initial orthodontic condition is generated and output to the user. Thereafter, it is determined at step 3350 whether a modification to the one or more treatment profile parameters of the selected treatment goal is detected. If it is determined that no change to the treatment profile parameters are detected, then the procedure ends. On the other hand, if it is determined at step 3350 that one or more treatment profile parameter modifications is detected, then the procedure returns to step 3340 and a corresponding treatment plan is generated and output to the user based on the detected modification to the treatment profile parameters.

In this manner, in one embodiment, a feedback mechanism is provided where based upon an initial virtual setup of a patient's dental conditions, a treatment assessment is provided which is configured to provide a difference in the treatment plans based upon changes in the treatment profile parameters such as, for example, differing treatment goals, differing treatment difficulty associated with each treatment plan, or different types of appliances to be used for treatment. Accordingly, in one embodiment, by allowing modifications to the treatment profile parameters, the user may readily and easily determine the necessary skill level and other treatment related information, and thereafter, make suitable or appropriate changes to obtain the desired treatment. For example, in the case where the user determines that a particular doctor is not skilled to perform the desired treatment, the user may seek another doctor that has the necessary expertise for performing the desired treatment. In addition, in one embodiment, based upon the treatment profile parameters and the associated treatment plan, a recommendation of suitable skilled doctors may be provided to the user.

Accordingly, in one embodiment, there is provided a substantially objective manner in which to assess a patient's orthodontic conditions, and which may be configured to provide consistent and repeatable results or treatment plan recommendations, and to remove some or all of the subjective assessment criteria based on manual assessment by doctors.

Figure 34:
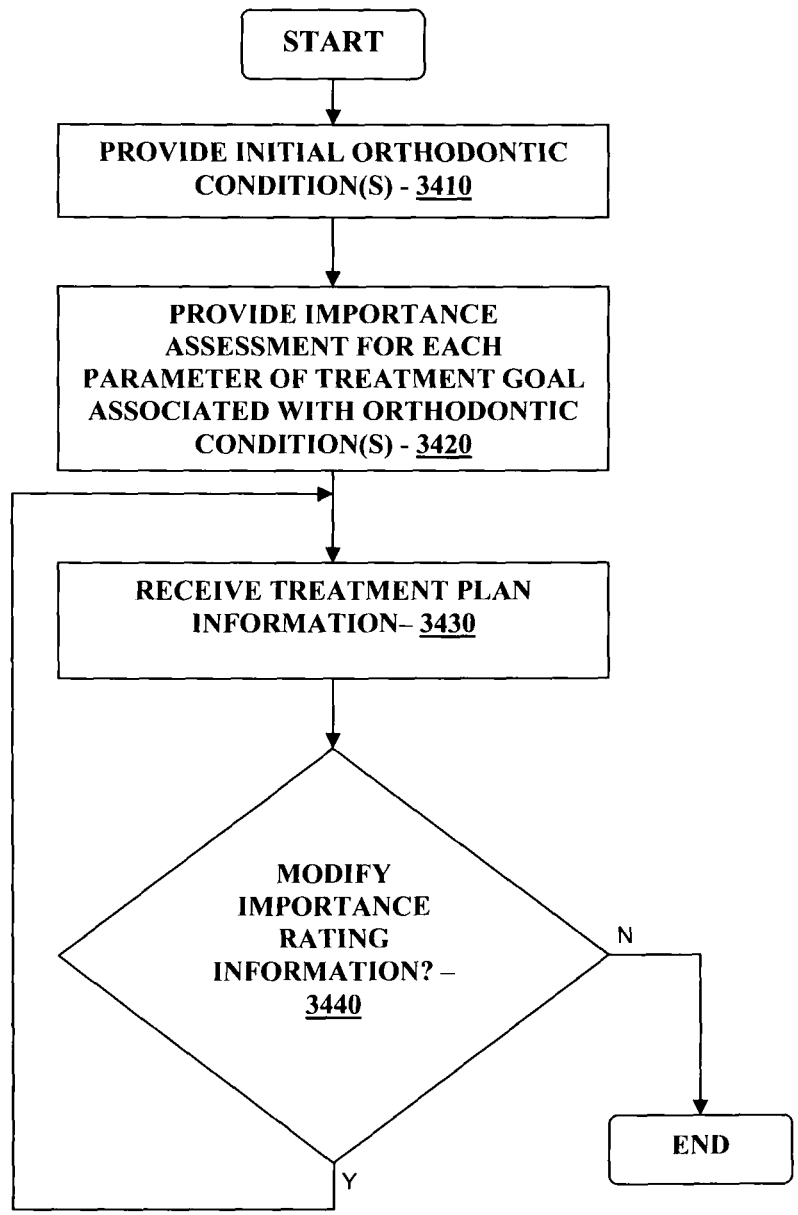
FIG. 34 is a flowchart illustrating dynamic treatment profile assessment in accordance with one embodiment of the present invention.

FIG. 34 is a flowchart illustrating a dynamic treatment profile assessment procedure in accordance with one embodiment of the present invention. Referring to FIG. 34, at step 3410 the initial orthodontic condition information is provided and thereafter, an importance assessment or rating information for each parameter associated with a desired treatment goal is provided at step 3420. For example, in one embodiment, the user may provide information related to the patient's initial dental conditions, and thereafter, provide information associated with the desired treatment goal that is weighted or associated with a predetermined importance rating using, for example, objective, predefined scaling.

Referring to FIG. 34, at step 3430, treatment plan information is received based upon the treatment goal with scaled parameters that has been provided with importance assessment. Based on the received treatment plan information, at step 3440 it is determined whether the importance assessment or rating information is modified. If it is determined that the importance assessment associated with the treatment plan is not modified, then the routine ends. On the other hand, if it is determined at step 3440 that the importance assessment or rating associated with one or more of treatment profile parameters corresponding to the desired treatment goal is modified, then the routine returns to step 3430 where the treatment plan information based on the modified importance rating information is received.

In other words, in one embodiment, modification to the importance assessment of a particular one or more treatment goal parameters associated with the patient's dental conditions, in turn, modifies the corresponding treatment plan information factoring in the modified importance assessment associated with the treatment goal for the patient's particular dental conditions.

Figure 35:
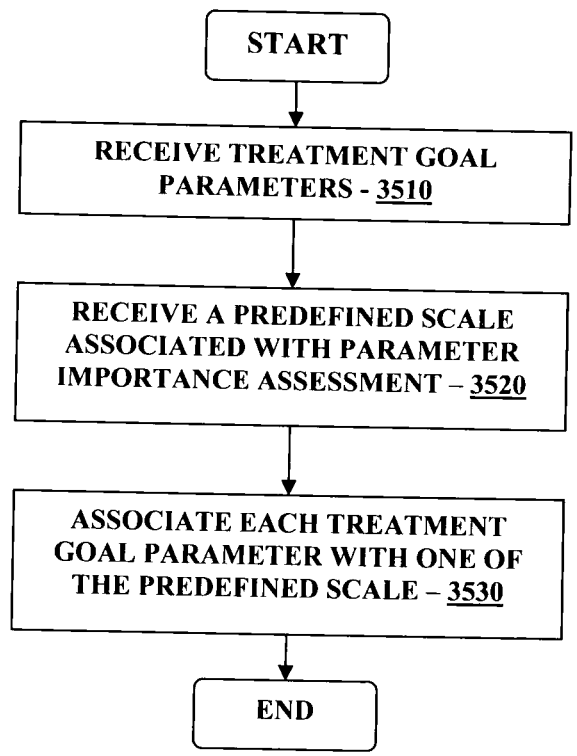
FIG. 35 is a flowchart illustrating importance assessment of FIG. 34 in accordance with one embodiment of the present invention.

FIG. 35 is a flowchart illustrating importance assessment of FIG. 34 in accordance with one embodiment of the present invention. Referring to FIG. 35, in one embodiment at step 3510 one or more treatment goal parameters is received, and thereafter, a predefined scale of information associated with the parameter importance assessment is received. For example, in one embodiment, the user may be provided with an objective criteria or scale by which to determine the respective importance assessment associated with the one or more treatment profile parameters.

That is, in one embodiment, a numerical scale from 1 to 5 may be provided to the user to correlate each of the one or more parameters associated with the desired treatment goal. While a numerical scale is used, within the scope of the present invention, any other types of suitable scale that provides an objective criterion to determine relative importance may be provided. Referring to FIG. 35, at step 3530 each of the treatment goal parameters is associated with a desired or intended predefined scale. Based upon this importance assessment, the corresponding treatment plan information is received (FIG. 34).

Figure 36:
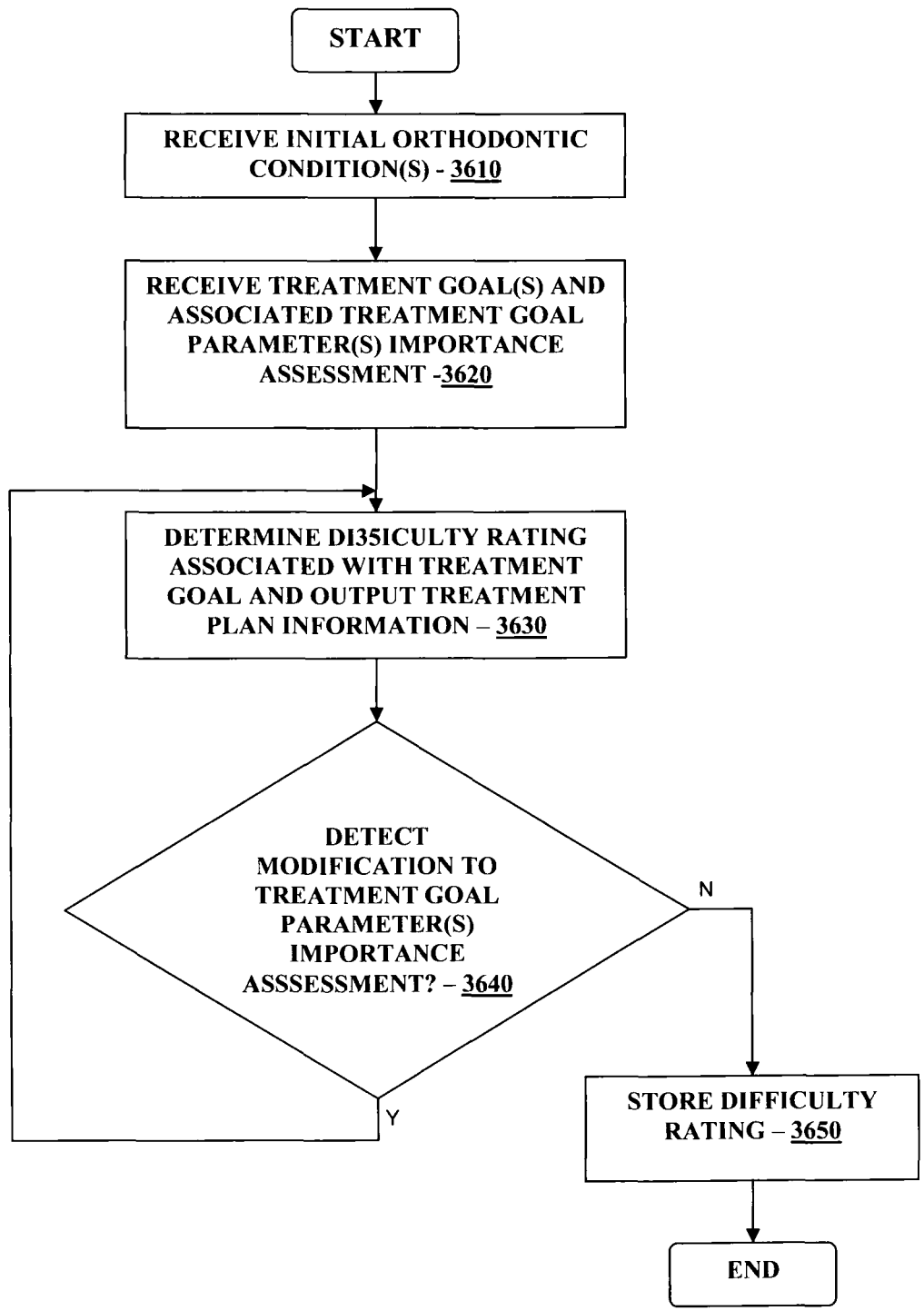
FIG. 36 is a flowchart illustrating dynamic treatment profile assessment in accordance with another embodiment of the present invention.

FIG. 36 is a flowchart illustrating a dynamic treatment profile assessment procedure in accordance with another embodiment of the present invention. Referring to FIG. 36, at step 3610 the initial orthodontic conditions of a patient are received, and thereafter, one or more treatment goals and associated treatment goal parameters having importance assessments are received at step 3620. For example, in one embodiment, one or more of the treatment goal parameters may be associated with a predefined importance assessment scale. In this manner, the treatment goal and the relative importance of one or more of the treatment goal parameters are received.

Referring to FIG. 36, at step 3630, a difficulty assessment rating associated with the treatment goal is determined and respective treatment plan information associated with both the treatment goal and the initial dental conditions is output to the user. Thereafter, at step 3640, it is determined whether any changes to the treatment goal parameters having importance assessment are detected. That is, based on the treatment plan information, it is determined whether the user has modified any or all of the previously associated importance assessment to the treatment goal parameters. If it is determined at step 3640 that modification to the treatment goal parameters importance assessment is not detected, then the difficulty rating associated with the treatment goal parameters and the corresponding treatment plan information is stored in the one or more databases at step 3650, and the routine ends.

On the other hand, if it is determined that modification to the treatment goal parameters importance assessment is detected, then the routine returns to step 3630 to determine the difficulty rating associated with the treatment goal parameters with modified importance rating assessment. This routine is repeated until no modification to the importance assessment associated with the treatment goal parameters is detected.

In this manner, in one embodiment, treatment plan information includes for example, treatment difficulty information that is associated with a necessary level of treatment skill required for performing the treatment. If a doctor does not possess the necessary level of treatment skill, in one embodiment, one or more parameters including an importance assessment associated with the one or more parameters may be modified such that one or more treatment plans for treating the particular dental conditions of the patient may be determined that are within the skill level of the doctor.

Figure 37:
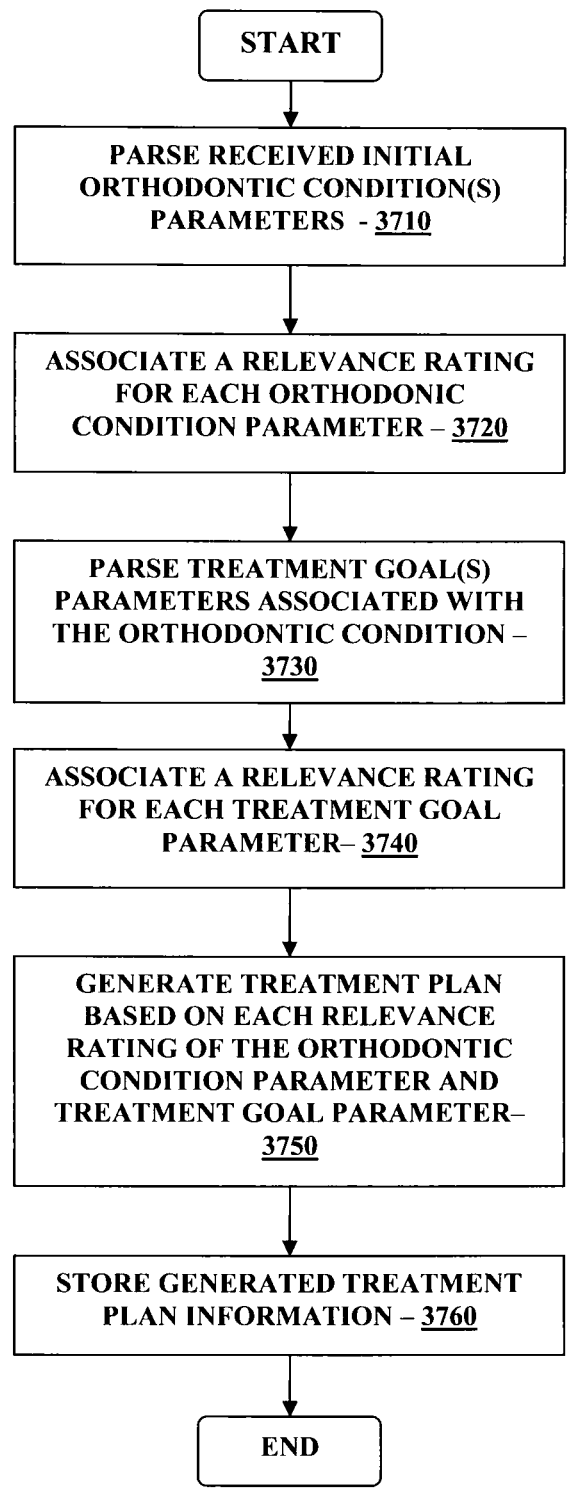
FIG. 37 is a flowchart illustrating dynamically weighted treatment planning assessment in accordance with one embodiment of the present invention.

FIG. 37 is a flowchart illustrating dynamically weighted treatment planning assessment in accordance with one embodiment of the present invention. Referring to FIG. 37, at step 3710 the initial orthodontic condition parameters are parsed. In one embodiment, the query function may be configured to parse the information associated with the initial dental characteristics received from the user into predetermined categories. Thereafter, at step 3720, each parsed orthodontic condition parameter is associated with a relevance rating based on, in one embodiment, a predetermined relevance or weighted function. At step 3730, the received treatment goal parameters associated with the orthodontic condition is parsed by, for example, the query function, and, each treatment goal parameter is associated with a respective relevance rating at step 3740.

In one embodiment, the relevance rating for each of the initial orthodontic condition parameters and the treatment goal parameters may be determined based on similarity of the each of the initial orthodontic condition parameters and the treatment goal parameters to one or more previously treated cases or historical information associated with the case profile or past treatment information related to the initial orthodontic condition parameters and the treatment goal parameters, for example, as discussed above.

Referring again to FIG. 37, at step 3750 based on each relevance rating associated with the initial orthodontic condition parameters and the treatment goal parameters, a corresponding treatment plan is generated and output to the user. Thereafter, at step 3760 the generated treatment plan information is stored in the one or more databases. In this manner, in one embodiment of the present invention, an objective relevance rating may be associated with one or more of the initial orthodontic condition parameters and the treatment goal parameters to retrieve prior treatment profiles that includes the same or similar initial orthodontic condition parameters and the treatment goal parameters, and based upon which the corresponding treatment plan may be generated.

Figure 38:
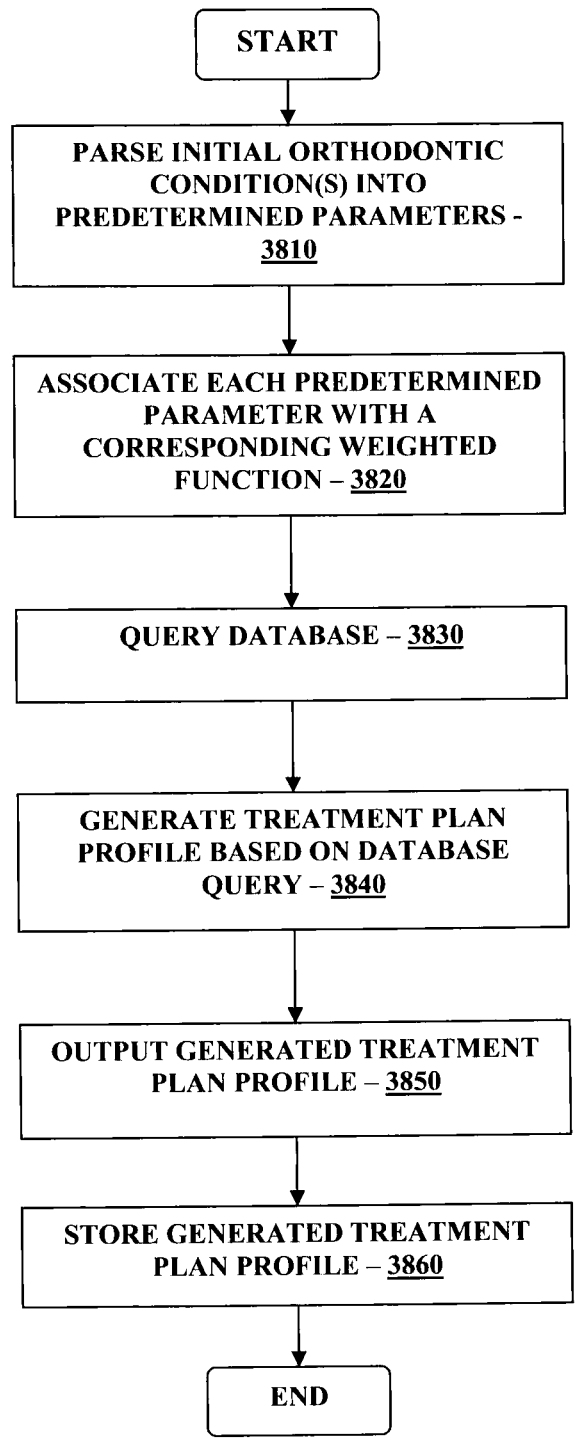
FIG. 38 is a flowchart illustrating dynamically weighted treatment planning assessment in accordance with another embodiment of the present invention.

FIG. 38 is a flowchart illustrating dynamically weighted treatment planning assessment in accordance with another embodiment of the present invention. Referring to FIG. 38, in one embodiment, at step 3810 the initial orthodontic conditions are parsed into one or more predetermined parameters. For example, in one embodiment the initial orthodontic conditions received may be parsed into some or all of the approximately 25 diagnostic parameter categories. Thereafter, at step 3820 each predetermined parameter is associated with a corresponding weighted function. That is, as discussed above, the parameters associated with the patient's dental conditions are weighted based upon a predetermined criteria, such as, for example, the importance of the particular parameter in relation to the overall desired treatment goal, the difficulty of addressing the particular parameter in view of the available appliances for treatment, and so on.

Referring back to FIG. 38, at step 3830 the one or more databases is queried based upon the one or more predetermined parameters associated with a corresponding weighted function, and at step 3840, a treatment plan profile is generated based on the database query. As shown in FIG. 38, the generated treatment plan profile is output to the user at step 3850, and thereafter stored in the one or more databases at step 3860.

In this manner, in one embodiment of the present invention, each parameter associated with the patient's dental condition may be evaluated based upon a predetermined weighted function and also, upon the inter-dependencies of each parameter associated with the patient's initial dental condition, to determine the corresponding treatment plan based on, for example, previously treated cases that have similar or the same characteristics associated with the patient's condition and/or the desired treatment goal. Accordingly, in one embodiment, by identifying successfully treated prior cases and using parameters and information associated with the prior cases, users such as doctors, clinicians and the patients may be provided with detailed relevant information associated with the treatment of prior similar cases in determining the treatment direction.

Figure 39:
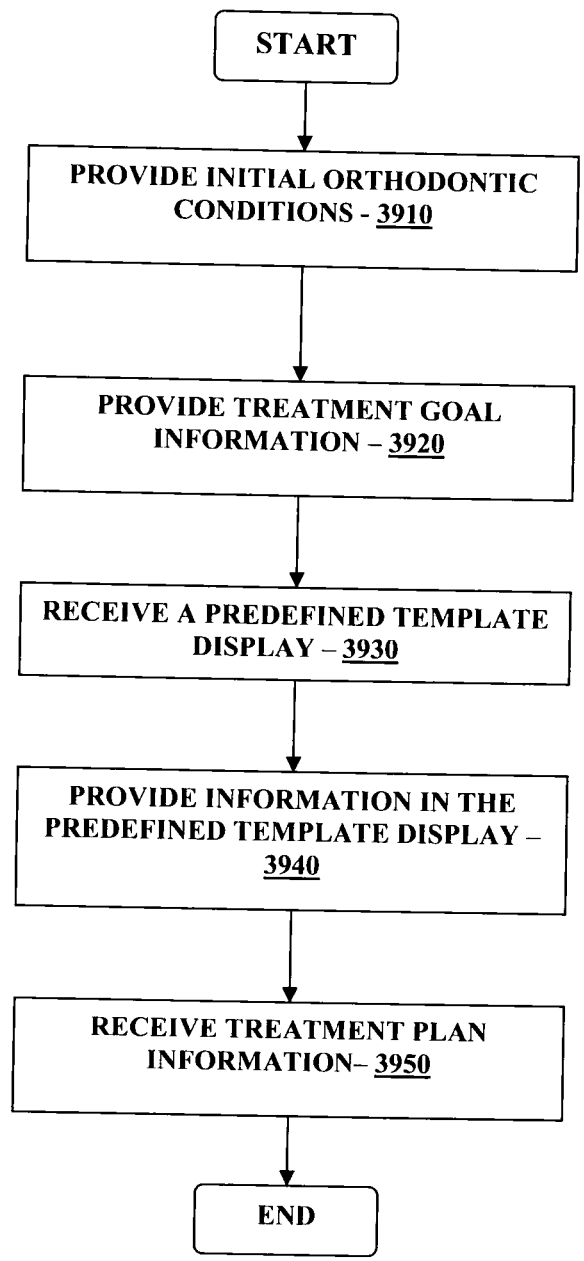
FIG. 39 is a flowchart illustrating a predefined template manipulation in the overall procedure for dynamic orthodontic treatment management in accordance with one embodiment of the present invention.

FIG. 39 is a flowchart illustrating a predefined template manipulation in the overall procedure for dynamic orthodontic treatment management in accordance with one embodiment of the present invention. Referring to FIG. 39, in one embodiment, information associated with the initial orthodontic conditions is provided at step 3910. Thereafter, the treatment goal information associated with the initial orthodontic conditions is provided at step 3920. At step 3930, a predefined template display is received in, for example, the visual guide interface which may include, for example, information that has been pre-filled in. That is, based upon the information provided associated with the initial dental conditions and the selected treatment goal, a prescription template may be received which includes some information that has been automatically added into the template.

Referring to FIG. 39, at step 3940, information is provided in the predefined template display to complete the one or more data entry fields which are necessary to complete the prescription for the treatment of the patient's dental conditions in view of the selected treatment goal. Thereafter, at step 3950 treatment plan information is received which is associated with the patient's dental conditions and the selected treatment goal for the dental conditions.

Figure 40:
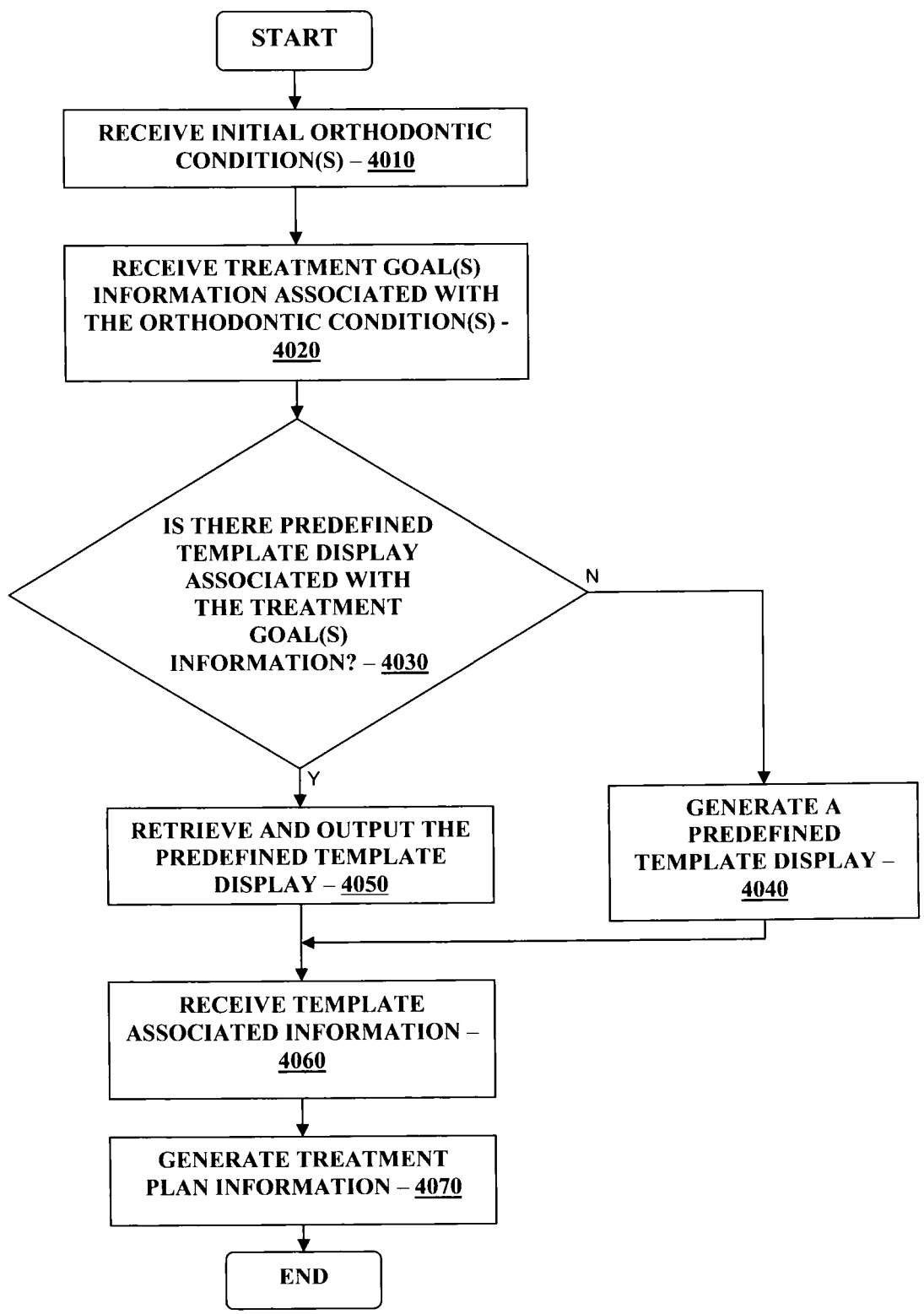
FIG. 40 is a flowchart illustrating a predefined template manipulation in the overall procedure for dynamic orthodontic treatment management in accordance with another embodiment of the present invention.

FIG. 40 is a flowchart illustrating a predefined template manipulation in the overall procedure for dynamic orthodontic treatment management in accordance with another embodiment of the present invention. Referring to FIG. 40, at step 4010 the initial orthodontic conditions are received and the treatment goal information associated with the patient's dental conditions is received at step 4020. Thereafter at step 4030, it is determined whether there is a predefined template display associated with the treatment goal information received. That is, in one embodiment, the one or more databases are searched to determine if there is a suitable or appropriate predefined template display associated with the selected treatment goal.

If it is determined that there is no predefined template display, then at step 4040 a predefined template display is generated and output to the user. In one embodiment, the predefined template display may be generated to include information in one or more select data fields associated with the patient's dental conditions or the selected treatment goal. On the other hand, if it is determined at step 4030 that a predefined template display associated with the selected treatment goal information is in the one or more databases, then at step 4050 the determined predefined template display is retrieved in addition to the information in one or more select data fields associated with the predetermined template display and associated with the patient's dental conditions or the selected treatment goal, and thereafter the predefined template display is output to the user.

Referring back to FIG. 40, at step 4060, information associated with the predefined template display is received, and when it is determined that all of the necessary information is received to complete a treatment prescription associated with the treatment goal for the patient's dental conditions, then at step 4070, treatment plan information is generated and output to the user.

In this manner, in one embodiment, the process of generating a prescription for orthodontic treatments may be simplified such that, using existing template information or generating an appropriate template associated with a specific treatment goal, certain information may be retrieved and pre-filled into the prescription form template, for example, the information that is associated with the patient's initial orthodontic condition, while other relevant information may be prompted for input from the user. In one embodiment, the user may store the prescription information in the predefined template display format such that the user may retrieve the predefined template display for future treatment of similar types of cases. In a further aspect, the predefined template display may be associated with a particular one or more of an indexed or categorized value or score of the patient's initial dental conditions, with the treatment goal, or with any other customizable characteristics, such that the user may retrieve the predefined template display for subsequent similar cases for treatment.

Systems and methods are disclosed providing a database comprising a compendium of at least one of patient treatment history; orthodontic therapies, orthodontic information and diagnostics; employing a data mining technique for interrogating said database for generating an output data stream, the output data stream correlating a patient malocclusion with an orthodontic treatment; and applying the output data stream to improve a dental appliance or a dental appliance usage.

The achieved outcome, if measured, is usually determined using a set of standard criteria such as by the American Board of Orthodontics, against which the final outcome is compared, and is usually a set of idealized norms of what the ideal occlusion and bite relationship ought to be. Another method of determining outcome is to use a relative improvement index such as PAR, IOTN, and ICON to measure degrees of improvement as a result of treatment.

The present invention provides methods and apparatus for mining relationships in treatment outcome and using the mined data to enhance treatment plans or enhance appliance configurations in a process of repositioning teeth from an initial tooth arrangement to a final tooth arrangement. The invention can operate to define how repositioning is accomplished by a series of appliances or by a series of adjustments to appliances configured to reposition individual teeth incrementally. The invention can be applied advantageously to specify a series of appliances formed as polymeric shells having the tooth-receiving cavities, that is, shells of the kind described in U.S. Pat. No. 5,975,893.

A patient's teeth are repositioned from an initial tooth arrangement to a final tooth arrangement by making a series of incremental position adjustments using appliances specified in accordance with the invention. In one implementation, the invention is used to specify shapes for the above-mentioned polymeric shell appliances. The first appliance of a series will have a geometry selected to reposition the teeth from the initial tooth arrangement to a first intermediate arrangement. The appliance is intended to be worn until the first intermediate arrangement is approached or achieved, and then one or more additional (intermediate) appliances are successively placed on the teeth. The final appliance has a geometry selected to progressively reposition teeth from the last intermediate arrangement to a desired final tooth arrangement.

The invention specifies the appliances so that they apply an acceptable level of force, cause discomfort only within acceptable bounds, and achieve the desired increment of tooth repositioning in an acceptable period of time. The invention can be implemented to interact with other parts of a computational orthodontic system, and in particular to interact with a path definition module that calculates the paths taken by teeth as they are repositioned during treatment.

In general, in one aspect, the invention provides methods and corresponding apparatus for segmenting an orthodontic treatment path into clinically appropriate substeps for repositioning the teeth of a patient. The methods include providing a digital finite element model of the shape and material of each of a sequence of appliances to be applied to a patient; providing a digital finite element model of the teeth and related mouth tissue of the patient; computing the actual effect of the appliances on the teeth by analyzing the finite elements models computationally; and evaluating the effect against clinical constraints. Advantageous implementations can include one or more of the following features. The appliances can be braces, including brackets and archwires, polymeric shells, including shells manufactured by stereo lithography, retainers, or other forms of orthodontic appliance. Implementations can include comparing the actual effect of the appliances with an intended effect of the appliances; and identifying an appliance as an unsatisfactory appliance if the actual effect of the appliance is more than a threshold different from the intended effect of the appliance and modifying a model of the unsatisfactory appliance according to the results of the comparison. The model and resulting appliance can be modified by altering the shape of the unsatisfactory appliance, by adding a dimple, by adding material to cause an overcorrection of tooth position, by adding a ridge of material to increase stiffness, by adding a rim of material along a gumline to increase stiffness, by removing material to reduce stiffness, or by redefining the shape to be a shape defined by the complement of the difference between the intended effect and the actual effect of the unsatisfactory appliance. The clinical constraints can include a maximum rate of displacement of a tooth, a maximum force on a tooth, and a desired end position of a tooth. The maximum force can be a linear force or a torsional force. The maximum rate of displacement can be a linear or an angular rate of displacement. The apparatus of the invention can be implemented as a system, or it can be implemented as a computer program product, tangibly stored on a computer-readable medium, having instructions operable to cause a computer to perform the steps of the method of the invention.

Among the advantages of the invention are one or more of the following. Appliances specified in accordance with the invention apply no more than orthodontically acceptable levels of force, cause no more than an acceptable amount of patient discomfort, and achieve the desired increment of tooth repositioning in an acceptable period of time. The invention can be used to augment a computational or manual process for defining tooth paths in orthodontic treatment by confirming that proposed paths can be achieved by the appliance under consideration and within user-selectable constraints of good orthodontic practice. Use of the invention to design aligners allows the designer (human or automated) to finely tune the performance of the aligners with respect to particular constraints. Also, more precise orthodontic control over the effect of the aligners can be achieved and their behavior can be better predicted than would otherwise be the case. In addition, computationally defining the aligner geometry facilitates direct aligner manufacturing under numerical control.

A computer-implemented method in accordance with one embodiment of the present invention includes receiving one or more parameters associated with an orthodontic condition, receiving a treatment goal information associated with the orthodontic condition, providing a predefined template associated with the received treatment goal information, wherein the predefined template includes at least one the orthodontic condition related information.

In one embodiment, providing the predefined template may include querying a database based on the treatment goal information for the predefined template, and generating the predefined template when it is determined during querying the database that the predefined template is not stored in the database.

Also, providing the predefined template may include retrieving the predefined template from a database for display to a user.

The method may also include generating a treatment plan information based on the information received in the predefined template, and also may include providing the treatment plan information to a user.

The method may further include receiving a modified treatment goal information.

In one aspect, the method may additionally include querying a database based on the modified treatment goal information, providing a modified predefined template, where providing the modified predefined template may include generating the modified predefined template based on the modified treatment goal information associated with the orthodontic condition.

In still another aspect, the method may also include storing the modified predefined template.

A computer-implemented method in accordance with another embodiment of the present invention includes receiving one or more parameters associated with an orthodontic condition, receiving a treatment goal information associated with the orthodontic condition, searching a database for a predefined template associated with the orthodontic condition and the treatment goal information, retrieving information associated with the orthodontic condition and the treatment goal information, completing at least a portion of the predefined template with the retrieved information, and providing the predefined template completed with the retrieved information.

In one aspect, searching the database may include selecting from a plurality of predefined templates the predefined template associated with the orthodontic condition and the treatment goal information.

The method may further include generating a treatment plan information based on the information received in the predefined template.

A system in accordance with yet another embodiment includes a data storage unit, and a data processing unit operatively coupled to the data storage unit, the data processing unit configured to receive one or more parameters associated with an orthodontic condition, to receive a treatment goal information associated with the orthodontic condition, and to provide a predefined template associated with the received treatment goal information, wherein the predefined template includes at least one the orthodontic condition related information.

The data processing unit may be configured to query the data storage unit based on the treatment goal information for the predefined template, and to generate the predefined template when it is determined during querying the database that the predefined template is not stored in the database.

The system may include a display unit operatively coupled to the data processing unit, the data processing unit further configured to retrieve the predefined template from the data storage unit for display on the display unit.

In one aspect, the data processing unit may be configured to generate a treatment plan information based on the information received in the predefined template.

The data processing unit may further be configured to receive a modified treatment goal information, where the data processing unit may be additional also configured to query the data storage unit based on the modified treatment goal information, to provide a modified predefined template based on the query.

The data processing unit in yet another aspect may be configured to generate the modified predefined template based on the modified treatment goal information associated with the orthodontic condition.

Moreover, in still another embodiment, the data processing unit may be configured to store the modified predefined template in the data storage unit.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A computer-implemented method, comprising:
   comparing a patient initial orthodontic condition with one or more reference orthodontic conditions in each of a plurality of dentition categories;
   selecting at least one reference orthodontic condition in one or more of the plurality of dentition categories that is similar to the patient initial orthodontic condition in a same dentition category;
   generating, by the computer, a patient identifier based on the selected at least one reference orthodontic condition;
   wherein the patient identifier includes a plurality of positions each corresponding to one of the plurality of dentition categories, and wherein each of the plurality of positions includes a value equal to a value of the selected reference orthodontic condition for the corresponding one of the plurality of dentition categories;
   receiving treatment goal information associated with the patient initial orthodontic condition and the patient identifier; and
   determining whether a predefined template is associated with the treatment goal information.

2. The computer-implemented method of claim 1 wherein determining whether the predefined template is associated with the treatment goal information includes:
   querying a database based on the treatment goal information for the predefined template; and
   generating the predefined template when it is determined during querying the database that the predefined template is not stored in the database, wherein the predefined template includes pre-filled in information in one or more data fields associated with the one or more initial orthodontic conditions and the received treatment goal information.

3. The computer-implemented method of claim 1 wherein the method includes retrieving the predefined template from a database for display to a user.

4. The computer-implemented method of claim 1 further including generating a treatment plan information based on the information received in the predefined template.

5. The computer-implemented method of claim 1 further including receiving a modified treatment goal information.

6. The computer-implemented method of claim 5 wherein determining whether the predefined template is associated with the treatment goal information includes:
   querying a database based on the modified treatment goal information; and
   providing a modified predefined template.

7. The computer-implemented method of claim 6 wherein providing the modified predefined template includes generating the modified predefined template based on the modified treatment goal information associated with the initial orthodontic condition.

8. The computer-implemented method of claim 6 further including storing the modified predefined template.

9. The computer-implemented method of claim 8 wherein the modified predefined template is retrieved and used for subsequent similar cases for treatment.

10. A computer-implemented method, comprising:
    comparing one or more initial orthodontic conditions with one or more reference orthodontic conditions in each of a plurality of dentition categories;
    selecting at least one reference orthodontic condition in one or more of the plurality of dentition categories that is similar to the one or more initial orthodontic conditions in a same dentition category;

generating, by the computer, a patient identifier based on the selected at least one reference orthodontic condition;

wherein the patient identifier includes a plurality of positions each corresponding to one of the plurality of dentition categories, and wherein each of the plurality of positions includes a value equal to a value of the selected reference orthodontic condition for the corresponding one of the plurality of dentition categories;

receiving a treatment goal information associated with the one or more initial orthodontic conditions and the patient identifier; and searching a database for a predefined template including pre-filled in information in one or more data fields associated with the one or more initial orthodontic conditions and the received treatment goal information, wherein the predefined template is associated with one or more of the patient identifier and the treatment goal.

11. The computer-implemented method of claim 10 wherein searching the database includes selecting from a plurality of predefined templates the predefined template associated with the initial orthodontic condition and the treatment goal information.

12. The computer-implemented method of claim 10 further including:

retrieving information associated with the one or more initial orthodontic conditions and the treatment goal information;

completing at least a portion of the predefined template with the retrieved information;

providing the predefined template completed with the retrieved information; and generating a treatment plan information based on the information received in the predefined template.

13. A system, comprising:

a data storage unit; and a data processing unit operatively coupled to the data storage unit, the data processing unit configured to:

compare a patient initial orthodontic condition with one or more reference orthodontic conditions in each of a plurality of dentition categories, select at least one reference orthodontic condition in one or more of the plurality of dentition categories that is similar to the patient initial orthodontic condition in a same dentition category, generate a patient identifier based on the selected at least one reference orthodontic condition, wherein the patient identifier includes a plurality of positions each corresponding to one of the plurality of dentition categories, and wherein each of the plurality of positions includes a value equal to a value of the selected reference orthodontic condition for the corresponding one of the plurality of dentition categories, receive a treatment goal information associated with the patient initial orthodontic condition and the patient identifier, and determine whether a predefined template is associated with the treatment goal information.

14. The system of claim 13 wherein the data processing unit is configured to query the data storage unit based on the treatment goal information for the predefined template, and to generate the predefined template when it is determined during querying the database that the predefined template is not stored in the database.

15. The system of claim 13 further including a display unit operatively coupled to the data processing unit, the data processing unit further configured to retrieve the predefined template from the data storage unit for display on the display unit.

16. The system of claim 13 wherein the data processing unit is further configured to generate a treatment plan information based on the information received in the predefined template.

17. The system of claim 13 wherein the data processing unit is further configured to receive a modified treatment goal information, and wherein the predefined template includes pre-filled in information in one or more data fields associated with the patient initial orthodontic condition and the received treatment goal information.

18. The system of claim 17 wherein the data processing unit is further configured to query the data storage unit based on the modified treatment goal information, to provide a modified predefined template based on the query.

19. The system of claim 18 wherein the data processing unit is further configured to generate the modified predefined template based on the modified treatment goal information associated with the initial orthodontic condition.

20. The system of claim 18 wherein the data processing unit is further configured to store the modified predefined template in the data storage unit.

21. The system of claim 20 wherein the modified predefined template is retrieved from the data storage unit for display on the display unit and used for subsequent similar cases for treatment.

* * * * *